US012648929B2

(12) United States Patent　　(10) Patent No.:　US 12,648,929 B2
Mitre et al.　　　　　　　　　　(45) Date of Patent:　　Jun. 9, 2026

(54) COMPOSITIONS AND METHODS FOR PREVENTING AND/OR TREATING FILARIAL DISEASE

(71) Applicants:The Henry M. Jackson Foundation for the Advancement of Military Medicine, Inc., Bethesda, MD (US); THE UNITED STATES OF AMERICA, AS REPRESENTED BY THE SECRETARY, DEPT OF HEALTH AND HUMAN SERVICES, Bethesda, MD (US)

(72) Inventors: Edward Elais Saul Mitre, Rockville, MD (US); Christopher Paul Morris, Frederick, MD (US); Alexander Francis Flynn, Odenton, MD (US); Thomas B. Nutman, Chevy Chase, MD (US); Sasisekhar Bennuru, Rockville, MD (US)

(73) Assignees: THE HENRY M. JACKSON FOUNDATION FOR THE ADVANCEMENT OF MILITARY MEDICINE, INC., Bethesda, MD (US); THE UNITED STATES OF AMERICA, AS REPRESENTED BY THE SECRETARY, DEPT OF HEALTH AND HUMAN SERVICES, Bethesda, MD (US)

( * ) Notice:　Subject to any disclaimer, the term of this patent is extended or adjusted under 35 U.S.C. 154(b) by 1423 days.

(21) Appl. No.:　17/273,212

(22) PCT Filed:　Sep. 6, 2019

(86) PCT No.:　PCT/US2019/049869
　　§ 371 (c)(1),
　　(2) Date:　Mar. 3, 2021

(87) PCT Pub. No.:　WO2020/051408
　　PCT Pub. Date: Mar. 12, 2020

(65)　　　　　Prior Publication Data
　　US 2021/0220333 A1　　Jul. 22, 2021

Related U.S. Application Data

(60) Provisional application No. 62/728,312, filed on Sep. 7, 2018.

(51) Int. Cl.
　　*A61K 31/4152*　　(2006.01)
　　*A61K 31/195*　　(2006.01)
　　*A61K 31/4184*　　(2006.01)
　　*A61P 33/10*　　(2006.01)
　　*C07K 16/40*　　(2006.01)
　　*C07K 16/42*　　(2006.01)

(52) U.S. Cl.
　　CPC ........ *A61K 31/4152* (2013.01); *A61K 31/195* (2013.01); *A61K 31/4184* (2013.01); *A61P 33/10* (2018.01); *C07K 16/40* (2013.01); *C07K 16/42* (2013.01)

(58) Field of Classification Search
　　CPC .............. A61K 31/4152; A61K 31/195; A61K 31/4184; A61K 31/015; A61K 31/196; A61K 31/277; A61K 31/352; A61K 31/357; A61K 31/365; A61K 31/603; A61K 31/713; A61K 31/395; A61K 31/427; A61K 31/455; A61K 31/485; A61K 31/496; A61K 31/505; A61K 45/06; A61P 33/10; C07K 16/40; C07K 16/42; Y02A 50/30
　　See application file for complete search history.

(56)　　　　　References Cited

U.S. PATENT DOCUMENTS

2013/0137669 A1　　5/2013　Prichard et al.
2018/0064791 A1　　3/2018　Mitre et al.

FOREIGN PATENT DOCUMENTS

AU　　　　2014213568 A1 *　3/2015
WO　　　　2009067797 A1　　6/2009
WO　　　　2011026112 A1　　3/2011
WO　　WO-2016149460 A1 *　9/2016　......... A61K 38/1767

OTHER PUBLICATIONS

Kaifi, J., et.al., "Distinct roles for PECAM-1, ICAM-1, and VCAM-1 in recruitment of neutrophils, and eosinophils to the cornea in Ocular Onchocerciasis (river blindness)" J. Immunol. 2001 166(11), 6795-6801 (Year: 2001).*
Simón, F., et al. "Dirofilaria immitis and Wolbachia-derived antigens: Its effect on endothelial mammal cells." Veterinary Parasitology 2008 158, 223-231 (Year: 2008).*
Morris, C., et. al., "A proteomic analysis of the body wall, digestive tract, and reproductive tract of Brugia malayi." PLoS Negl. Trop. Dis. 2015 9(9): e0004054 (Year: 2015).*
Paddock, C. et. al., "Structural basis for PECAM-1 homophilic binding." Blood 2016, 127(8) 1052-1061 (Year: 2016).*
Lakshmi et al., 2010, Antifilarial activity in vitro and in vivo of some flavonoids tested against Brugia malayi, Acta Tropica, 116: 127-133 (Year: 2010).*

(Continued)

*Primary Examiner* — Joanne Hama
(74) *Attorney, Agent, or Firm* — MH2 Technology Law Group, LLP

(57)　　　　　ABSTRACT
The present disclosure is directed to methods for preventing or treating helminth (e.g., filarial) diseases in animals. The methods are accomplished by administering to the animal a therapeutically effective amount of an inhibitor of UDP-glucoronosyl transferase (UGT) or immunoglobulin I-set domain containing protein (Igl-DCP, also known as BMA-Lad-2). The inhibitors include those known to inhibit glucuronyltransferase enzyme activity as well as cell adhesion molecule inhibitors and antibodies specific for Igl-DCP and/or UGT.

19 Claims, 15 Drawing Sheets

Specification includes a Sequence Listing.

(56) References Cited

OTHER PUBLICATIONS

Molento et al., 1999, Effects of the multi-drug-resistance-reversing agents verapamil and CL 347,099 on the efficacy of ivermectin or moxidectin against unselected and drug-selected strains of Haemonchus contortus in jirds (*Meriones unguiculatus*), Parasitol. Res., 85: 1007-1011 (Year: 1999).*

Garg et al., 2011, Genital filariasis masquerading as testicular torsion, J. Vector Borne Dis, 48: 119-121 (Year: 2011).*

Liu et al., 2017, Combinatorial chemistry in drug discovery, Current Opinion in Chemical Biology, 38: 117-126 (Year: 2017).*

Chiu et al., 2018 Antibody Structure and Function: The Basis for Engineering Therapeutics, Antibodies, 8, 55 (doi:10.3390/antib8040055 (Year: 2018).*

Flynn, 2018, Evaluating Intestinal Proteins of Adult Brugia malayi Worms as Drug and Vaccine Targets, retrieved on Oct. 13, 2025 <URL: https://apps.dtic.mil/sti/trecms/pdf/AD1128272.pdf> (candidate for PhD, Aug. 15, 2018. (Year: 2018).*

Thomsen et al., 2015, Efficacy, Safety, and Pharmacokinetics of Coadministered Diethylcarbamazine, Albendazole, and Ivermectin for Treatment of Bancroftian Filariasis, Clinical Infectious Diseases, vol. 62, Issue 3, Feb. 1, 2016, pp. 334-341 (Year: 2016).*

International Search Report and Written Opinion dated Jan. 9, 2020 from International Application No. PCT/US2019/049869 (Authorized Officer, Shane Thomas), 14 Pages.

Kotze et al., "Phenobarbital Induction and Chemical Synergism Demonstrate the Role of UDP-Glucuronosyltransferases in Detoxification of Naphthalophos by Haemonchus contortus Larvae", Antimicrobial Agents and Chemotherapy, 2014, vol. 58, No. 12, pp. 7475-7483.

Emery et al., "Haemonchus contortus: the then and now, and where to from here?", International Journal for Parasitology, 2016, vol. 46, pp. 755-769.

Ghosh et al., "Anti-adhesion molecule therapy for inflammatory bowel disease", Therapeutic Advances in Gastroenterology, 2010, vol. 3, No. 4, pp. 239-258.

Diemert et al., "Safety and immunogenicity of the Na-GST-1 hookworm vaccine in Brazilian and American adults", PLOS Neglected Tropical Diseases, 2017, vol. 11, No. 5, 22 pages.

Morris et al., "A Comprehensive, Model-Based Review of Vaccine and Repeat Infection Trials for Filariasis", Clinical Microbiology Reviews, 2013, vol. 26, No. 3, pp. 381-421.

Morris et al., "A Proteomic Analysis of the Body Wall, Digestive Tract, and Reproductive Tract of Brugia malayi", PLOS Neglected Tropical Diseases, 2015, vol. 9, No. 9, 21 pages.

Matoušková et al., "The Role of Xenobiotic-Metabolizing Enzymes in Anthelmintic Deactivation and Resistance in Helminths", Trends in Parasitology, 2016, vol. 32, No. 6, pp. 481-491.

Walsky et al., "Optimized Assays for Human UDP-Glucuronosyltransferase (UGT) Activities: Altered Alamethicin Concentration and Utility to Screen for UGT Inhibitors", Drug Metabolism and Disposition, 2012, vol. 40, No. 5, pp. 1051-1065.

Extended European Search Report dated Sep. 29, 2022 for corresponding European Patent Application No. 19857011, 13 pages.

Office Action dated Nov. 1, 2023 for corresponding Canadian Patent Application No. 3,110,571, 4 pages.

Christine Bourque (Examiner), Office Action dated Mar. 31, 2026 for corresponding Canadian Patent Application No. 3,110,571, 4 pages.

Liu et al., "Inhibitory Effect of Hesperetin and Naringenin on Human UDP-Glucuronosyltransferase Enzymes: Implications for Herb-Drug Interactions", Biological and Pharmaceutical Bulletin, 2016, vol. 39, No. 12, pp. 2052-2059 (available at https://www.jstage.jst.go.jp/article/bpb/39/12/39_b16-00581/_pdf).

* cited by examiner

COMPOSITIONS AND METHODS FOR PREVENTING AND/OR TREATING FILARIAL DISEASE

CROSS-REFERENCE TO RELATED APPLICATIONS

This application is a U.S. National Stage application of PCT/US2019/049869 filed 6 Sep. 2019, which claims the benefit of, and relies on the filing date of, U.S. provisional patent application No. 62/728,312, filed 7 Sep. 2018, the entire disclosure of which is incorporated herein by reference.

STATEMENT OF GOVERNMENT INTEREST

This invention was made with government support under grants R073UE and F173424117 from the Uniformed Services University of the Health Sciences. The government has certain rights in the invention.

SEQUENCE LISTING

The instant application contains a Sequence Listing which has been submitted electronically in ASCII format and is hereby incorporated by reference in its entirety. Said ASCII copy, created on 6 Sep. 2019, is named HMJ-155-PCT_SL.txt and is 46 kilobytes in size.

BACKGROUND

Helminths are multicellular eukaryotic invertebrates with tube-like or flattened bodies exhibiting bilateral symmetry. Helminths can be either free-living, typically in aquatic and terrestrial environments, or parasitic, taking up residence in a host animal or plant. Parasitic helminths are almost universally found in vertebrate animals. Three major categories of parasitic helminths are recognized: the Acanthocephalins (thorny-headed worms), the Nemathelminthes (nematodes), and the Platyhelminthes (flatworms), which are subdivided into the Cestoda (tapeworms) and the Trematoda (flukes).

Nematodes are divided into two classes based on the presence or absence of special chemoreceptors known as phasmids: Secernentea (Phasmidea) and Adenophorea (Aphasmidea). While numerous orders fall within these classes, the main parasitic nematodes infecting humans and domestic animals include one aphasmid order (Trichocephalida; also called whip-worms) and six phasmid orders Oxyurida (also called pin-worms), Ascaridida (also called roundworms), Strongylida (also called hookworms), Rhabditida (also called threadworms), Camallanida (also called guinea worms, and Spirurida (also called filarial worms).

Many parasitic helminths belong to the Spirurida order. The filarial worms are thread-like, parasitic nematodes that are transmitted by arthropod vectors. The adult worms inhabit specific tissues where they mate and produce microfilariae, the characteristic tiny, thread-like larvae. Microfilariae infect vector arthropods in which they mature to infective larvae.

Diseases caused by filariae are a major health problem in many tropical and subtropical areas. *Wuchereria bancrofti* and *Brugia malayi* are filarial parasites that are the major causative agents of lymphatic filariasis (LF). Currently, it is estimated that over 129 million people are infected with either of these organisms and over 1.4 billion people live in at-risk areas. Since 2000, there has been an ongoing effort through the Global Program to Eliminate Lymphatic Filariasis to eradicate these infections. Global eradication efforts have significantly reduced worldwide prevalence, but complete elimination has been hampered by limitations of current anti-filarial drugs and the lack of a vaccine. (Morris et al., *Clin. Microbiol. Rev.,* 26(3):381-421, 2013). Thus, while this program is having a substantive impact on the prevalence of infection, its efficacy is limited by the need to repeatedly treat entire endemic populations for 6-10 years.

Other diseases known in the art that are caused by filarial parasites include heartworm disease. This disease is caused by the parasite *Dirofilaria immitis*. The physical presence of the heartworm parasite in the pulmonary artery and right ventricle of the canine heart, for example, and the resulting destruction of tissue, causes respiratory and circulatory problems which can be fatal under conditions of stress or vigorous exercise. The heartworm parasite has also been shown to be the cause of focal lung, liver, eye and cutaneous lesions in man.

Currently, heartworm disease is treated by administering anti-parasitic agents to infected animals. Unfortunately, heartworm disease that has not been diagnosed in its early stages may be quite refractile to treatment. Current antifilarials such as ivermectin and milbemycin can effectively protect dogs and cats by blocking maturation of infective L3 larvae into adults (ivermectin is the developed form of the drug avermectin, the discovery of which lead to the Nobel prize in Physiology or Medicine to Drs. William C. Campbell and Satoshi Omura in 2015). However, these prophylactics need to be administered monthly and costs upwards of 100 USD per year per pet. Considering the 80 million dogs in the United States alone, administering prophylactic treatment nationwide has an immense financial impact. In addition, while there are several drugs that protect animals from infection, there is only one U.S. Food and Drug Administration (FDA)—approved drug to treat against adult worms, called melarsomine. This drug is expensive and can lead to embolization of dead worms and ultimately cause severe pulmonary thrombosis and hypertension. Development of alternative treatments and approaches to this pervasive issue is needed.

Other current antifilarial drugs, diethylcarbamazine (DEC), ivermectin (IVM), and albendazole effectively target the microfilariae, but lack robust macrofilaricidal activity. (Subrahmanyam D., *Ciba Found Symp.,* 1987; 127:246-64; Venkatesan et al., *J. Antimicrob. Chemother.,* 1998; 41(2): 145-7; Richard-Lenoble et al., *Fundam. Clin. Pharmacol.,* 2003; 17(2):199-203). Current practice dictates a regimen of annual dose of DEC or ivermectin alone or in combination with albendazole. However, DEC and IVM cannot be administered empirically in areas endemic for *Loa loa* or *Onchocerca volvulus* because the drugs can precipitate severe side effects by rapid killing of microfilariae. (Twum-Danso N A., *Filaria J,* 2003; 2 Suppl 1:S7; Wanji et al., *PLoS Negl Trop Dis.,* 2017; 11(7):e0005576; Albiez et al., *Trop Med Parasitol.,* 1988; 39(1):19-24; Awadzi et al., *Br J Clin Pharmacol.,* 1992; 34(4):281-8).

The advent of new tools, such as vaccines or more effective anthelmintics (antiparasitic drugs that expel parasitic worms (helminths) and other internal parasites from the body by either stunning or killing them and without causing significant damage to the host), would be of great benefit toward these eradication efforts.

However, one of the principle obstacles in designing vaccines against such parasitic worms is that previously exposed individuals frequently possess in their bloodstream IgE antibodies specific to surface and secreted worm antigens, putting these individuals at risk for allergic reactions when re-exposed to these antigens via vaccine. Since intestinal antigens of helminths may be "hidden" from the immune response during natural infection, yet accessible by antibodies after antigen administration, homogenates of such antigens have been proposed for use in vaccines. However, while the genomes of *Wuchereria bancrofti* and *Brugia malayi*, as well as the filarial genomes of the causative agents of loiasis and river blindness have been completed, the anatomic localization of proteins in these filarial worms is unknown. Moreover, the use of homogenates from helminth intestines has resulted in variable efficacy. (Morris et al., *Clin. Microbiol. Rev.*, 26(3):381-421, 2013). Vaccines have been attempted with little success due to these potential allergic responses, an example of which is the failed Na-ASP-2 hookworm vaccine. (See, Diemert et al., *J. Allergy Clin. Immunol.*, 130(1):169-176, 2012).

Further, turning to anthelmintics, a major factor limiting effectiveness of current mass drug administration (MDA) efforts to control and potentially eradicate lymphatic filariasis and onchocerciasis is the inability of current antifilarial drugs to kill adult worms, especially when given as a single dose treatment. Because these medicines kill microfilariae but not adult worms, MDA has to be given repeatedly for at least five years until natural death of adult worms. Interruptions in this treatment regimen risks repopulation of microfilariae, creating a heavy logistical burden on countries and lack of compliance when animals migrate. Additionally, current anti-filarial medicines can cause several adverse effects in patients infected with the filarial eyeworm *Loa loa*. Thus, MDA campaigns are stalled in *Loa loa*-endemic and onchocerciasis-endemic areas.

Thus, development of short-course macrofilaricidal agents would greatly enhance eradication efforts. Accordingly, there is a need in the art for new methods for treating and/or preventing diseases caused by parasitic helminths, including, but not limited to filarial worms.

BRIEF SUMMARY

The present disclosure is directed to methods for preventing and/or treating helminthiasis (i.e., a disease caused by parasitic helminths), including, but not limited to, disease caused by filarial worms. These methods comprise administering to the animal in need thereof a therapeutically effective amount of an inhibitor of UDP-glucoronosyl transferase (UGT) and/or an inhibitor of an immunoglobulin I-set domain containing protein (IgI-DCP, Bma-LAD-2).

In certain embodiments, the inhibitor of IgI-DCP is a molecule that inhibits adhesion function and/or is an inhibitor of vascular cell adhesion molecules (VCAMs), intercellular cell adhesion molecules (ICAMs), neural cell adhesion molecules (NCAMs), mucosal addressin cell adhesion molecules (MADCAMs), and/or junction adhesion molecules (JAM).

In other embodiments, the inhibitor of UGT is one or more of sulfinpyrazone, p-(di-n-propylsulphamyl)-benzoic acid (probenecid), 5,7-dihydroxyflavone (chrysin), 5-(2,4-difluorophenyl)-2-hydroxybenzoic acid (diflunisal), 2-((2,3-dimethylphenyl)amino)benzoic acid (mefenamic acid), (2R, 3R)-3,5,7-trihydroxy-2-[(2R,3R)-3-(4-hydroxy-3-methoxy-phenyl)-2-(hydroxymethyl)-2,3-dihydrobenzo[b][1,4]di-oxin-6-yl]chroman-4-one (silibinin), 5,6,7,8-tetramethoxy-2-(4-methoxyphenyl)-4H-1-benzopyran-4-one 5,6,7,8,4'-pentamethoxyflavone (tangeretin), 1-acetyl-4-(4-{[(2R,4S)-2-(2,4-dichlorophenyl)-2-(1H-imidazol-1-ylmethyl)-1,3-dioxolan-4-yl]methoxy}phenyl)piperazine (ketoconazole), 1-(butan-2-yl)-4-{4-[4-(4-{[(2R,4S)-2-(2,4-dichlorophenyl)-2-(1H-1,2,4-triazol-1-ylmethyl)-1,3-dioxolan-4-yl] methoxy}phenyl)piperazin-1-yl]phenyl}-4,5-dihydro-1H-1, 2,4-triazol-5-one (itraconazole), 5-thiazolylmethyl ((alphaS)-alpha-((1S,3S-1-hydroxy-3-((2S)-2-(3-((2-isopro-pyl-4-thiazolyl)methyl)-3-methylureido)-3-methylbu-tyramido)-4-phenylbutyl)phenethyl)carbamate (ritonavir), 5-((3,4-dimethoxyphenethyl)methylamino)-2-(3,4-dime-thoxyphenyl)-2-isopropylvaleronitrile (verapamil), (+)-di-pentene (D-limonene), 2',4',5',7'-tetrabromo-4,5,6,7-tetra-chlorofluorescein (cyanosine), bilirubin, (5α,14β,18R)-17-(cyclopropylmethyl)-18-[(1S)-1-hydroxy-1,2,2-trimethyl-propyl]-6-methoxy-18,19-dihydro-4,5-epoxy-6,14-ethe-nomorphinan-3-ol (buprenorphine), (22R,25R)-3β-hy-droxy-5α-spirostan-12-one (hecogenin), 1-napthol, 2-{[3-(trifluoromethyl)phenyl]amino}pyridine-3-carboxylic acid (niflumic acid), or 2-(2-((2,6-dichlorophenyl)amino)phenyl) acetic acid (diclofenac).

In a specific embodiment, the inhibitor of UGT is sulfinpyrazone and/or probenecid. In other embodiments, the inhibitor of UGT is an N-acyl phenylaminoalcohol residue and a uridine moiety connected by a spacer, wherein the spacer comprises a hydrocarbyl or a substituted hydro-carbyl. In another embodiment, the inhibitor of UGT and/or IgI-DCP is an antibody. The inhibitor of UGT and/or IgI-DCP is a direct inhibitor or an indirect inhibitor of UGT and/or IgI-DCP.

In certain embodiments, the helminthiasis is a filarial disease, including, but not limited to, lymphatic filariasis, river blindness, loiasis, or dirofilariasis. In some embodiments, the filarial disease is caused by an infection of one or more species of *Brugia, Wuchereria, Onchocerca, Loa*, or *Dirofilaria*. In some embodiments, the filarial disease is caused by an infection of one or more of *Brugia malayi, Brugia timori, Wuchereria bancrofti, Onchocerca volvulus, Loa loa*, or *Dirofilaria immitis*. In another particular embodiment, the filarial disease is caused by an infection of one or more species of *Dirofilaria*, such as *Dirofilaria immitis*. In other embodiments, the helminthiasis is caused by a non-filarial helminth, including, but not limited to, one or more of *Haemonchus contortus, Haemonchus placei, Haemon-chus similis*. In a particular embodiment, the helminthiasis is caused by an infection of *Haemonchus contortus*.

The infected animal may be any known animal known to be susceptible to filarial infection, such as, but not limited to, a human, a ruminant animal or other livestock animal, or a companion animal, including but not limited to a sheep, a goat, a cow, a llama, a camel, a horse, a mule, a pig, a bird, a rabbit, a deer, an elk, or a giraffe, or companion animals such as a dog or a cat.

In certain embodiments, the method further comprises administering to the animal an anthelmintic drug in addition to the inhibitor of IgI-DCP or the inhibitor of UGT, such as a first-line anthelmintic drug. In certain embodiments, the anthelmintic drug is albendazole.

BRIEF DESCRIPTION OF THE DRAWINGS

The accompanying drawings, which are incorporated in and constitute a part of this specification, illustrate certain embodiments, and together with the written description, serve to explain certain principles of the constructs and methods disclosed herein.

(FIG. 3A) After 24 hours of UGT siRNA incubation, UGT protein expression was evaluated by Western blot (FIG. 3B) or Western blot bands quantitated and normalized in comparison to R-actin expression (FIG. 3C).

FIG. 6A shows that the combination of sulfinpyrazone with albendazole caused a synergistic reduction in motility over the course of 8 days (FIG. 6A, ALB is albendazole, SFZ is sulfinpyrazone). Likewise, female adult *B. malayi* worms were incubated in vitro with either probenecid, albendazole, or a combination of probenecid and albendazole together. FIG. 6B shows that the combination of probenecid and albendazole caused a synergistic reduction in motility over the course of 8 days (FIG. 6B, ALB is albendazole, PRB is probenecid).

(FIG. 8A) After 24 hours of Bma-LAD-2 siRNA incubation, Bma-LAD-2 protein expression was evaluated by Western blot (FIG. 8B) or Western blot bands quantitated and normalized in comparison to β-actin expression (FIG. 8C).

DEFINITIONS

Figure 1:
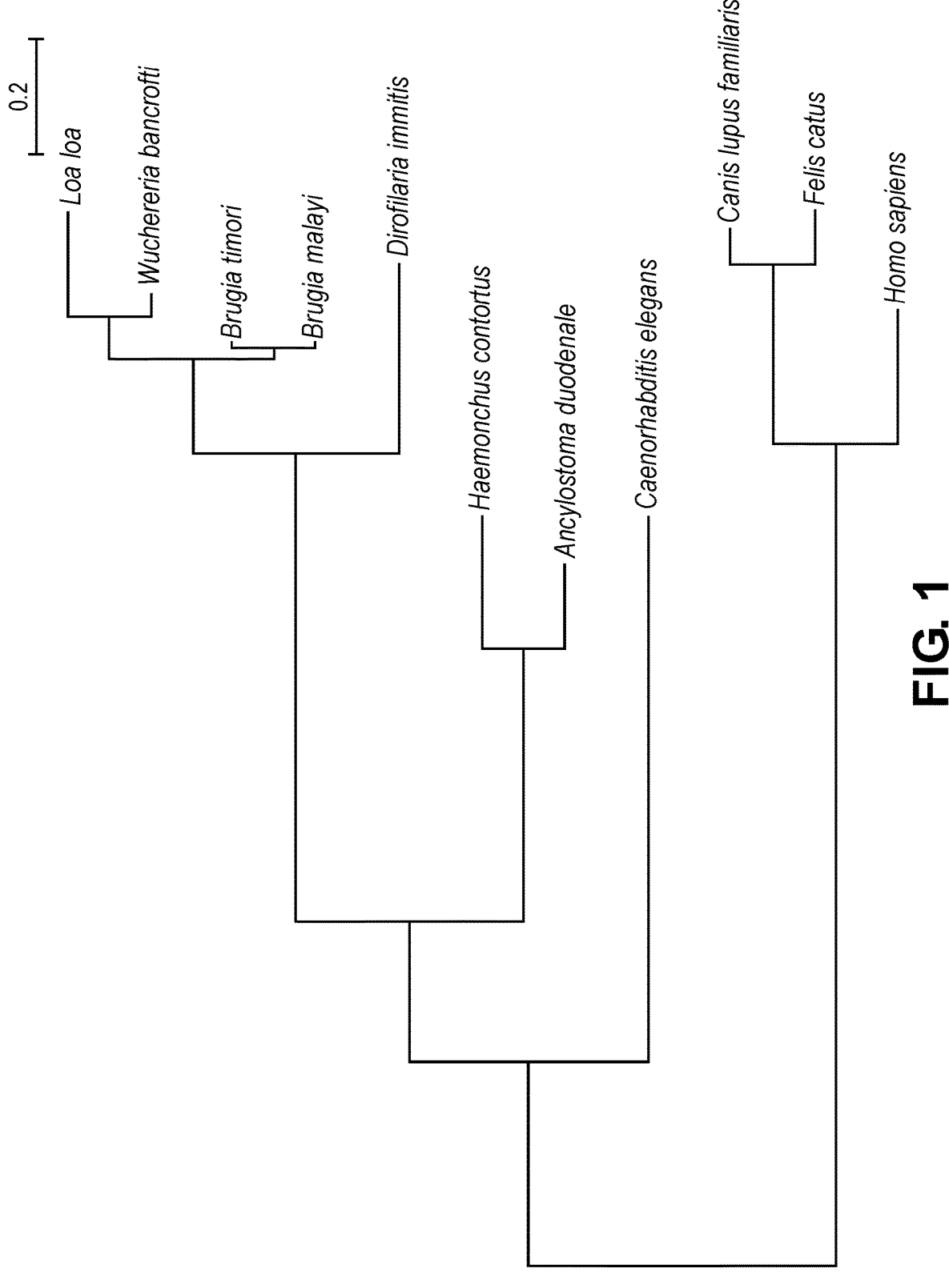
FIG. 1 depicts a phylogenetic tree comparing UGT sequences from various selected helminths. Based on the *B. malayi* cDNA sequence, there is a high level of relatedness to other filarial species for UGT with low homology to cats, dogs, and humans. The phylogenetic tree is based on sequence homology and generated using MUltiple Sequence Comparison by Log-Expectation (MUSCLE) performed by software SeaView. (See, Gouy et al., *Mol. Biol. Evol.,* 27(2):221-224, 2010).

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls Unless otherwise specified, all percentages and amounts expressed herein and elsewhere in the specification should be understood to refer to percentages by weight. The amounts given are based on the active weight of the material.

The term "polypeptide" as used herein refers to a polymer of amino acid residues. This term is used interchangeably with the term "protein."

In some embodiments, the present polypeptides are obtained or derived from a filarial worm. A "filarial worm" as used herein refers to parasitic nematodes of the Metazoa kingdom including the superfamily filarioidea, family Filari-idae. Filarial worms include, but are not limited to, species belonging to the genera *Brugia*, such *Brugia malayi* and *Brugia timori*, *Wuchereria*, such as *Wuchereria bancrofti*, *Onchocerca*, such as *Onchocerca volvulus*, and *Loa*, such as *Loa loa*, *Dirofilaria*, such as *Dirofilaria immitis* and *Dirofilaria vivaparus*.

The phrase "derived from" encompasses "originating from," "obtained from," or "isolated from" a parent poly-peptide.

The terms "isolated" or "purified" or "biologically pure" refer to material that is substantially or essentially free from components that normally accompany it as found in its native state. Purity and homogeneity are typically deter-mined using analytical chemistry techniques such as poly-acrylamide gel electrophoresis or high-performance liquid chromatography (HPLC). A protein that is the predominant species present in a preparation is considered to be substan-tially purified. The term "purified" denotes that a protein gives rise to essentially one band in an electrophoretic gel. For example, it means that the protein is at least 85% pure, such as at least 95% pure or at least 99% pure.

As used herein, the term "immunogen" or "immuno-genic" refers to any substrate that elicits an immune response in a host, e.g., at least an antibody response. An "immunogenic composition" includes at least one isolated polypeptide with or without a pharmaceutically acceptable carrier, such as an adjuvant. The immunogenic compositions disclosed herein may or may not be immunoprotective or therapeutic. Accordingly, the term "immunogenic" is not intended to be limited to vaccines.

As used herein, "homology" refers to the percent sequence identity between two polypeptide moieties. Two polypeptide sequences "display substantial homology" or are "substantially homologous" to each other when the sequences exhibit at least about 41%, such as at least about 75%, more typically at least about 80%-85%, even more typically at least about 90%, and most typically at least about 95%, 96%, 97%, 98%, 99% or more sequence identity over a defined length of the molecules. As used herein, "substantially homologous" also refers to sequences show-ing complete (100%) sequence identity to the polypeptide sequences. In some embodiments, a sequence is not sub-stantially homologous when it exhibits a sequence identity of 40% or less sequence identity.

"Sequence identity" as used herein refers to a relationship between two or more polypeptide sequences, namely a reference polypeptide sequence and a given polypeptide sequence to be compared with the reference polypeptide sequence. Sequence identity is determined by comparing the given polypeptide sequence to the reference polypeptide sequence after the polypeptide sequences have been opti-mally aligned to produce the highest degree of sequence similarity, as determined by the match between strings of such sequences, with gaps introduced if necessary. Upon such alignment, sequence identity is ascertained on a posi-tion-by-position basis, e.g., the sequences are "identical" at a particular position if at that position, the amino acid residues are identical. The total number of such position identities is then divided by the total number of residues in the reference sequence to give % sequence identity.

Sequence identity can be readily calculated by known methods, including but not limited to, those described in Computational Molecular Biology, Lesk, A. N., ed., Oxford University Press, New York (1988), Biocomputing: Infor-matics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM *J. Applied Math.*, 48: 1073 (1988); the teachings of which are incorporated herein by reference.

Methods to determine sequence identity are codified in publicly available computer programs which determine sequence identity between given sequences. Examples of such programs include, but are not limited to, the GCG program package (Devereux, J., et al., *Nucleic Acids Research*, 12(1):387 (1984), BLASTP, BLASTN and BLASTX (Altschul, S. F. et al., J. *Mol. Biol.*, 215:403-410 (1990)). The BLAST programs are publicly available from NCBI and other sources (BLAST Manual, Altschul, S. et al., NCVI NLM NIH Bethesda, Md. 20894, Altschul, S. F. et al., J. *Mol. Biol.*, 215:403-410 (1990), the teachings of which are incorporated herein by reference). These programs opti-mally align sequences using default gap weights in order to produce the highest level of sequence identity between the given and reference sequences.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein "preventing" refers to the administration of a therapeutically effective amount of a UGT or IgI-DCP inhibitor to an animal to protect the animal from developing a helminth disease. Thus, the term "preventing" when used in the context of a disease or disease condition means prophylactic administration of a composition that stops or otherwise delays the onset of a pathological hallmark or symptom of a disease or disorder.

As used herein "treating" refers to the administration of a therapeutically effective amount of a UGT or IgI-DCP inhibitor to an animal *Brugia malayi, Wuchereria bancrofti, Onchocerca volvulus, Loa loa, Haemonchus contortus*, or *Dirofilaria immitis*, where the purpose is to cure, heal, alleviate, relieve, alter, remedy, mitigate, ameliorate, improve, or otherwise affect the condition or the symptoms associated with the filarial infection.

In particular aspects of the disclosure, a "therapeutically effective amount" refers to an amount of a compound, such as a UGT or IgI-DCP inhibitor, of the present disclosure that when administered to an animal brings about a positive therapeutic response with respect to the helminth infection. For example, a positive therapeutic response with respect to treating diseases or conditions associated with a helminth infection includes ameliorating the symptoms of the disease. A positive therapeutic response with respect to preventing a condition associated with a helminth infection includes, for example, the halt of reproduction or appearance of adult worms.

An "inhibitor" as used herein means a molecule or peptide that reduces the activity of its target. For instance, an inhibitor of UGT is a molecule that when administered to an animal in need thereof, reduces or fully stops the activity of the UGT, i.e. stops transfer of glucuronate (glucuronic acid) catalyzed by UGT. Likewise, an inhibitor of an IgI-DCP is a molecule that when administered to an animal in need thereof reduces or fully stops the ability of the IgI-DCP from interacting with cognate proteins through its I-set domain, or otherwise reduces or stops the function of the I-set domain containing protein. In one embodiment, an inhibitor is an antibody specific for UGT or IgI-DCP.

The term "antibody" as used in this disclosure refers to an immunoglobulin or an antigen-binding fragment thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

DETAILED DESCRIPTION

It is to be understood that the following detailed description is provided to give the reader a fuller understanding of certain embodiments, features, and details of aspects of the invention, and should not be interpreted as a limitation of the scope of the invention.

The present disclosure provides new methods and compositions for treating diseases or disorders caused by helminth infections. Typically, the disease is a filarial disease, however, the methods can also be used to treat or prevent other helminth diseases. These methods comprise administering to an animal a therapeutically effective amount of an inhibitor of UDP-glucoronosyl transferase (UGT) and/or an inhibitor of an immunoglobulin I-set domain containing protein (IgI-DCP, Bma-LAD-2). As demonstrated in the examples through siRNA experiments, of nine tested genes, including Bma-fukutin, Bma-serpin, Bma-shtk, Bma-reprolysin, Bma-peptidase, Bma-egf-like-02820, Bma-egflike-48010, Bma-LAD-2, and Bma-iUGT, only the UGT and the IgI-DCP were found to be essential proteins for adult *B. malayi* survival and, thus, present attractive targets for killing parasitic helminths. The examples further demonstrate that UGT inhibitors, such as sulfinpyrazone and probenecid, exhibit potent cytotoxic activity against adult helminths with minimal cytotoxic activity against microfilariae. The rapid killing of microfilariae by current antifilarial therapeutics such as diethylcarbamazine (DEC) and ivermectin (IVM), can lead to severe adverse outcomes. Thus, the present disclosure establishes that inhibitors against these essential helminth proteins represent a new class of improved therapeutic agents for treating and/or preventing diseases or disorders caused parasitic helminths, including, but not limited to filarial worms.

Filarial Diseases

Filariasis is a parasitic disease caused by an infection with roundworms of the Filarioidea type. The Filarioidea are a superfamily of highly specialized parasitic nematodes. Filariasis causative infectious agents, filariae, are most commonly spread by blood-feeding black flies and mosquitoes. Filariasis is a disease categorized in the family of helminthiases. Filariae are tissue-invasive roundworms transmitted by arthropods. There are eight known pathogenic human filariae that are categorized into three groups. One group is lymphatic filariasis caused by worms such as *Wucherieria bancrofti* and *Brugia malayi*, which cause lymphatic filariasis (elephantiasis) and target the lymphatic system including the lymph nodes. A second group is cutaneous and subcutaneous filariasis, which is caused by infection with *Onchocerca volvulus* (river blindness), *Loa loa* (eye worm), *Mansonella streptocerca*, and *Onchocerca volvulus*, that occupy the cutaneous and subcutaneous (fat) layers of skin in hosts. The third group is serous cavity filariasis, which is caused by infection of *Mansonella* perstans and *Mansonella ozzardi*, that occupy the serous cavity of the abdomen, and include the species *Dirofilaria immitis* (dog heartworm), which rarely infects humans.

*Wucherieria bancrofti* and *Brugia malayi* infect over 67 million people, causing hydrocele in 20 million and lymphedema in 17 million. *O. volvulus* infects 16 to 30 million people and causes itching and blindness. *Dirofilaria immitis* is a vector-borne filarial parasite that infects over 200,000 domestic dogs and cats throughout the United States, especially in the southeast region. Infection can lead to pulmonary arterial occlusion, hypotension, and/or congestive heart failure. In order to prevent infection, pet owners in highly endemic states ae advised to administer antifilarial medications.

Over 70 million people are infected worldwide with lymphatic filariasis (LF), a debilitating disease characterized by severe lymphedema, elephantiasis, and hydrocele (Ramaiah et al., *PLoS Negl Trop Dis.*, 2014; 8(11):e3319). This is caused by the parasitic nematodes *Wuchereria bancroft, Brugia malayi*, and *Brugia timori*. Currently, efforts to eliminate this disease have been spearheaded by the Global Programme to Eliminate Lymphatic Filariasis. (Global Programme to Eliminate Lymphatic Filariasis: World Health Organization; 2016 [cited 2016 May 2], available from: www.who.int/lymphatic_filariasis/disease/en/). While this campaign has greatly reduced the overall prevalence of the disease, new strategies and therapeutics are needed in order to eliminate LF. (Hoerauf et al., *Clin Microbiol Infect.*, 2011; 17(7):977-85; Rebollo et al., *Trends Parasitol.*, 2017; 33(2): 83-92; Bockarie et al., *Curr Opin Infect Dis.*, 2010; 23(6): 617-20).

Other Helminth Diseases

Filarial worms are not the only parasitic helminths. As discussed above, three major categories of parasitic helminths are recognized: the Acanthocephalins (thorny-headed worms), the Nemathelminthes (nematodes) and the Platy-helminthes (flatworms), which are subdivided into the Cestoda (tapeworms) and the Trematoda (flukes).

Nematodes are divided into two classes based on the presence or absence of special chemoreceptors known as phasmids: Secernentea (Phasmidea) and Adenophorea (Aphasmidea). The main parasitic nematodes infecting humans and domestic animals include one aphasmid order (Trichocephalida; also called whip-worms) and six phasmid orders (Oxyurida (also called pin-worms), Ascaridida (also called roundworms), Strongylida (also called hookworms), Rhabditida (also called threadworms), Camallanida (also called guinea worms, and Spirurida (also called filarial worms)).

Thus, in certain embodiments, the methods described herein are used to treat prevent an infection caused by a non-filarial helminth. In one embodiment, the non-filarial helminth is a thorny-headed worm. In one embodiment, the non-filarial helminth is a tapeworm. In one embodiment, the non-filarial helminth is a fluke. In another embodiment, the non-filarial helminth is a nematode selected from a Trichocephalida, an Oxyurida, an Ascaridida, a Strongylida, a Rhabditida, or a Camallanida.

In certain embodiments, the non-filarial helminth is a Strongylida, such as Strongyloides stercoralis, or an Enterobius, such as Enterobius vermicularis (pinworm), and those from the Haemonchus genus. Haemonchus contortus, also known as barber's pole worm, is a highly pathogenic roundworm that can cause a disease called haemonchosis, which is particularly prevalent and costly in ruminants such as the goat and sheep population. Haemonchus infection leads to anemia, oedema, failure to gain weight, and bottle-jaw (sub-mandibular oedema), and death in the infected animal. Haemonchosis is commonly found in tropical and temperate farming areas, where Haemonchus contortus can lay up to 5,000 to 15,000 eggs per day in the infected host animal. (See, Emery et al., Int., J. Parasit., 46:755-769, 2016). In particularly infected or susceptible populations, prophylactic anthelmintic treatments are commonly employed. A commercial vaccine is available against haemonchosis but resistant populations continue to stifle attempts to eradicate the disease. (Id.). Infections from helminths other than Haemonchus also cause losses to livestock and domesticated animals, as well as serious illnesses in humans, including, but not limited to, Necator, such as Necator americanus, Oesophagostomus, Trichostrongylus, Shistosoma, Trichuris, such as Trichuris trichiura, Ancylostoma, such as Ancylostoma duodenale, Fasciola, such as Fasciola hepatica, or Gnathostoma, such as Gnathostoma spinigerum.

Uridine 5'-Diphospho-Glucuronosyltransferase (UGT)

UDP-glucuronosyltransferases (UGT) are Phase II enzymes important for detoxification of xenobiotics and homeostasis of endogenous molecules. (Rowland et al., Int. J. Biochem. Cell Biol., 2013; 45(6):1121-32). Specifically, these phase II enzymes increase the solubility of hydrophobic molecules by transferring sugar moieties such as glucuronic acid onto hydrophobic molecules. Because glucuronic acid is negatively charged at physiological pH, anion efflux pumps are able to then transport these molecules outside the cell. (Guillemette et al., Pharmacogenomics J., 2003; 3(3):136-58).

While UGTs in helminths have not been studied extensively, there is evidence from intestinal helminths to suggest that these enzymes play a critical role in drug resistance. (Vokral et al., Parasitology, 2012; 139(10):1309-16; Vokral et al., Vet. Parasitol., 2013; 196(3-4):373-81; Kotze et al., Antimicrob. Agents Chemother., 2014; 58(12):7475-83). In C. elegans, studies demonstrated that RNAi of detoxification enzymes resulted in lethality, sluggish movement, or impaired growth. (Simmer et al., PLoS Biol., 2003; 1(1): E12; Kamath et al., Nature, 2003; 421(6920):231-7; Maeda et al., Curr. Biol., 2001; 11(3):171-6). Past studies in mice and rats demonstrated that UDP-glucoronosyl transferases were critical for protection against free radicals, which if left uncheck could mediate damage to DNA, lipid membranes, and amino acids. (Attia et al., Oxid. Med. Cell. Longev., 3(4):238-53, 2010; Kim et al., Cancer Res., 56(7):1526-32, 1996; Kim et al., J. Pharmacol. Exp. Ther., 1997; 280(1): 200-9; Barbier et al., J. Biol. Chem., 2003; 278(16):13975-83). In addition, one study showed that glycosylation by phase II enzymes was important for the detoxification albendazole in C. elegans. (Laing et al., Biochem. J., 2010; 432(3):505-14).

Interestingly, it should be noted that the Brugia intestinal UGT is predicted by InterPro database to be localized to the plasma membrane, which would be an unusual location for this family of enzymes that are typically found in the endoplasmic reticulum. (See, Apweiler et al., Nuc. Acids Res., 29(1):37-40, 2001). The prediction software also determined that this protein has a large extracellular domain, which potentially makes it readily accessible to drugs or antibodies.

It has been reported that Bma-iUGT (Bm17378) is a specific intestinal protein of B. malayi adult worms. (Morris et al., PLoS Negl. Trop. Dis., 2015; 9(9):e0004054). A Basic Local Alignment Search Tool (BLAST) analysis was performed to compare the sequence identity of Bma-iUGT across orthologs from other helminths. (Table 1). The query sequence of Bma-iUGT used to determine percent sequence identity is gene Bm1_13480 (UniProtKB database, A80I8_BRUMA).

TABLE 1

| Species | Percent Identity | Residue Numbers |
|---|---|---|
| H. sapiens Host: human | 27 | 35-509 |
| W. bancrofti | 95 | 1-425 |
| O. volvulus | 29 | 214-293 |
| L. loa | 81 | 1-423 |
| N. americanus | 33 | 21-523 |
| A. duodenale | 38 | 21-491 |
| Schistosoma | 26 | 87-206 |
| G. spinigerum | 52 | 162-184 |
| T. trichiura Host: animal other than human | 27 | 11-509 |
| F. hepatica | 56 | 176-191 |
| Trichostrongyl | 30 | 482-539 |
| H. contortus | 40 | 21-519 |
| Oesophagosto | 38 | 21-535 |
| D. viviparus | 35 | 19-514 |
| D. immitis | 72 | 155-502 |

As shown in Table 1, the peptide sequence for Bma-iUGT shares high sequence identity with the UGT orthologs from certain filarial helminths. For example, W. bancrofti, L. loa, and D. immitis share 95, 81, and 7200 identity, respectively. On the other hand, other filarial and non-filarial helminths share lower percent identities, ranging from 26% to 56%. The human UGT ortholog shares 27% identity. (Table 1). Notwithstanding this low percent identity to human UGT, the examples show that UGT inhibitors that are effective in humans are also effective against *Brugia malayi*, suggesting that helminth homologs having as low as 27% identity to Bma-iUGT are effective targets for UGT inhibitors.

Predictive analysis using the InterPro database revealed that the protein contains a large luminally-expressed domain likely accessible to small molecules or ingested antibodies. A phylogenetic tree is provided in FIG. 1 that was generated by first aligning the Bma-iUGT peptide sequences using MUltiple Sequence Comparison by Log-Expectation (MUSCLE) and then creating a tree based on efficient maximum-likelihood estimation method by the LG model. A high level of relatedness between Bma-iUGT and helminth orthologs, including *D. immitis* is found. Importantly, there is significant evolutionary distance between this UGT and orthologs in humans, cats, and dogs.

Thus, phylogenetics analyses suggest that Bma-iUGT is also essential in *W. bancrofti* and *B. timori*, as well as other helminths, given the overall homology shared between these species and *B. malayi*. Additionally, there is a high level of sequence homology between the *B. malayi* intestinal UGT and the orthologs found in *D. immitis* and *Loa loa*. In view of the data provided in this application, the sequence homology shared across the filarial UGT orthologs and other non-filarial helminths indicate that UGT may also serve as an effective therapeutics target in other filarial and non-filarial helminths.

Previous studies have demonstrated that Bma-iUGT is not expressed in all the larval stages. Li et al. observed that Bma-iugt transcript expression occurred only in the adult female and male worm stage as well as the larval stage 3. (*BMC Genomics*, 2012; 13:184; see also, Attout et al., *Parasitology*, 2005; 130(Pt 4):421-8). Bma-iUGT protein expression was determined to be specific to these stages as well. (Bennuru et al., *Proc. Natl. Acad. Sci. USA*, 2011; 108(23):9649-54).

*B. malayi* UGT has the following peptide sequence (gi 170577850, XM_001894126.1, XP_001894161.1):

```
                                     (SEQ ID NO: 1)
MYHAEWYLASLIIIFHASQNDSYKILVYNPRFGKSHTKFLGSIADTLVN

AGHNVTEFAPVLFEFSDSTGSKLAKTVKIDADPEISKIMNVEIFAQDAW

KRNQQSIFSLISVMKRMSDALLKNCEFQLKQEKIMQELKSEKFDLAIFE

FNQCFAGIIELLRIPAHIVVSPTALFEYAIECFGIPNIPSYIPSLLTQY

TDKMTYLQRLKNLIITILTTKLLDNHTIRCQALFRRLYGDQFIDLKEKL

AQVTYVLTNTDPLFHISRPTIHKMLELGGLALPKPQPLSKEWIAVMNKR

KAVVLVSFGTVTLSCWMPNETKQALLDAFDSFPNVTFIWKYEKDEHLIA

EGRPNVITSKWLPQSDLLAHKNLIAFLTHGGMNSITETLNRGKPIVVVP

LFGDQMQNAVLVQRLGLGIKLSLSELAIKEKIKNAIYNIIYDKSYAQKV

ERLSKMMAKKPNQAEEQLIKHVEFAAEFGQIANFDPYGRKMSFVSYYML

DIIIPFIILIFFIITIICYLIIRLFRKLFHKAVICNNNNSIITKVKKN
```

Likewise, the mRNA sequence is as follows (lowercase indicates untranslated regions, UTR):

```
                                     (SEQ ID NO: 2)
gaaagtaatcgaagtatttggtgctgaaatacaATGTATCATGCTGAGT

GGTATTTGGCTTCACTCATTATTATATTTCATGCATCACAGAATGATTC
```

```
ATATAAAATATTGGTATATAATCCACGTTTTGGTAAAAGTCACACCAAA

TTTTTGGGTTCAATCGCTGATACATTGGTTAATGCCGGGCATAATGTAA

CCGAGTTTGCTCCTGTACTTTTTGAATTTTCCGATTCCACTGGTTCTAA

ATTGGCTAAAACAGTAAAAATAGACGCTGATCCGGAAATATCGAAAATA

ATGAACGTAGAAATTTTTGCTCAAGATGCATGGAAACGAAATCAGCAAT

CCATTTTCTCATTGATTTCGGTTATGAAACGAATGTCGGATGCTCTTCT

GAAGAATTGTGAGTTTCAACTAAAGCAGGAAAAAATAATGCAAGAATTG

AAATCTGAAAAGTTTGACTTAGCTATCTTCGAATTTAACCAATGCTTTG

CCGGAATAATTGAATTGCTTCGTATACCGGCTCATATTGTCGTTAGTCC

TACTGCTCTATTTGAATATGCCATAGAATGTTTTGGTATACCAAATATT

CCTAGCTATATTCCAAGTTTGCTTACACAGTATACTGATAAGATGACAT

ATTTACAACGGCTGAAGAATCTCATCATAACAATTTTAACGACTAAATT

GCTGGATAATCATACAATAAGATGTCAAGCCTTGTTTCGACGACTTTAC

GGCGATCAATTTATCGATTTGAAAGAAAAGTTAGCTCAAGTGACATATG

TTCTCACAAATACTGATCCACTTTTTCACATCTCAAGGCCAACTATTCA

CAAAATGTTGGAACTTGGTGGTCTTGCCTTACCAAAACCGCAACCGCTA

AGTAAAGAATGGATTGCAGTGATGAATAAACGGAAAGCGGTAGTGCTTG

TATCATTCGGCACCGTTACACTGAGTTGTTGGATGCCTAACGAAACTAA

GCAAGCACTTCTAGATGCATTCGATAGTTTTCCCAATGTGACATTTATC

TGGAAGTATGAAAAAGATGAGCATTTAATCGCTGAGGGACGTCCAAACG

TGATTACGTCAAAATGGCTTCCACAATCTGATTTGTTAGCACATAAAAA

TTTGATAGCATTTTTGACGCATGGTGGTATGAATAGCATAACGGAAACT

TTGAATCGTGGAAAACCTATTGTTGTGGTACCGCTATTTGGTGATCAGA

TGCAGAATGCTGTATTAGTTCAACGATTAGGTCTTGGTATCAAATTATC

CCTTTCGGAACTTGCGATAAAAGAAAAAATAAAAAATGCAATTTATAAT

ATCATCTATGACAAAAGTTATGCCCAAAAAGTTGAAAGATTATCAAAAA

TGATGGCAAAAAAGCCTAATCAAGCTGAGGAACAACTCATTAAGCATGT

TGAATTTGCTGCAGAATTTGGTCAAATAGCGAATTTCGACCCATACGGC

AGAAAAATGTCATTTGTATCTTATTATATGCTTGATATTATCATTCCTT

TTATAATACTTATATTCTTTATCATTACAATCATTTGTTACCTTATCAT

TAGACTATTCAGAAAATTATTCCACAAAGCTGTTATCTGTAATAATAAT

AATAGTATTATAACAAAGGTGAAAAAAAATTAA
```

Immunoglobulin I-Set Domain Containing Protein (IgI-DCP, Bma-LAD-2)

Bma-LAD-2 is the *B. malayi* immunoglobulin (Ig) intermediate-set (I-set) domain containing protein (IgI-DCP) and, therefore, belongs to the functionally diverse Ig superfamily (IgSF). The Ig domain is the basic structural unit of the superfamily and consists of two sandwiched antiparallel beta sheets. (Buck C A, Seminars in *Cell Biology*, 1992, 3(3):179-88). Proteins in the IgSF are classified based on the structure of their Ig domain and given a set designation of variable (V), constant 1 (C1), constant 2 (C2), or intermediate (I). (Smith et al., *J. Mol. Biol.*, 1997; 274(4):530-45). Ig I-set domains are similar to V-set domains but have a shorter distance between the invariant cysteine residues.

IntroPro analysis predicts that Bma-LAD-2 has 6 Ig domains spanning from amino acid position 24 to 602. A Basic Local Alignment Search Tool (BLAST) analysis was performed to compare the sequence identity of Bma-LAD-2 across orthologs from other helminths. (Table 2). The query sequence of Bma-LAD-2 used to determine percent sequence identity is gene Bm1_39630 (UniProtKB database, A0A0H5SCW1_BRUMA).

TABLE 2

| Species | Percent Identity | Residue Numbers |
|---|---|---|
| *H. sapiens* Host: human | 28 | 45-1170 |
| *W. bancrofti* | 97 | 628-1171 |
| *O. volvulus* | 87 | 26-1171 |
| *L. loa* | 89 | 1-1171 |
| *N. americanus* | 48 | 20-1181 |
| *A. duodenale* | 45 | 531-914 |
| *Schistosoma* | 28 | 63-858 |
| *T. trichiura* Host: animal other than human | 43 | 23-1179 |
| *F. hepatica* | 32 | 93-381 |
| *H. contortus* | 50 | 1-1107 |
| *Oesophagosto* | 55 | 235-570 |
| *D. viviparus* | 38 | 365-1117 |
| *D. immitis* | 82 | 1-1117 |

The data in Table 2 indicate that the peptide sequence for Bma-LAD-2 shares high sequence identity with the IgI-DCP orthologs from certain filarial helminths. For example, *W. bancrofti*, *L. loa*, and *O. volvulus* share 97, 87, and 79% identity, respectively. On the other hand, other filarial and non-filarial helminths share lower percent identities, ranging from 28% to 55%. The human IgI-DCP ortholog shares 28% identity. (Table 2).

Further, based on homology to its ortholog in *C. elegans* (LAD-2, L1 adhesion), Bma-LAD-2 is predicted to be an L1 cell adhesion molecule (L1CAM). L1CAMs are single transmembrane proteins that can participate in homophilic and heterophilic interactions. (Kiefel et al., *Cell Adh Migr.*, 2012; 6(4):374-84). The cytoplasmic tail of L1CAMs has multiple consensus-binding sites which allow for interaction with various cytoskeleton linkers proteins such as ankyrin, spectrin, and ERM. (Hartsock et al., *Biochim Biophys Acta*, 2008; 1778(3):660-9; Takahashi et al., *Journal of Cell Biology*, 1999; 145(3):539-49). Furthermore, the cytoplasmic tail of L1CAMs has phosphorylation sites indicating a possible role in signal transduction. (Kiefel et al., *Cell Adh Migr.*, 2012; 6(4):374-84; Chen et al., *Dev Dyn.*, 2010; 239(5):1490-501; Hoffmann et al., *Dev Biol.*, 2010; 339(2): 268-79).

Interestingly in *C. elegans*, LAD-2 is critical in guiding axon migration and does not appear to be critical for the establishment or maintenance of the intestinal epithelium. (Wang et al., *J Cell Biol.*, 2008; 180(1):233-46; Lynch et al., *Front Biosci.* (Landmark Ed), 2009; 14:1414-32). However, LAD-1, another L CAM, has been shown to co-localize with apical junction molecules. In nematodes, cell adhesion molecules (CAMs) assemble to form two major types of apical junctions: the cadherin catenin complex (CCC) and the DLG-1/AJM-1 complex (DAC). (Hartsock et al., *Biochim Biophys Acta*, 2008; 1778(3):660-9; Lynch et al., *Front Biosci.* (Landmark Ed), 2009; 14:1414-32). In *C. elegans*, it has been shown that that the CCC is not essential for cell adhesion. (Costa et al., *J Cell Biol.*, 1998; 141(1):297-308). This is surprising given the critical role of cadherins in cellular adhesion for most other eukaryotes. Researchers have suggested that LAD-1 may act as a redundant adhesion system thereby mitigating the loss of the CCC. Indeed, embryos expressing dominant-negative LAD-1 have altered cell morphology and position indicating a role in cellular adhesion. (Wang et al., *Dev Biol.*, 2005; 284(2):273-91; Dubreuil R R, *J Membr Biol.*, 2006; 211(3):151-61; Weiss et al., *J Cell Biol.*, 1998; 141(3):755-64).

In addition, it has been suggested that LAD-1 interacts with the DAC, located basal to the CCC. (Chen et al., *Dev Dyn.*, 2010; 239(5):1490-501; Hoffmann et al., *Dev Biol.*, 2010; 339(2):268-79; Lynch et al., *Front Biosci.* (Landmark Ed), 2009; 14:1414-32; Carberry et al., *Development*, 2012; 139(10):1851-62). This complex is characterized by the presence of two membrane proteins, a *Drosophila* discs large homologue (DLG-1) and apical junction molecule (AJM-1). In *C. elegans*, it has been shown that DLG-1, a membrane-associated guanylate kinase, interacts with AJM-1, a coiled-coiled protein, to maintain localization of junction molecules, act as paracellular gates, and regulate cell proliferation. (Lynch et al., *Front Biosci.* (Landmark Ed), 2009; 14:1414-32; Koppen et al., *Nat Cell Biol.*, 2001; 3(11):983-91). In *C. elegans*, RNAi of DLG-1 has been shown to be embryonically lethal while mutagenesis of ajm-1 leads to arrested development at the 2-3-fold stage of elongation. (Koppen et al., *Nat Cell Biol.*, 2001; 3(11):983-91; McMahon et al., *J Cell Sci.*, 2001; 114(Pt 12):2265-77). These molecules are thought to co-localize to the membrane by interactions with a transmembrane protein. One such protein thought to be membrane anchor for the DAC is LAD-1. However, studies have failed to demonstrate the existence of this interaction though loss of the DAC reportedly disturbs the junctional localization of phosphorylated LAD-1. (Carberry et al., *Development*, 2012; 139(10):1851-62; Bernadskaya et al., *Mol Biol Cell*, 2011; 22(16):2886-99).

Figure 2:
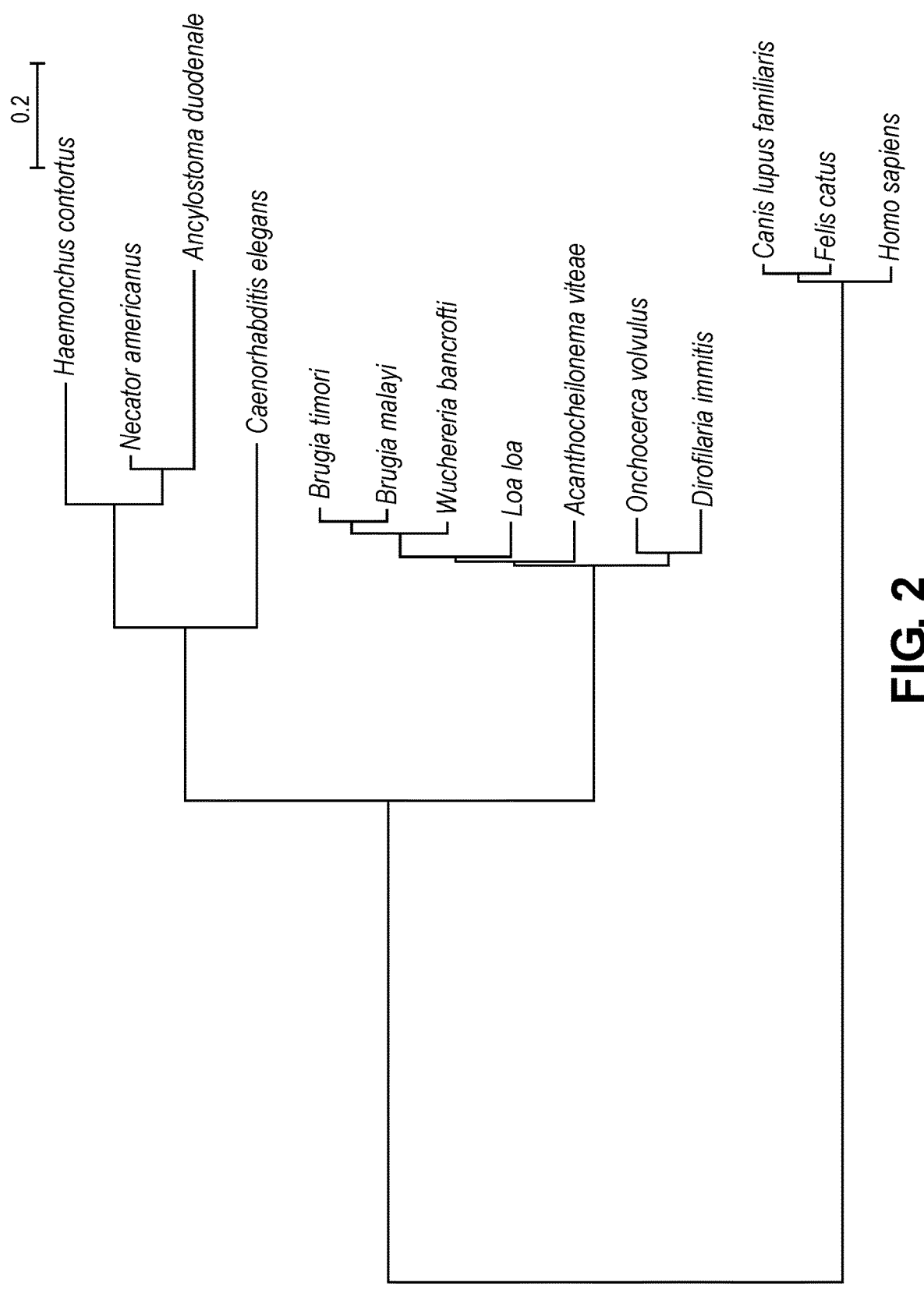
FIG. 2 depicts a phylogenetic tree comparing the cDNA of Bma-LAD-2 sequences from various selected helminths. Based on the *B. malayi* cDNA sequence, there is a high level of relatedness to other filarial species for Bma-LAD-2 with low homology to cats, dogs, and humans. The phylogenetic tree is based on sequence homology and generated using MUSCLE, using the maximum likelihood method, as in FIG. 1.

Bma-LAD-2 is phylogenetically related to orthologs found in other helminths. Bma-LAD-2 has previously been shown to be a protein localized to the gut of adult *B. malayi* worms and to have a high predicted sequence homology with other filarial orthologs. (Morris et al., *PLoS Negl Trop Dis.*, 2015; 9(9):e0004054). A phylogenetic tree is provided in FIG. 2 to view the level of evolutionary relatedness between the Bma-LAD-2 and orthologs from other helminths. The phylogenetic tree includes analysis of orthologs found in helminths such as *Ancylostoma duodenale* (hookworm) and *Haemonchus contortus* (barber pole worm) as well as outlier groups for the phylogenetic tree that includes dogs, humans, and cats. These species are expected to have a significantly distant relation to Bma-LAD-2 given the low predicted sequence homology between them. The tree (FIG. 2) was constructed based on the likelihood estimation method for the LG model using aligned sequences by MUtiple Sequence Comparison by Log-Expectation (MUSCLE).

The phylogenetic tree indicates that there is a close phylogenetic relation between Bma-LAD-2 and orthologs found in other helminths. There is a degree of relatedness between Bma-LAD-2 and orthologs of intestinal helminths. Furthermore, the large phylogenetic distance to orthologs in humans, dogs, and cats suggests that targeting this protein would only effect helminths with little risk to the host.

Bma-LAD-2 is expressed throughout the lifecycle of *B. malayi* adult worms. Based on data obtained in a study evaluating the proteome of different life cycle states (Bennuru et al., *Proc Natl Acad Sci USA*, 2011; 108(23):9649-54), Bma-LAD-2 is found to be expressed during microfilariae, L3, and in both genders of adult worms. The study matched 3 unique peptides to Bma-LAD-2 from microfilariae, 1 from the L3 stage, 2 from adult females, and 1 from adult males. The similar spectra values for each sample indicates fairly consistent expression of Bma-LAD-2 across the larval stages.

Based on these facts, it is reasonable to expect that any therapeutics developed against Bma-LAD-2 would also be effective in at least *W. bancrofti, B. timori, Loa loa, Onchocerca volvulus*, and *Dirofilaria immitis* due to high overall relatedness between these filaria species. In addition, Bma-LAD-2 shares significant homology with other helminths, suggesting that a therapeutic or vaccine developed against this protein may be effective against other helminth (e.g., filarial) infections.

The peptide sequence of Bma-LAD-2 is as follows (gi 170589238, XM_001899346.1, XP_001899346.1):

```
                                      (SEQ ID NO: 3)
MITLSILWCSLFQFIAFSRTLGPPKLDPENGGEVWFQVNSTGIARGKFI

LPCYATGNPETYEWFKDGEKLKVDGDRIAWEKQFQSGTIIINDARDGDQ

GYYQCHASNIFGIAVSNKFHVQIGVLDHFVPRGVRRLIVDEGQSLSIRC

DIPYGVPKPSVFWLYRDTQRTNMIETIRYKHIAVDTEGTLHFTAVKKHD

GRQNLIYQCAVTSPVLRGEYRAGNEFQLIVNPAKKNNGTAIHKLWFSPE

KVSVKVGTKLKLMCIFGGRPLPNITWSKLNDDLPLARLKDFKSQEADYG

KALIIENVRSEDAGIYECRSQHLFHQMHVTTNAAPFWIDKPPEDIDEPE

GSSAEIHCTISGIPTPIIQWFINGVPLHELADNDRRMILNSGQILRIVN

LDHDVDTAVYQCNASNPFGYVFGNAFVNVRAYAPYFKMPSHRIWNVVRK

STVEMSCDVEAAPKAVVKWVDTNDHSIAVVLEKINIFPNHTLRISQVNS

ADEGLYYCNVSNKYGINRAVNQLQVFNPTHFIRVPSPKKSILEAHESVE

YVCEAVCDPRLTIEYSWTHNGIPINDSVHFKLLNNSLLIVNARGFHSGT

IDCIVLTDVDVKISGIELTVLDVPAAPIITGINCNERRAMLRWRRPDDH

GDQIKQFLIQMHTEFEEGLWQTVVEEENTAADFYQADIALSPWVNYTFR

IIARNSRGESEPGFKEGIVCSTKAYYPFTNPKDVRAEGSEPNNMIIEWK

PMDKYDWNGPGLQYIVRYKFNKPGEAWTEIRIEDPLANYTVIREQPTFR

EYLIQVESLNSFGRAVVKPTSVKGYSGEDTPLLSPIDFSVSEFINCTAV

LLIWKHVDRDSVRGHFKGYLIDYWENEKPFAIMNAGAEKHKNETILYDL

KPMTNYTARIRTANSRYLSESPSIIKFTTPEGIPSKVHNMRVRAVGARS

LYVTWEPPRQPNGYVRGYFITFENSSTGVKEETFVLNRQLYYLNEEGEP

DTGYRVSVWAETKGGEGPKVVRPVRTWPLREPDVPNFTVEAISPTTARV

QWLPSNGSEWAMPGPIFLVNYSIANSNNWIESEQISLPRTEVWLSDLEE

DTRYKMIGIAKEGQRQRASEIITMRSLSRATITHISHESLQSAAWFIAV

VSAIMFALFTASVMCCCERQRDSKYSVKQKELEQGHHIDIEEDQNFMEY

LYGFK
```

The mRNA sequence of Bma-LAD-2 is as follows (lower case letters are untranslated regions, UTR):

```
(SEQ ID NO: 4)
gtcgctctatcctgtttttaaacagttgtgtagcgacaatatcagtgac cggcATGATTACGCTATCTATTCTTTGGTGTTCGCTTTTTCAATTTATT

GCTTTCAGCCGTACACTCGGTCCACCAAAACTAGATCCAGAAAATGGTG
```

```
GAGAAGTATGGTTTCAAGTGAATTCGACCGGTATCGCACGTGGTAAATT

TATTCTTCCGTGCTATGCCACTGGTAATCCAGAAACATATGAGTGGTTT

AAGGATGGAGAAAAACTAAAAGTTGATGGTGATAGGATTGCGTGGGAAA

AACAATTCCAAAGCGGTACCATAATAATCAATGACGCTCGAGATGGAGA

TCAAGGTTATTATCAGTGTCACGCCTCCAATATTTTTGGGATTGCTGTT

TCCAATAAATTTCACGTGCAAATTGGAGTTCTTGATCATTTTGTGCCCC

GAGGTGTGCGTCGATTGATAGTAGACGAAGGACAAAGCTTAAGTATTCG

ATGTGATATTCCGTATGGGGTGCCAAAACCATCTGTTTTTTGGCTTTAT

CGCGATACACAACGAACAAATATGATCGAAACTATTCGATACAAACATA

TTGCTGTCGATACCGAAGGTACCCTTCATTTCACAGCGGTTAAAAAACA

TGACGGGCGGCAAAATTTAATTTACCAATGCGCAGTGACTTCTCCTGTA

CTGCGTGGGGAATATCGTGCAGGCAACGAATTCCAACTTATTGTCAATC

CTGCTAAAAAAACAATGGAACGGCTATACATAAGCTGTGGTTTAGTCC

AGAAAAAGTATCTGTCAAAGTAGGAACCAAACTCAAACTGATGTGCATC

TTCGGTGGAAGGCCACTACCGAACATAACGTGGAGTAAATTAAATGATG

ATTTGCCGCTTGCTCGCTTAAAGATTTTAAATCACAAGAAGCTGACTAC

GGTAAAGCTCTGATCATCGAAAATGTTCGTTCAGAAGATGCGGGGATAT

ATGAATGTCGATCACAGCATCTATTTCATCAGATGCATGTTACTACCAA

TGCAGCTCCATTTTGGATAGATAAACCACCGGAAGACATTGACGAACCG

GAAGGAAGTAGCGCTGAAATCCATTGCACAATATCGGGCATCCCAACAC

CCATCATTCAGTGGTTCATCAATGGTGTACCTTTACATGAGTTGGCAGA

CAATGATCGACGTATGATTTTAAATAGTGGTCAGATATTACGAATCGTA

AACTTGGATCATGATGTTGATACAGCCGTATATCAGTGCAATGCATCGA

ATCCGTTTGGATACGTTTTTGGAAATGCTTTCGTGAATGTGCGCGCTTA

TGCTCCATATTTCAAAATGCCAAGTCACCGTATCTGGAATGTGGTGCGT

AAATCAACCGTAGAGATGTCGTGCGATGTTGAAGCAGCACCGAAAGCAG

TGGTCAAATGGGTAGACACTAATGATCATTCCATTGCTGTTGTTCTCGA

AAAAATCAATATTTTCCCCAATCACACATTGCGCATATCGCAAGTAAAT

TCGGCTGATGAAGGCCTTTACTATTGCAATGTATCGAACAAGTATGGTA

TCAATCGAGCTGTTAATCAACTACAAGTTTTCAATCCAACACATTTTAT

TCGTGTACCAAGTCCAAAGAAGTCAATATTGGAAGCGCATGAGTCAGTG

GAATATGTGTGTGAAGCAGTTTGTGATCCACGGCTTACGATTGAATATT

CTTGGACCCATAATGGAATACCAATTAATGATTCTGTCCACTTCAAGCT

ATTAAACAATTCTCTGTTAATCGTTAATGCTCGTGGCTTTCATTCAGGA

ACCATTGATTGTATTGTTCTTACCGATGTTGACGTCAAGATTTCAGGAA

TTGAATTAACTGTGCTTGATGTGCCTGCTGCTCCAATAATAACAGGAAT

AAACTGCAACGAGCGAAGAGCGATGTTAAGGTGGCGTCGACCAGATGAC

CACGGTGACCAAATCAAACAGTTTCTCATTCAAATGCATACTGAATTTG

AAGAAGGATTGTGGCAAACTGTTGTGGAGGAAGAAAATACTGCTGCCGA

TTTTTATCAGGCTGATATTGCACTTTCACCGTGGGTAAATTATACATTT
```

-continued

```
CGTATAATAGCTCGGAATTCACGTGGTGAAAGTGAACCCGGCTTCAAAG

AAGGCATAGTGTGTTCCACGAAAGCTTACTATCCATTTACAAATCCAAA

GGATGTCCGAGCCGAAGGCAGTGAACCAAACAATATGATTATCGAATGG

AAGCCTATGGATAAATATGATTGGAACGGACCAGGATTACAGTACATCG

TCCGTTATAAGTTTAATAAACCAGGGGAAGCTTGGACAGAAATACGAAT

TGAAGATCCTTTAGCCAATTATACAGTTATTCGCGAACAGCCAACATTC

AGAGAATATTTGATTCAAGTTGAATCTCTGAATAGTTTTGGTCGCGCAG

TTGTGAAACCAACGAGTGTTAAAGGATATTCAGGAGAAGACACACCACT

GTTGTCGCCGATTGATTTCAGCGTGTCTGAATTCATAAATTGTACTGCT

GTTCTTCTTATATGGAAACACGTGGATCGAGACAGTGTGCGTGGTCATT

TCAAAGGTTATCTGATTGACTATTGGGAAAATGAGAAGCCATTTGCTAT

AATGAATGCTGGAGCTGAAAAACATAAGAATGAGACGATTCTTTATGAT

CTAAAGCCTATGACAAACTATACGGCACGTATTAGAACAGCGAATAGTC

GATACCTAAGTGAATCTCCATCAATAATCAAATTTACAACTCCTGAAGG

AATTCCATCCAAGGTACACAATATGAGAGTACGAGCAGTTGGAGCAAGA

AGCTTGTATGTTACATGGGAACCACCGCGACAACCAAATGGATACGTCC

GCGGCTATTTCATTACTTTTGAAAATTCCTCGACAGGCGTAAAAGAAGA

AACATTTGTACTAAATCGACAACTTTATTATTTAAATGAAGAAGGTGAG

CCAGACACTGGCTATAGGGTTTCTGTTTGGGCAGAAACGAAAGGTGGTG

AAGGACCAAAAGTTGTTCGCCCAGTACGAACTTGGCCACTTCGAGAACC

GGATGTACCAAATTTCACCGTCGAAGCAATTTCGCCTACAACGGCTCGA

GTTCAATGGTTGCCTTCGAATGGTTCCGAATGGGCTATGCCAGGGCCTA

TTTTTCTTGTCAATTATTCTATTGCCAACAGCAATAATTGGATAGAAAG

TGAACAAATAAGTTTGCCTCGAACTGAAGTATGGTTAAGCGATCTAGAA

GAAGACACACGATATAAAATGATTGGTATCGCTAAGGAAGGTCAAAGGC

AGCGAGCATCCGAAATAATTACCATGCGAAGCCTAAGTCGAGCTACGAT

TACACACATTTCTCATGAAAGCTTGCAAAGTGCAGCCTGGTTCATCGCA

GTAGTGAGTGCAATAATGTTTGCATTATTCACTGCATCAGTAATGTGTT

GCTGCGAACGGCAACGAGATAGTAAATATTCCGTTAAACAGAAAGAATT

GGAACAAGGCCATCATATCGATATCGAAGAGGACCAGAATTTTATGGAA

TACCTGTATGGATTCAAATGAttaactatcatattatcgcttgttccat ctaataccaataaaccatatctatattacatcatttgcccctaattcat atactgcccgattgataaaattcacactcaactatgtatgtctctttct ctatttacatcactacgcgg
```

Inhibitor Compositions

Various inhibitors of UGT enzymes are known. (See, for example, Walsky et al., *Drug Metab. Dispos.*, 40(5):1051-1065, 2012 and WO 2011/026112). The mechanism of such transferase enzymes are also well known. UGTs catalyze the transfer of glucuronic acid from the co-factor UDP-glucuronic acid (UDPGA) to a nucleophilic group of a substrate, increasing the size and polarity of the product compound and thus enabling active transport and cellular efflux of the derivatized compound. (Ziegler et al., *J. Biol. Chem.*, 290(12):7622-7633, 2015). Thus, uridine 5'-diphospho-glucuronosyltransferase is a cytosolic enzyme catalyzing the covalent transfer of the glucuronic acid moiety of uridine 5'-diphospho-glucuronate to various enzyme-specific small hydrophobic molecules. Glucuronidation is a major part of phase II metabolism and is a critical phase II conjugative enzyme. Xenobiotics often become glucuronidated prior to elimination in animals. Thus, glucuronidation is a major detoxification pathway in vertebrates. (See, Grancharov et al., *Pharmaco. & Therapeutics*, 89(2):171-186, 2001). The pharmaceutical industry has therefore intensely studied this class of enzymes for many decades. UGT enzymes are found throughout the animal kingdom, as well as in plants, and bacteria. Inhibitors of UGT are reported in the literature originating from many sources including endogenous compounds, clinical drugs, environmental contaminants, and natural toxic substances commonly found in the diet of animals. (Id.). Even bile acid components have been implicated in down-regulation of UGT enzymes. (Fang et al., *J. Lipid. Res.*, 54:3334-3344, 2013).

Two inhibitors of UGT that are FDA-approved to treat gout include probenecid and sulfinpyrazone. (Domenjoz R., *Annals of the New York Academy of Sciences*, 1960; 86(1): 263-91; Uchaipichat et al., *Drug Metab. Dispos.*, 2006; 34(3):449-56; Cunningham et al., *Clin. Pharmacokinet.*, 1981; 6(2):135-51; Uchaipichat et al., *Drug Metab. Dispos.*, 2004; 32(4):413-23). These UGT inhibitors are FDA-approved and have been shown to be safe in humans. (Caravati E M, McGuigan M A, Whyte I M, Dawson A H, Seifert S A, Schonwald S, et al. Uricosuric Agents. In: Dart R C, editor. Medical Toxicology. Philadelphia, PA 19106 USA: Lippincott Williams &Wilkins; 2003. p. 916-8). A previous study investigating sulfinpyrazone showed a maximum concentration (Cmax) in humans of 79.9 µM for a 400 mg dose. (Rosenkranz et al., *Eur. J. Clin. Pharmacol.*, 1983; 24(2): 231-5). The daily maximum recommended dose for humans is 800 mg. (Perez-Ruiz et al., *J. Uricosuric Therapy of Hyperuricemia in Gout*, 2012, p. 148-53). Thus, in certain embodiments of the methods and composition described herein the UGT inhibitor is probenecid. In certain embodiments of the methods and composition described herein, the UGT inhibitor is sulfinpyrazone.

Other inhibitors of UGT enzymes are known to one of skill in the art and reported in the literature, such as, but not limited to: sulfinpyrazone, p-(di-n-propylsulphamyl)-benzoic acid (probenecid), 5,7-dihydroxyflavone (chrysin), 5-(2,4-difluorophenyl)-2-hydroxybenzoic acid (diflunisal), 2-((2,3-dimethylphenyl)amino)benzoic acid (mefenamic acid), (2R,3R)-3,5,7-trihydroxy-2-[(2R,3R)-3-(4-hydroxy-3-methoxyphenyl)-2-(hydroxymethyl)-2,3-dihydrobenzo[b][1,4]dioxin-6-yl]chroman-4-one (silibinin), 5,6,7,8-tetramethoxy-2-(4-methoxyphenyl)-4H-1-benzopyran-4-one 5,6,7,8,4'-pentamethoxyflavone (tangeretin), 1-acetyl-4-(4-{[(2R,4S)-2-(2,4-dichlorophenyl)-2-(1H-imidazol-1-ylmethyl)-1,3-dioxolan-4-yl]methoxy}phenyl)piperazine (ketoconazole), 1-(butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl}-4,5-dihydro-1H-1,2,4-triazol-5-one (itraconazole), 5-thiazolylmethyl ((alphaS)-alpha-((1S,3S-1-hydroxy-3-((2S)-2-(3-((2-isopropyl-4-thiazolyl)methyl)-3-methylureido)-3-methylbutyramido)-4-phenylbutyl)phenethyl)carbamate (ritonavir), 5-((3,4-dimethoxyphenethyl)methylamino)-2-(3,4-dimethoxyphenyl)-2-isopropylvaleronitrile (verapamil), (+)-dipentene (D-limonene), 2',4',5',7'-tetrabromo-4,5,6,7-tetrachlorofluorescein (cyanosine), bilirubin, (5α,14β,18R)-17-(cyclopropylmethyl)-18-[(1S)-1-hydroxy-1,2,2-trimethylpropyl]-6-methoxy-18,19-dihydro-4,5-epoxy-6,14-ethenomorphinan-3-ol (buprenorphine), (22R,25R)-3β- hydroxy-5α-spirostan-12-one (hecogenin), 1-napthol, 2-{[3-(trifluoromethyl)phenyl]amino}pyridine-3-carboxylic acid (niflumic acid), or 2-(2-((2,6-dichlorophenyl)amino) phenyl)acetic acid (diclofenac). These UGT inhibitors are contemplated for use in the compositions and methods of treating filarial infections described herein. In certain embodiments, the UGT inhibitors can be used in combination, simultaneously, in series, or singly and packaged as such in the disclosed inhibitor compositions.

In other embodiments of the methods and compositions described herein, the inhibitor of UGT is an N-acyl phenylaminoalcohol residue and a uridine moiety connected by a spacer, wherein the spacer comprises a hydrocarbyl or a substituted hydrocarbyl. (See, WO 2011/026112). According to WO 2011/026112, the spacer moiety is designed to mimic the charge and size of the UDP-glucuronic acid phosphate groups that connect the glucuronic acid group to the ribose group. The spacer, while mimicking these groups, does not allow the same UGT catalytic activity as native UDP-glucuronic acid. Typically, the linker may comprise a hydrocarbyl or a substituted hydrocarbyl.

While no specific IgI-DCP inhibitors are known, as detailed above, IgI-DCP proteins are closely associated with cell adhesion molecules since the I-set domain is found in several cell adhesion molecules including vascular (VCAM), intercellular (ICAM), neural (NCAM) and mucosal addressin (MADCAM) cell adhesion molecules, as well as junction adhesion molecules (JAM). Thus, molecules that are known to disrupt or otherwise block, interfere with, mitigate, antagonize, or otherwise reduce cell adhesion molecule (CAM)-containing proteins from interacting with their cognate binding partners are contemplated as inhibitors of IgI-DCP. Compositions including such inhibitors are also contemplated herein. CAMs are typically found on the surface of the cells and are involved in binding with other cells or with the extracellular matrix to participate in cell adhesion. CAMs allow cells to remain tightly close to each other and are crucial components of maintaining tissue structure and function. There are four major families of CAMs including immunoglobulin superfamily cell adhesion molecules (IgCAMs), cadherins, integrins, and the superfamily of c-type lectin-like domain proteins (CTLDs). Proteoglycans are also considered to be a class of CAM. Various known antibodies binding to the CAM family of proteins are reported in the literature and contemplated herein. (See, Ghosh, S., Therap. Adv. Gastroenterol., 3(4):239-258, 2010, and Podar et al., Blood, 114:1850, 2009). Small molecule inhibitors of CAMs are also reported in the literature. (See, Besemer et al., Nature, 436:290-293, 2005, describing CAM741).

Thus, both UGT enzymes as well as IgI-DCP proteins are capable of being inhibited by antibodies, nucleic acid inhibitor molecules, such as siRNA, antisense molecules, or aptamers, and other small molecules that specifically associate with these targets as reported in the literature and noted above. In one embodiment, the siRNA molecule is specific for UGT, and is one or more of SEQ ID NOS: 6, 8, and 10. In another embodiment, the siRNA molecule is specific for IgI-DCP, and is one of SEQ ID NOS: 21, 23, and 25. Inhibitors of UGT enzymes and IgI-DCP proteins include those that directly inhibit their target as well as those that indirectly inhibit their target, i.e. by inhibiting another enzyme or protein upstream or downstream in the functional pathway of the target. Such inhibitors are contemplated herein as being useful in treating and/or preventing helminthiases, such as filariasis. Such inhibitors are contemplated to be used singly or in various combinations to treat and/or prevent helminthiasis. In certain embodiments, the inhibitor is an antibody. In certain embodiments, the antibody is a polyclonal antibody. In certain embodiment, the antibody is a monoclonal antibody.

In certain aspects, the UGT or IgI-DCP inhibitor (also referred to as active pharmaceutical ingredients, or active agents) is part of a composition. In certain embodiments, the composition is a pharmaceutical composition and comprises a pharmaceutically acceptable carrier. The carrier is "acceptable" in the sense that it is compatible with the active ingredient of the composition, i.e. the inhibitor(s), and typically, capable of stabilizing the active ingredient and not deleterious to the animal to be treated. In some embodiments, the pharmaceutically acceptable carrier is a non-naturally occurring pharmaceutically acceptable carrier.

In an embodiment of an inhibitor composition comprising a carrier, pharmaceutically acceptable carriers (vehicles) can be in some instances conventional, but are not limited to conventional carriers (vehicle). For example, E. W. Martin, Remington's Pharmaceutical Sciences, Mack Publishing Co., Easton, PA, 15th Edition (1975) and D. B. Troy, ed. Remington: The Science and Practice of Pharmacy, Lippincott Williams & Wilkins, Baltimore MD and Philadelphia, PA, 21st Edition (2006) describe compositions and formulations suitable for pharmaceutical delivery of one or more molecules and additional pharmaceutical agents.

Effective amounts of the inhibitor compositions are dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art.

Methods of Prevention and/or Treatment of Helminthiasis

While there is interest in the field in developing a drug that kills adult filarial worms, it could also be advantageous if it is not markedly microfilaricidal. When given individually, current antifilarial therapeutics such as diethylcarbamazine (DEC) and ivermectin (IVM) are extremely effective at clearing microfilariae but exhibit little activity against adult filarial worms. (Ottesen E A. Lymphatic Filariasis: Treatment, Control and Elimination. In: Molyneux D H, editor. Advances in Parasitology. 61: Academic Press; 2006. p. 395-441). However, their use is contraindicated in areas co-endemic to loiasis and onchocerciasis because rapid killing of microfilariae in these infections can lead to severe adverse outcomes. (Boussinesq et al., Int. Health, 2018; 10(suppl_1):i40-i8). Loa loa patients treated with IVM or DEC have a significantly higher risk of experiencing severe neurologic events such as encephalopathy due to rapid microfilariae death in the vasculature. (Twum-Danso N A, Filaria J., 2003; 2 Suppl 1:S7; Wanji et al., PLoS Negl. Trop. Dis., 2017; 11(7):e0005576). Similarly, DEC can induce adverse systemic reactions such as skins lesions, fever, polyarthritis, and ocular reactions in patients with onchocerciasis as determined by microfilariae load. (Albiez et al., Trop. Med. Parasitol., 1988; 39(1):19-24; Awadzi et al., Br. J. Clin. Pharmacol., 1992; 34(4):281-8). Disclosed herein are alternative methods of treating such helminth (e.g., filarial) infections and the diseases caused thereby employing inhibitors of UGT and/or IgI-DCP enzymes to treat and/or prevent helminth (e.g., filarial) infection. Without intending to be bound by any theory, it appears these inhibitors are effective at killing adult worms but exhibit little activity against microfilariae, thus providing an improvement over the current antifilarial therapeutics, such as DEC and IVM.

Thus, disclosed herein are methods of treatment and/or prevention of helminth (e.g., filarial) diseases in a subject animal in need thereof comprising administration of a therapeutically effective amount of a UGT inhibitor and/or an IgI-DCP inhibitor. In one embodiment, the method comprises administering a UGT and/or an IgI-DCP inhibitor as described herein to an animal in need thereof, where the animal is at risk of developing a helminth (e.g., filarial) infection. In another embodiment, the method comprises administering a UGT and/or an IgI-DCP inhibitor as described herein to an animal in need thereof, where the animal has a helminth (e.g., filarial) infection.

In a particular embodiment, a therapeutically effective amount of a UGT inhibitor is administered to the animal in need thereof. In another embodiment, a therapeutically effective amount of an IgI-DCP inhibitor is administered to the animal in need thereof. In another embodiment, a therapeutically effective amount of probenecid is administered to the animal in need thereof. In another embodiment, a therapeutically effective amount of sulfinpyrazone is administered to the animal in need thereof. In another embodiment, a therapeutically effective amount of a molecule that interrupts, disrupts, or otherwise interferes with cell adhesion molecule function is administered to the animal in need thereof.

It is furthermore contemplated herein that the methods described are used in combination with other known and/or approved, first-line, treatment methods for treating and/or preventing helminth (e.g., filarial) infection, such as the administration of anthelmintic drugs and/or antifilarial drugs. That is, the methods described herein are not mutually exclusive to other, already known and practiced (traditional), and perhaps somewhat effective, methods of treating and/or preventing helminth (e.g., filarial) infection. It is contemplated herein that additive, or even synergistic, effects can be realized by combining the therapies and methods disclosed herein with known therapies, thereby allowing reduction of the amount of the prior known therapies to be utilized in the method, and thus decreasing cost and/or decreasing harmful or toxic side effects of known therapies. In one particular embodiment, the UGT inhibitor and/or the IgI-DCP inhibitor is combined with one or more anthelmintic drugs known in the art. (See, for instance, Rubin Means et al., *Cochrane Databse Syst. Rev.,* 4:1-16, Apr. 14, 2016; and Holden-Dye et al., "Anthelmintic drugs," in WormBook, Eds. V. Maricq and S. L. McIntire, Nov. 2, 2007, The *C. elegans* Research Community, doi/10.1895/ wormbook.1.143.1). In one embodiment, the combined therapy comprises administration of sulfinpyrazole with an anthelmintic drug, such as albendazole. In another embodiment, the combined therapy comprises administration of probenecid with an anthelmintic drug, such as albendazole. In another embodiment, combined therapy comprises administration of both sulfinpyrazole and probenecid with an anthelmintic, such as albendazole.

In one embodiment, the filarial disease is caused by one or more of the following filarial species of *Brugia, Wuchereria, Onchocerca, Loa,* or *Dirofilaria.* In one embodiment, the filarial disease is caused by one or more of the following species: *Brugia malayi, Brugia timori, Wuchereria bancrofti, Dirofilaria immitis, Dirofilaria vivaparus, Onchocerca volvulus,* or *Loa.* In one embodiment, the filarial disease is caused by one or more of the following species: *Brugia malayi, Brugia timori, Wuchereria ban-*

*crofti, Dirofilaria immitis,* or *Loa.* In one embodiment, the disease is caused by one or more species of *Dirofilaria,* such as *Dirofilaria immitis,* and/or *Dirofilaria viviparus.*

In another embodiment, the disease is a helminthiasis caused by infection of any one or more of the following non-filarial helminth species: *Haemonchus, Necator, Shistosoma, Oesophagostomu, Trichuris, Trichostrongylus, Ancylostoma, Fasciola, Oesophagostomu, Gnathostoma.* In one embodiment, the helminthiasis disease is caused by one or more of the following species: *Haemonchus contortus, Haemonchus placei, Haemonchus similis, Necator americanus, Trichuris trichiura, Strongyloides stercoralis, Enterobius vermicularis* (pinworm), *Gnathostoma spinigerum, Ancylostoma duodenale,* or *Fasciola hepatica.* In a further embodiment, the helminthiasis disease is caused by one or more species of *Haemonchus,* such as *Haemonchus contortus, Haemonchus placei,* or *Haemonchus similis,* and particularly *Haemonchus contortus.*

The species of animal to be treated is not particularly limited other than that the animal must be one that is susceptible of being infected by one or more species of helminth (e.g., filarial) worm disclosed herein. The hosts of such worms are well known and reported in the art. For instance, in an embodiment of the disclosed methods, the animal is a ruminant animal, a livestock animal, or a companion animal. In a further embodiment, the ruminant animal or other livestock animal is a sheep, a goat, a cow, a llama, a camel, a horse, a mule, a pig, a bird, a rabbit, a deer, an elk, or a giraffe. In other embodiments, particularly when the disease being prevented or treated is heartworm, the companion animal is a dog or a cat, typically a dog. In another embodiment, the animal is a human.

Methods of preparing and administering the inhibitor compositions disclosed herein to an animal in need thereof are well known to or are readily determined by those skilled in the art. The route of administration of the inhibitor compositions disclosed herein can be, for example, oral, parenteral, by inhalation or topical. The term parenteral as used herein includes, e.g., intravenous, intraarterial, intraperitoneal, intramuscular, subcutaneous, rectal, or vaginal administration.

The amount of the inhibitor compositions disclosed herein to be combined with the carrier materials to produce a single dosage form will vary depending upon the animal's body weight, age, gender, health condition, diet, administration time, administration method, excretion rate, and disease severity. The composition can be administered as a single dose, multiple doses, or over an established period of time in an infusion. Dosage regimens also can be adjusted to provide the optimum desired response (e.g., a therapeutic or prophylactic response).

The inhibitor compositions disclosed herein are administered, for example, with a single dose or with multiple doses, if desired. In one embodiment, the inhibitor compositions described herein are administered regularly for long periods of time. In an embodiment, the composition is administered regularly for 1, 2, 3, 4, 5, 6, 7, 8, 9, 10, or more years. In another embodiment, the composition is administered regularly for 1, 2, 3, 4, 5, 6, 7, 8, 9, 10, 11, 12, or more months. In other embodiments, the composition is administered regularly for 1, 2, 3, 4, 5, 6, 7, 8, 9, 10, or more weeks. As used herein, the term "regularly" refers to administration of the composition at regular times or intervals over a period of time. It should be appreciated that the frequency of administration varies based on a number of factors, including, but not limited to, the severity of disease, the overall health of the animal, any additional medications the animal is taking, and whether the treatment is prophylactic or not. It should also be appreciated that the frequency of administration may be adjusted at any point.

The disclosed inhibitor compositions are administered to an animal in need thereof on any schedule appropriate to treat and/or prevent infection as described below. For example, animals can be administered an inhibitor composition as a primary regimen to prevent helminthiasis (e.g., filariasis) as described and exemplified herein, followed by administration of a secondary dose to bolster and/or maintain protection against future infection.

The inhibitor composition administration schedule, including primary and secondary, or more, administration, can continue as long as needed for the animal in need thereof, for example, over the course of several years, to over the lifetime of the animal. The frequency of administration and dose administered can be tailored and/or adjusted to meet the particular needs of animal, as determined by the administering physician or veterinarian according to any means suitable in the art.

Immunogenic Compositions

Based on the present disclosure and discoveries described herein, in addition to being a potential drug target for helminthiasis, UGT and IgI-DCP of helminth species are also attractive vaccine candidates. One of the challenges in helminth vaccine development is the risk that the vaccine may induce an allergic response in endemic populations. Indeed, generalized urticaria was seen in several Brazilian patients immunized against *Ancylostoma*-secreted protein 2 during hookworm vaccine trials. (Diemert et al., *J. Allergy Clin. Immunol.*, 2012; 130(1):169-76 e6). A solution to this obstacle is to identify "hidden antigens" which are not exposed to the immune system during natural infection. (Bennuru S, *EBioMedicine*, 2015; 2(9):1010-1; Munn E A, *Int. J. Parasitol.*, 1997; 27(4):359-66). In theory, these proteins would not elicit an IgE-mediated response, and, as postulated by Munn, these antigens may be especially vulnerable to the immune system due to a lack of evolutionary pressure to evade it. (Munn E A, *Int. J. Parasitol.*, 1997; 27(4):359-66). There is evidence to support that the intestinal tract of nematodes contains hidden antigens. Studies have demonstrated the absence of pre-existing IgE in serum from endemic populations against hookworm worm intestinal antigens APR-1 and GST. (Pearson et al., *FASEB J.*, 2009; 23(9):3007-19; Pearson et al., *J. Infect. Dis.*, 2010; 201(10):1561-9; Diemert et al., *PLoS Negl Trop Dis.*, 2017; 11(5):e0005574). Furthermore, studies have shown that these antigens are protective in animal models. (Pearson et al., *FASEB J.*, 2009; 23(9):3007-19; Zhan et al., *Infect. Immun.*, 2005; 73(10):6903-11; Zhan et al., *Infect. Immun.*, 2010; 78(4):1552-63). There is also evidence of hidden antigens in *H. contortus* seen with the lack of an antibody response against H11, a glycosylated intestinal protein. (Newton et al., *Int. J. Parasitol.*, 1995; 25(4):511-21). Since no IgE antibody response was detected (below) when examining infected patients for antibodies against UGT and/or IgI-DCP proteins (as shown below), these targets are good candidates for immunogenic compositions that aid in vaccinating or otherwise preventing future infections in animals in need thereof.

In some embodiments, the present disclosure encompasses an immunogenic composition comprising at least one UGT or IgI-DCP peptide as described herein or an immunogenic fragment thereof and optionally a pharmaceutically acceptable carrier.

In some embodiments, the present immunogenic composition consists essentially of the isolated polypeptides disclosed herein, such as SEQ ID NO:1 or SEQ ID NO:3 or immunogenic fragments thereof and a pharmaceutically acceptable carrier and does not encompass crude homogenates of antigen, such as a crude homogenate of intestinal proteins.

In some embodiments, the immunogenic composition of the present disclosure is a vaccine. As used herein, a vaccine encompasses an immunogenic composition that prevents, ameliorates, palliates, or eliminates disease from a host, such as the diseases described herein.

In other embodiments, the immunogenic composition described herein may be used to obtain an antibody composition, which may then be administered to an animal to provide temporary immunity, i.e., artificially acquired passive immunity. Methods for preparing and administering such antibody compositions are known in the art and are described, for example, in U.S. Pat. No. 4,748,018, which is herein incorporated by reference in its entirety.

In some embodiments, the polypeptide of the present immunogenic composition is a polypeptide selected from SEQ ID NO:1 or SEQ ID NO:3. In some embodiments, the polypeptide of the present immunogenic composition is an immunogenic fragment, such as an immunogenic fragment of SEQ ID NO:1 or SEQ ID NO:3.

In general, the immunogenic fragments and variants described herein, such as fragments or variants of the polypeptides of SEQ ID NO:1 and SEQ ID NO:3 comprise at least one epitope and include at least six contiguous amino acids from the full-length protein, e.g., at least six contiguous amino acids from the cell adhesion protein set forth in SEQ ID NO:1 or SEQ ID NO:3, for example. More typically, the present variants or fragments will have at least 10, even more typically at least 15, and still more typically at least 19, and yet even more typically 30 contiguous amino acids from the full-length protein, e.g., the UGT enzyme set forth in SEQ ID NO:1 or the cell adhesion protein set forth in SEQ ID NO:3, for example.

In some embodiments, the polypeptides of the present disclosure encompass polypeptides that are substantially homologous to the polypeptides set forth in SEQ ID NOS:1 or SEQ ID NO:3. The substantially homologous polypeptides may be from or derived from any helminth species or genera. In certain embodiments, the substantially homologous polypeptide is a helminth ortholog of UGT. In certain embodiments, the substantially homologous polypeptide is a helminth ortholog of IgI-DCP. For example, the helminth ortholog of UGT or IgI-DCP may be an ortholog from a filarial worm, including but not limited to *Brugia malayi*, *Brugia timori*, *Wuchereria bancrofti*, *Dirofilaria immitis*, *Dirofilaria vivaparus*, *Onchocerca volvulus*, or *Loa loa*. Alternatively, the helminth ortholog of UGT or IgI-DCP may be an ortholog from a non-filarial worm including but not limited to *Shistosoma, Trichostrongylus, Oesophagostomus, Haemonchus contortus, Haemonchus placei, Haemonchus similis, N. americanus, T. trichiura, G. spinigerum, A. duodenale*, or *F. hepatica*.

In specific embodiments, the immunogenic composition of the instant disclosure includes at least one isolated polypeptide, comprising an amino acid sequence having a sequence identity of at least 75%, such as at least 80%, such as at least 85%, such as at least 90%, such as at least 95%, such as at least 97%, such as at least 98%, such as at least 99%, such as at least 100% to a polypeptide selected from SEQ ID NO:1 or SEQ ID NO:3.

In some embodiments, the polypeptides of the present disclosure are recombinant polypeptides that are typically expressed using an expression vector and purified. Expression vectors may be either self-replicating extrachromo-somal vectors or vectors that integrate into a host genome. Generally, expression vectors include transcriptional and translational regulatory nucleic acid sequences, operably linked to the nucleic acid encoding the target protein and suitable vectors for this purpose are well known in the art.

In some embodiments, the immunogenic composition of the present disclosure includes a pharmaceutically accept-able carrier, as described previously in this application.

In some embodiments, immunogenic composition com-prises an adjuvant. As used herein, an "adjuvant" is under-stood as a pharmacological or immunological agent that modifies the effect of other agents (e.g., immunogen or target antigen in an immunogenic composition) while hav-ing few if any direct effects when given by itself. In some embodiments, an adjuvant will enhance the recipient's immune response to the polypeptides in the present immu-nogenic composition while keeping the injected foreign material at a minimum. In certain embodiments, the adju-vant is a non-naturally occurring adjuvant.

Suitable adjuvants are well known in the art (see, for example, *Vaccine Design—The Subunit and Adjuvant Approach* (1995) Pharmaceutical Biotechnology, Volume 6 (eds. Powell, M. F., & Newman, M. J.) Plenum Press, New York and London, ISBN 0-306-44867-X), which is incor-porated herein by reference in its entirety. Examples of adjuvants include, but are not limited to, alum-precipitate, Freund's complete adjuvant, Freund's incomplete adjuvant, monophosphoryl-lipid A/trehalose dicorynomycolate adju-vant, water in oil emulsion containing *Corynebacterium parvum* and tRNA, and other substances that accomplish the task of increasing immune response by mimicking specific sets of evolutionarily conserved molecules including lipo-somes, lipopolysaccharide (LPS), molecular cages for anti-gen, components of bacterial cell walls, and endocytosed nucleic acids such as double-stranded RNA, single-stranded DNA, and unmethylated CpG dinucleotide-containing DNA. Other examples include cholera toxin, *E. coli* heat-labile enterotoxin, liposome, immune-stimulating complex (ISCOM), immunostimulatory sequences oligodeoxynucle-otide, and aluminum hydroxide.

Other exemplary adjuvants include the adjuvants described in Lanar et al., U.S. Pat. No. 7,029,685 and U.S. Patent Publication No. 2006/0073171, herein incorporated by reference in their entireties. Alternatively, the polypep-tides of the immunogenic composition described herein can be used without any adjuvant.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, pat-ents, and other references mentioned herein are incorporated by reference in their entirety. In case of conflict, the present specification, including definitions, will control.

EXAMPLES

Below are provided illustrative non-limiting examples for the purpose of generating a better understanding of the compositions and methods described above and their many advantages. The following examples are included to dem-onstrate preferred embodiments. It should be appreciated by those of skill in the art that the techniques disclosed in the examples which follow represent techniques that function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the compositions and methods described herein.

Example 1: Uptake of Target Specific siRNA in the Intestinal Tract of Adult *B. malayi* Worms The following experiment was performed to evaluate whether siRNA is capable of reaching the intestinal tracts of adult *B. malayi* worms. To this end, cy3-conjugated siRNA was added to the culture media of adult *B. malayi* worms for 24 hrs, as explained in more detail below. Two target genes were tested UGT and LAD-2. The siRNA was specific for either *B. malayi* UGT mRNA transcripts (Bma-iUGT siRNA) or *B. malayi* LAD-2 mRNA transcripts (Bma-LAD-2 siRNA).

Parasites and culture: Female *B. malayi* adults used in this study were obtained from the NIH/NIAID Filariasis Research Reagent Resource Center (FR3) and TRS Labo-ratories in Athens, Georgia, USA. The worms were cultured in Dulbecco's Modified Eagle's Medium (DMEM, Corn-ing® Cellgro®, Thomas Scientific, Swedesboro, New Jer-sey, US) supplemented with 10% heat-inactivated fetal bovine serum (FBS, Atlanta Biologicals, Flowery Branch, GA, US), 100 units/mL of penicillin, 100 µg/mL of strep-tomycin, and 1% L-glutamine (Sigma Aldrich, St. Louis, MO, US) for 24 hrs at 37° C. in 5% $CO_2$ prior to siRNA treatment. Microfilariae were obtained from adult female worms cultured in vitro.

Demonstration of siRNA uptake and antibody ingestion by fluorescence microscopy: For demonstration of siRNA uptake, adult female worms were incubated in 5 µM of 5' cy3-labeled Bma-iUGT siRNA or 5' cy3-labeled Bma-LAD-2 siRNA (Sigma Aldrich, St. Louis, MO, US) for 24 hrs. Adult worms incubated in media alone were used as a negative control. Both groups of worms were then stained with 10 µg/mL of DAPI (Sigma-Aldrich, St. Louis, MO, US) in phosphate-buffered saline (PBS). Fluorescent images were captured by a Nikon Eclipse E600 fluorescent micro-scope and converged using NIS-Elements software. For experiments to test ingestion of antibody, adult female worms were incubated with 100 g of mouse cy3-labeled IgG isotype control in 2 mL of culture media. The worms were imaged 24 hrs later using the tetramethylrhodamine (TRITC) filter on a Zeiss Axio Observer. (Zeiss, Germany).

Visualization of the adult worms showed clear uptake of siRNA throughout the intestinal tract for both targets. In contrast, imaging at the same exposure time revealed no apparent signal in the intestine of adult *B. malayi* cultured in media alone.

Example 2: Bma-iUGT siRNA Reduces UGT mRNA and Protein Expression in Adult Worms Experiments were conducted to evaluate reduction in target transcript and protein levels in *B. malayi* worms incubated with siRNA targeted to UGT. Timepoints of 1, 3, and 6 days post-siRNA treatment based on a protein half-life of approximately 10 hrs for UDP-glucuronosyltransferases (UGT) were selected. (Emi et al., Arch. Biochem. Biophys., 2002; 405(2):163-9).

siRNA design: Using the BLOCK-iT™ RNAi Designer, the top three Bma-iUGT siRNA duplexes were selected for gene silencing activity and specificity (Invitrogen, Carlsbad, CA, US). The Bma-iUGT siRNA and corresponding scrambled siRNA were synthesized by Life Technologies (Carlsbad, CA, US) and purified by standard desalting methods. The 5'-3' sequences of the Bma-iUGT siRNA strands were as follows:

```
Bma-iUGT siRNA 1:
sense:
                              (SEQ ID NO: 5)
5' GCCUAACGAAACUAAGCAAdTdT 3' antisense:
                              (SEQ ID NO: 6)
5' UUGCUUAGUUUCGUUAGGCdTdT 3'

Bma-iUGT siRNA 2:
sense:
                              (SEQ ID NO: 7)
5' GGCUUCCACAAUCUGAUUUdTdT 3' antisense:
                              (SEQ ID NO: 8)
5' AAAUCAGAUUGUGGAAGCCdTdT 3'

Bma-iUGT siRNA 3:
sense:
                              (SEQ ID NO: 9)
5' GGUGGUAUGAAUAGCAUAAdTdT 3' antisense:
                              (SEQ ID NO: 10)
5' UUAUGCUAUUCAUACCACCdTdT 3'
``` siRNA incubation of *B. malayi* female adult worms: siRNA inhibition of Bma-iUGT in *B. malayi* adult female worms followed a protocol established by Aboobaker et al. with minor modifications. (Aboobaker et al., *Mol. Biochem. Parasitol.*, 2003; 129(1):41-51). For each timepoint, 5 adult female worms were soaked in an equal mixture of the Bma-iUGT siRNAs at a total concentration of 5 µM in 850 µL of culture media in a 5000 MWCO Pur-A-Lyzer™ dialysis tube (Sigma-Aldrich, St. Louis, MO, US). This concentration of siRNA was shown in multiple studies to be sufficient at silencing gene expression. (Aboobaker et al., *Mol. Biochem. Parasitol.*, 2003; 129(1):41-51; Kushwaha et al., *PLoS Negl Trop Dis.*, 2012; 6(8):e1770; Misra et al., *Parasit. Vectors*, 2017; 10(1):34; Singh et al., *Infect. Dis. Poverty*, 2013; 2(1):5). The dialysis tubes were placed in 1 L beakers with 500 mL of culture media for 24 hrs at 37° C. in 5% $CO_2$. Similarly, 5 adult female worms were soaked in media alone or scrambled siRNA (5 µM) in dialysis tubes for each timepoint as experimental controls. After the 24-hr incubation, the worms for each group were carefully extracted from the dialysis tubes and individually placed into wells with 1 mL of media. The worms were evaluated at timepoints 1, 3, and 6 days post-incubation for transcript knockdown, worm motility, MTT reduction, and microfilariae release.

RNA extraction and analysis of RNA levels by RT-qPCR: Adult *B. malayi* female worms were homogenized in TRIzol (Thermo Fisher Scientific, Waltham, MA, US) after three freeze/thaw cycles using Matrix D lysis tubes (MP Biomedicals, Santa Ana, CA, US) agitated by a FastPrep™-24 Biopulverizer (MP Biomedicals, Santa Ana, CA, US) for 7 minutes at 6 m/s. Chloroform was added to the homogenate, transferred to Phase Lock Gel tubes (5Prime, South San Francisco, CA, US), and phase separated at 11,900×g for 15 minutes at 4° C. The aqueous phase was collected and cold isopropanol was added to precipitate the RNA, which was then pelleted at 12,000 g for 1 hr and washed twice using 75% ethanol. The RNA pellet was resuspended in nuclease-free water and quantified using a NanoDrop™ 1000 (Thermo Fisher Scientific, Carlsbad, CA, US). cDNA was prepared using Superscript IV (Thermo Fisher Scientific, Carlsbad, CA, US) as per the manufacturer's protocol. The cDNA levels of Bma-iugt and *B. malayi* house-keeping gene gapdh were assessed in duplicate 20 µL reactions using 1 µL of 20× TaqMan™ gene expression assay (Thermo Fisher Scientific, Carlsbad, CA, US), 1 µL of cDNA, and 18 µL of TaqMan™ gene expression master mix (Applied Biosystems). PCR conditions were 2 min at 50° C., 10 min at 95° C., 40 cycles of 15 sec at 95° C., and 1 min at 60° C. cycle of 50° C. with a 7500 Real-Time PCR System (Applied Biosystems, Foster City, CA, US). The primers used were as follows:

```
Bma-gapdh:
Forward primer:
                              (SEQ ID NO: 11)
5' TTGATCTCACTTGCCGACTC 3'

Reverse primer:
                              (SEQ ID NO: 12)
5' TGGTCTTCGGTGTATTCCAA 3'

Internal probe:
                              (SEQ ID NO: 13)
5' CAGCTAATGGACCGATGAAGGGGA 3'

Bma-iugt:
Forward primer:
                              (SEQ ID NO: 14)
5' TATCATTCGGCACCGTTACA 3'

Reverse primer:
                              (SEQ ID NO: 15)
5' ATTCATACCACCATGCGTCA 3'

Internal probe:
                              (SEQ ID NO: 16)
5' TCGCTGAGGGACGTCCAAACG 3'
```

Statistical analysis: The siRNA and UGT inhibitor experiments were repeated two times under similar conditions. For the siRNA experiments, data was analyzed using one-way analysis of variance (ANOVA) or T-test by PRISM 7.0 (GraphPad Software, La Jolla, CA, US). Following ANOVA, individual comparisons of mean values were performed using Tukey's multiple comparisons test. For the UGT inhibitor experiments, area under curve (AUC) analysis was performed followed by one-way ANOVA to determine significance. Statistical significance between the experimental and control groups was designated as follows: * for p values<0.05,  for p values<0.01, and * for p values<0.001.

Generation of rabbit polyclonal antibodies against Bma-iUGT peptides: Polyclonal anti-Bma-iUGT peptide antibodies were generated in New Zealand rabbits by GenScript (Piscataway Township, NJ, US) using Bma-iUGT peptide sequences conjugated to keyhole limpet hemocyanin (KLH). The peptide sequences used are as follows: CYEKDEHLI-AEGRPN (SEQ ID NO:17), DSTGSKLAKTVKIDC (SEQ ID NO:18), and CGQIANFDPYGRKMS (SEQ ID NO: 19). Cysteines were added at either the N- or C-terminus to facilitate KLH conjugation.

Western blot: *B. malayi* adult worms were incubated in 5 µM combination of Bma-iUGT siRNA for 24 hrs using the previously mentioned method and transferred into individual wells with 1 mL of media. The adult worms were cultured for an additional 24 hrs and then homogenized in PBS (pH 7.4) and 4 μL Halt™ Protease Inhibitor Cocktail (Thermo Fisher Scientific, Carlsbad, CA, US) using Matrix D lysis tubes (MP Biomedicals) agitated by a FastPrep™-24 Biopulverizer (MP Biomedicals, Santa Ana, CA, US) for 3 minutes at 4 m/s. Protein levels were quantified by the Bradford protein assay (Bio-Rad, Hercules, CA, US). For Western blot analysis, 10 g of protein was separated on 10% Bis-Tris NuPAGE gel (Invitrogen, Carlsbad, CA, US) and blotted onto 0.2 m nitrocellulose filter paper (Bio-Rad, Hercules, CA, US). After blocking overnight in 5% bovine serum albumin (BSA) in tris-buffered saline with 0.1% Tween 20 (TBS-T), the membrane was incubated with 1:4000 anti-UGT peptide antibodies (GenScript, Piscataway Township, NJ, US) and 1:1000 rabbit anti-β actin antibodies (Abcam, Cambridge, UK) for 1 hr. Following this, the filter paper was washed three times with TBS-T for 15 min. and then incubated with 1:2000 horseradish peroxidase conjugated goat anti-rabbit IgG for 1 hr. The membrane subsequently washed with TBS-T and incubated in Chemiluminescent reagent, SuperSignal™ West Pico PLUS (Thermo Fisher Scientific, Carlsbad, CA, US), to visual the bands.

Figures 3A, 3B:
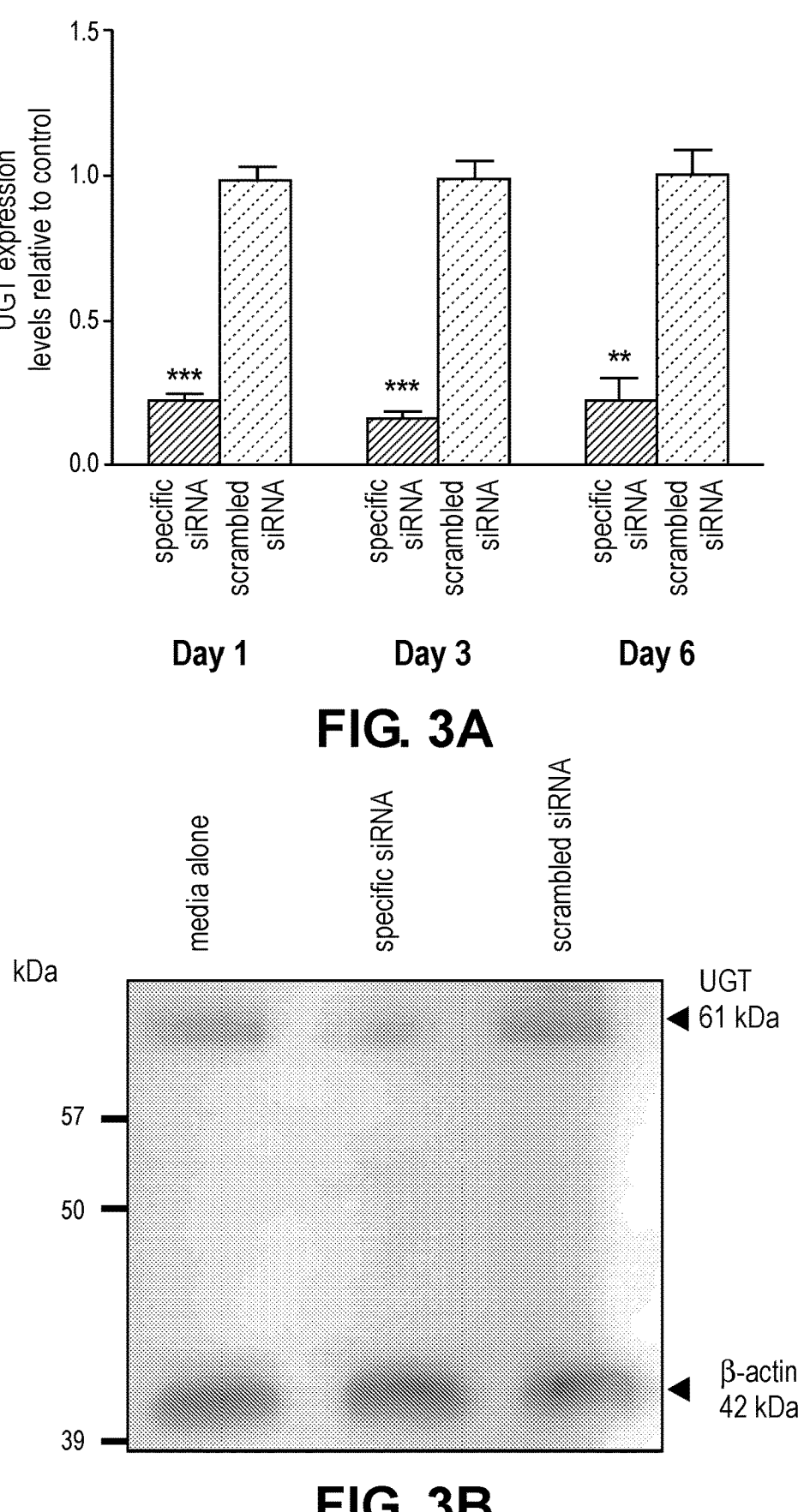
FIGS. 3A, 3B, 3C show that incubation of adult *B. malayi* with UGT-specific siRNA reduces target transcript and protein levels. Adult female worms were incubated with UGT-specific siRNA, scrambled siRNA, or media alone. Target mRNA levels in the specific siRNA and scrambled siRNA treated groups were measured by RT-qPCR relative to the media control with glyceraldehyde 3-phosphate dehydrogenase (GAPDH) as a normalization control.

Results: After a 24-hr incubation with UGT-specific siRNA or scrambled siRNA, Bma-iugt mRNA expression was compared between the treated worms relative to the media control by RT-qPCR (FIG. 3A). Transcript expression was normalized employing the housekeeping gene encoding glyceraldehyde-3-phosphate dehydrogenase (Bma-gapdh, Bm5699). Bma-iUGT siRNA treatment resulted in a 77.1% reduction (p=0.0056) in target mRNA compared to the controls 1 day post-siRNA treatment. Transcript knockdown was sustained throughout the experiment with a 76.23% decrease (p=0.0003) in Bma-iugt transcription 6 days post-siRNA incubation (FIG. 3A). There was no significant difference observed in target transcription between the media control and scrambled siRNA groups, also a negative control.

Figure 3C:
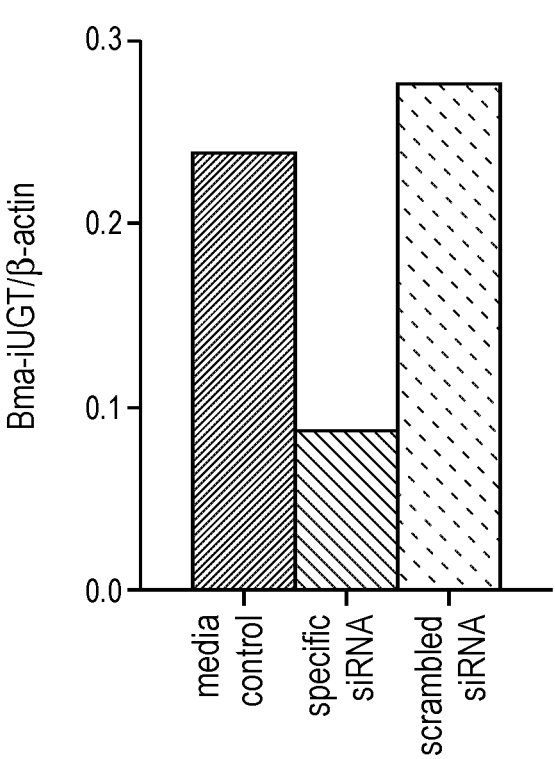

Bma-iUGT knockdown was further substantiated by Western blot analysis (FIG. 3B). Target protein expression was evaluated 24 hrs post-siRNA incubation using anti-Bma-iUGT peptide antibodies. There was a robust reduction in UGT protein expression with the Bma-iUGT siRNA treated worms compared to controls normalized to β-actin (87% reduction in Bma-iUGT/I-actin) (FIG. 3C).

Example 3: Bma-iUGT Knockdown Results in Decreased Worm Viability and Fecundity After successfully demonstrating that siRNA reduces Bma-iUGT expression, resultant changes in worm motility, microfilariae release, and metabolism were investigated. Metabolism was evaluated by a (4,5-dimethylthiazol-2-yl)-2,5-diphenyltetrazolium bromide (MTT) reduction assay.

Worm motility: Worms were visualized with a dissecting microscope by an observer blinded to treatment category. Motility of the adult female B. malayi worms was rated based on the following scale: 4=active movement, 3=modest reduction in movement, 2=severe reduction in movement, 1=twitching, and 0=no movement.

Microfilariae release: For each timepoint, adult worms were placed in new culture media 24 hrs prior to enumeration of microfilariae. After the overnight incubation, the worms were then removed for processing by the (4,5-dimethylthiazol-2-yl)-2,5-diphenyltetrazolium bromide (MTT) reduction assay and reverse-transcription-quantitative polymerase chain reaction (RT-qPCR). The microfilariae in the well containing expended culture media (1 mL) were counted under a light microscope at high magnification.

MTT reduction: Metabolic function of the adult female worms was assessed by reduction of (4,5-dimethylthiazol-2-yl)-2,5-diphenyltetrazolium bromide (MTT) (Sigma-Aldrich, St. Louis, MO, US) using a protocol established by Comley et al., Int. J. Parasitol., 1989; 19(1):77-83. For each group per timepoint, 2 worms were incubated in 0.5 mL of phosphate buffered solution (PBS) pH 7.4 with 0.5 mg/mL of MTT for 30 minutes at 37° C. in 5% $CO_2$. The worms were then transferred into separate wells of a 96-well plate containing 200 μL of dimethylsulfoxide (DMSO) and incubated at room temperature for 1 hr. MTT reduction was quantified by absorbance relative to a DMSO blank at 570 nm using a Synergy HTX multi-mode plate reader (BioTek, Winooski, VT, US).

Figure 4A:
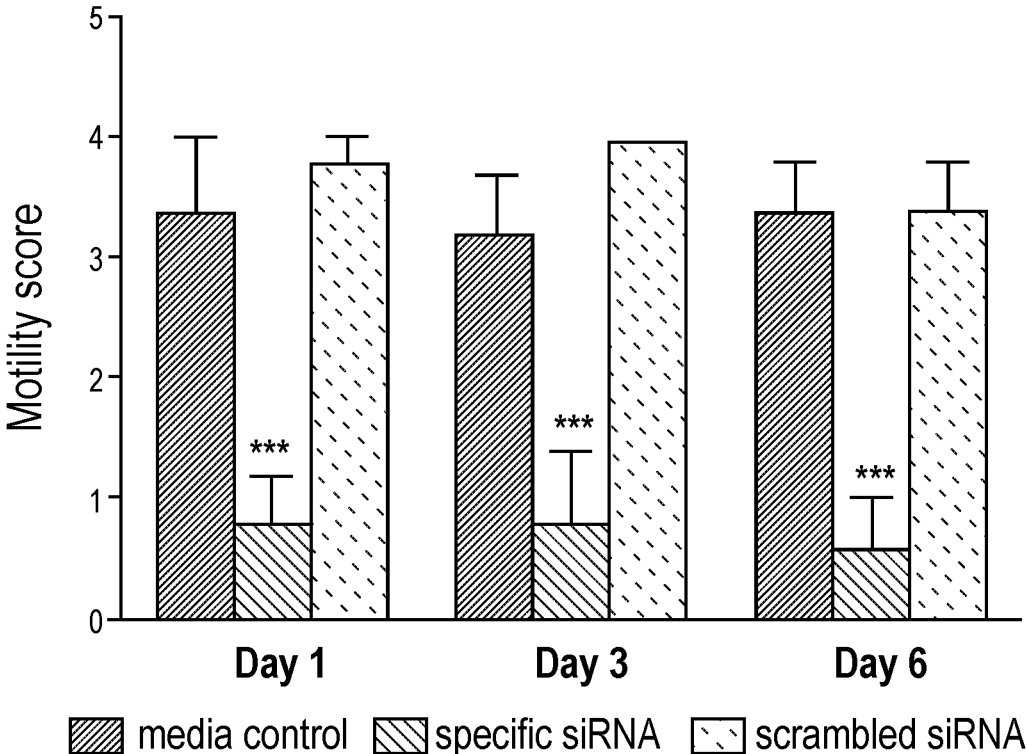
FIGS. 4A, 4B, and 4C depict the results of a UGT expression knockdown experiment showing a UGT expression knockdown-dependent decrease in worm motility, microfilariae release, and metabolism. UGT knockdown in female *B. malayi* adult worms caused reductions in motility (FIG. 4A), microfilariae release per worm per 24 hour period (FIG. 4B), and metabolism as measured by MTT reduction relative to the media control (FIG. 4C) at 1, 3, and 6 days post-siRNA treatment.

At day 1 post-siRNA incubation, a 77.1% reduction in motility was observed with the Bma-iUGT siRNA-treated group compared to the scrambled control (p=0.0006, FIG. 4A). This dramatic reduction in motility was maintained through day 6 (78.94% reduction, p=0.0004).

Figure 4B:
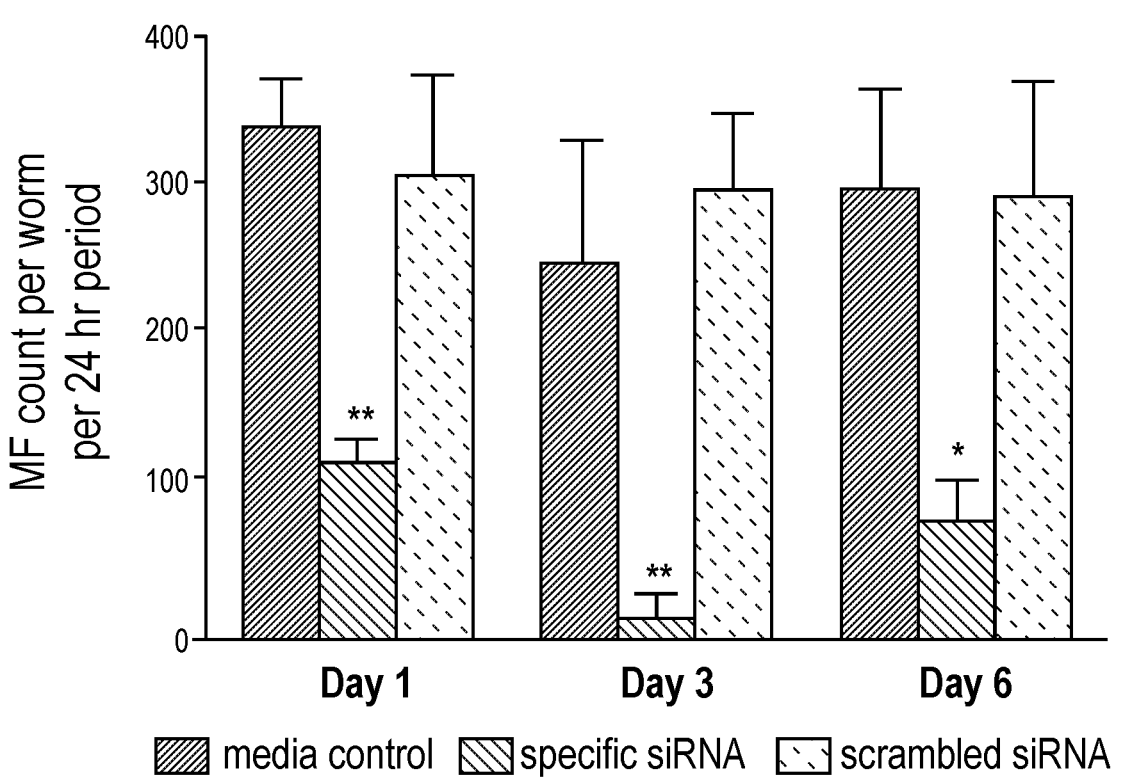

A dramatic decrease in microfilariae release per adult worm per 24-hr period after Bma-iUGT knockdown was also observed. At day 1, there was a 62.52% reduction from the specific siRNA-treated worms compared to the scrambled siRNA-treated group (p=0.0048, FIG. 4B). The greatest reduction in microfilariae release occurred at day 3 and was marked by a 95.25% difference between the Bma-iUGT siRNA group and the scrambled control (mean number of microfilariae release in 24 h=14 vs 294.8, p=0.0096).

Figure 4C:
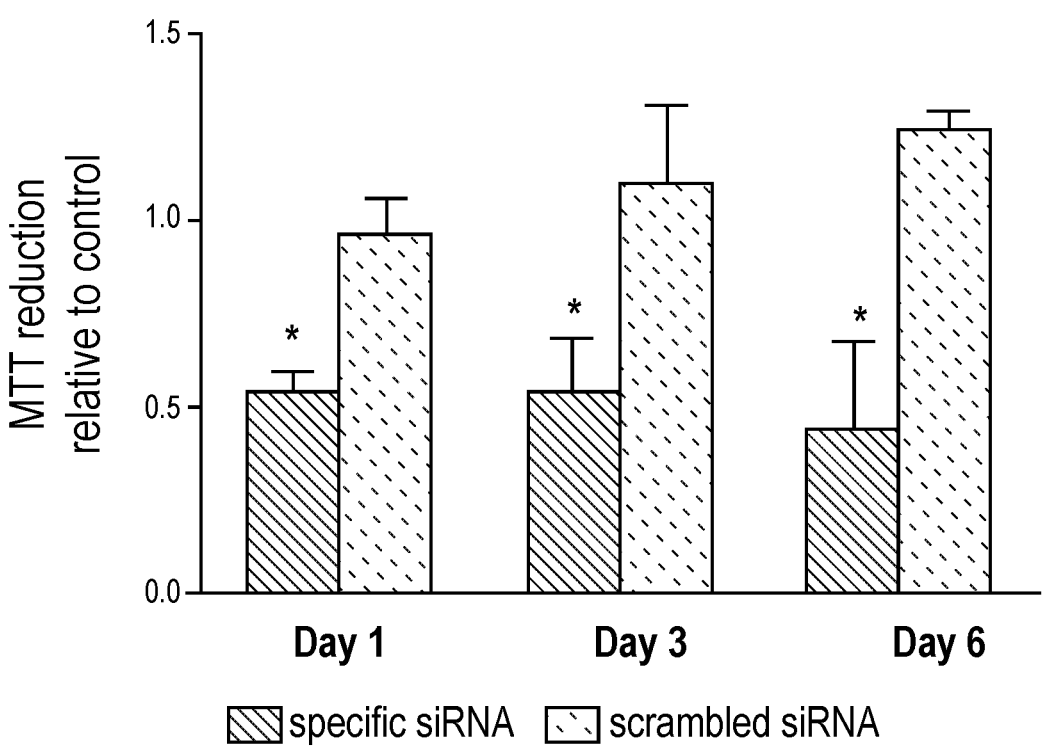

Decreased MTT reduction by the Bma-iUGT siRNA treated B. malayi was observed at all three timepoints (FIG. 4C). The values observed were similar over the course of the experiment with day 6 post-siRNA incubation showing the greatest difference (64.2%, p=0.0243) between the specific and scrambled siRNA groups.

These results indicate that UGT is an essential protein for B. malayi adult worm survival in vitro.

Example 4: Treatment with UGT Inhibitors Exhibits Macrofilaricidal Activity In Vitro The dramatic decrease in worm viability and fecundity after siRNA inhibition demonstrated that Bma-iUGT is an essential protein for adult B. malayi survival. In view of these findings, the effects UGT inhibitors on adult worm survival were evaluated. Non-specific UGT inhibitors for activity against B. malayi adult worms were tested in vitro. Both of these agents, sulfinpyrazone and probenecid, are FDA-approved medications that are used to treat gout. (Domenjoz R., Annals of the New York Academy of Sciences, 1960; 86(1):263-91; Uchaipichat et al., Drug Metab Dispos., 2006; 34(3):449-56; Cunningham et al., Clin. Pharmacokinet., 1981; 6(2):135-51; Uchaipichat et al., Drug Metab Dispos., 2004; 32(4):413-23).

Adult B. malayi worm incubation with UGT inhibitors: UGT inhibitors, sulfinpyrazone (ChemCruz, Santa Cruz Biotechnology, Dallas, TX, US) and probenecid (Invitrogen, Carlsbad, CA, US), were evaluated for macrofilaricidal activity in vitro. Sulfinpyrazone was resuspended in 1×PBS (pH 7.4) while probenecid was resuspended in deionized water. When testing sulfinpyrazone, adult B. malayi female worms were incubated in culture media with the drug for 8 days at concentrations of 2500 μM, 1000 μM, 200 μM, 40 μM, and 8 μM. For probenecid, adult female worms were incubated in culture media with the drug for 7 days at concentrations of 5000 µM, 500 µM, 250 µM, and 100 µM. Worms were transferred into new media with corresponding drug concentrations every other day. As a negative control, worms were incubated in culture media alone. Worm motility was scored using the previously mentioned scale described in Example 3 for the course of the experiment.

*B. malayi* microfilariae incubation with UGT inhibitors: The above UGT inhibitors were evaluated for microfilaricidal activity in vitro. For each drug, experiments were performed in triplicate at a concentration of $2 \times 10^4$ Mf/mL in culture media. Viability was determined by quantifying the number of motile larvae from 100 randomly selected microfilariae per well. The concentrations used for sulfinpyrazone were 2500 µM and 200 µM while the concentrations used for probenecid were 5000 µM and 500 µM. As a negative control, larvae were incubated in culture media alone. The UGT inhibitor experiments were repeated two times under similar conditions.

UGT Inhibitor Cytotoxicity Assay: Cytotoxicity of the UGT inhibitors was measured using a Pierce LDH Cytotoxicity Assay Kit (Thermo Fisher Scientific, Carlsbad, CA, US). HEK cells were seeded at $5 \times 10^4$ per well in DMEM (Quality Biological, Gaithersburg, MD, US) with 10% Hyclone Cosmic Calf Serum (Thermo Fisher Scientific, Carlsbad, CA, US), 200 µM of L-glutamine (Quality Biological, Gaithersburg, MD, US), and 50 µg/mL of gentamicin (Quality Biological, Gaithersburg, MD, US) at 37° C. in 5% $CO_2$. The cells were then incubated with various concentrations of the UGT inhibitors overnight. Following this, 50 µL of media was transferred from each well to a new 96-well plate and then added 50 µL of reaction buffer. The mixture was incubated for 30 minutes and then added 50 µL of stop solution. Absorbance was measured at 490 nm and 680 nm. The following controls were included in the experiment: a spontaneous lactate dehydrogenase (LDH) activity control that was incubated with the vehicle only and a maximum LDH activity control that was incubated with nothing but later lysed prior to incubation with the reaction buffer. Absorbance was calculated for each well by subtracting the 680 nm absorbance value (background) from the 490 nm absorbance value. Percent cytotoxicity was calculated using the following equation (Formula 1):

$$\% \text{ Cytotoxicity} = \qquad (1)$$

$$\frac{(UGT \text{ inhibitor } LDH \text{ activity} - \text{Spontaneous } LDH \text{ actvity})}{(\text{Maximum } LDH \text{ activity} - \text{Spontaneous } LDH \text{ activity})}$$

Figure 5A:
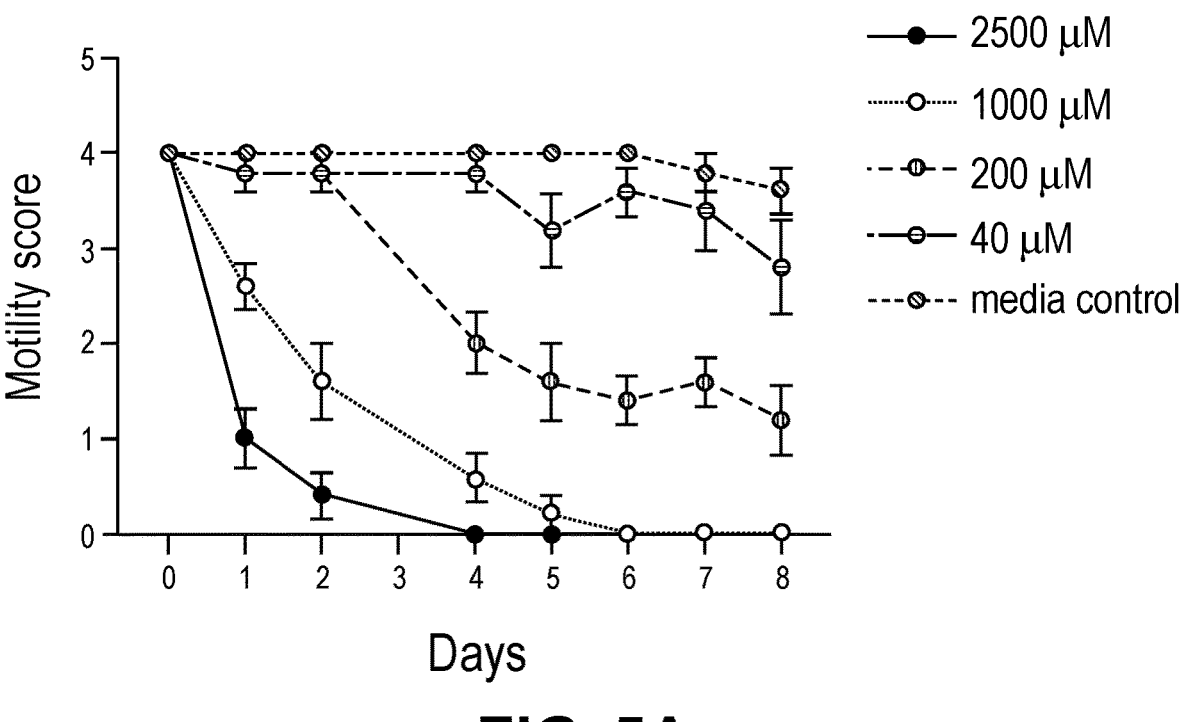
FIGS. 5A, 5B, 5C, and 5D depict macrofilaricidal activity of UGT inhibitors incubated in vitro with adult *B. malayi* worms, including motility scores of adult *B. malayi* adult worms after incubation with various concentrations of sulfinpyrazone (FIG. 5A) and probenecid (FIG. 5B), and percent survival of *B. malayi* microfilariae incubated with sulfinpyrazone (FIG. 5C) and probenecid (FIG. 5D).

Results: For sulfinpyrazone, a dose-response relationship was observed for macrofilaricidal activity in vitro (FIG. 5A). The most rapid decline in adult worm motility occurred at 2500 µM. At this concentration, the area under the curve (AUC) was 3.6 and significantly different than the AUC of 31.6 for the control worms incubated with media alone (p<0.0001). Macrofilaricidal activity was also seen at 200 µM. The AUC at this concentration was 19.7 and significantly different (p<0.0001) than the AUC for media control.

Figure 5B:
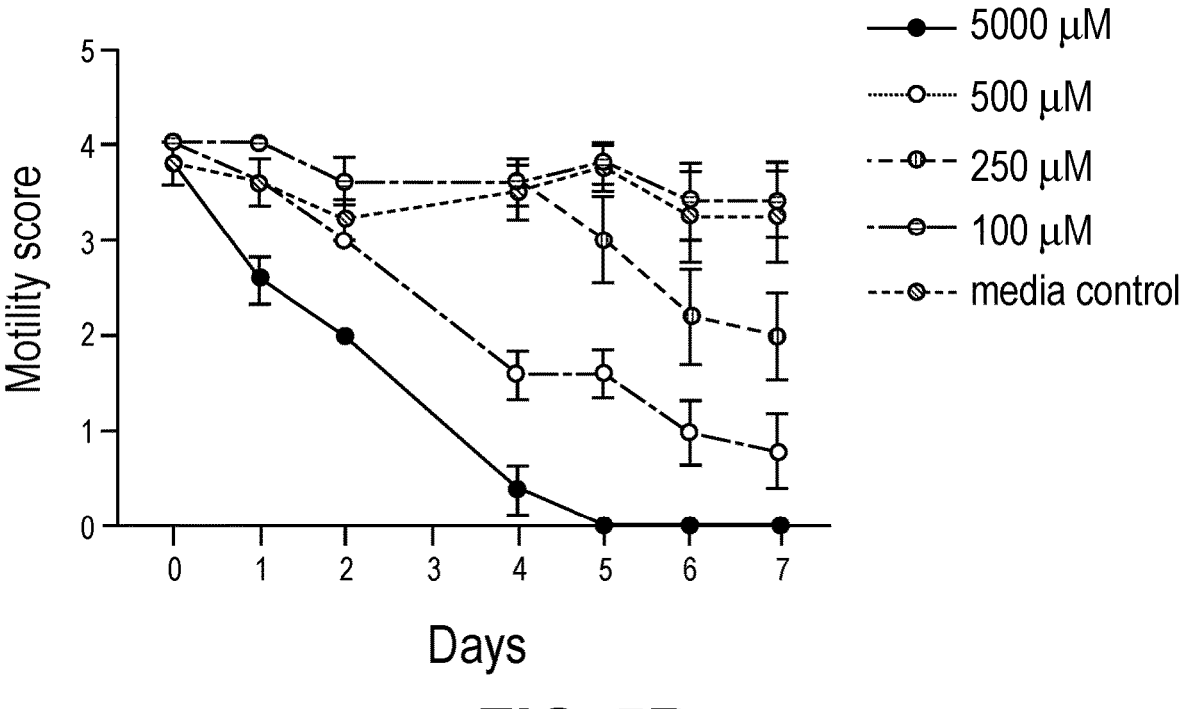

For probenecid, a dose-response curve was also observed for macrofilaricidal activity in vitro (FIG. 5B). The greatest reduction in worm motility occurred at 5000 µM, which had an AUC of 8.1 (p<0.0001) compared to the media control AUC of 24.18. The lowest concentration that exhibited a significant effect on motility was 500 µM (p=0.0004). Though worm motility at 250 µM was not significantly different over the course of the experiment, at day 7 there was a significant difference (p=0.0105) between the treatment group compared to the control. While these drugs are FDA-approved, it was desirable to determine whether the concentrations used were cytotoxic. Employing a lactate dehydrogenase (LDH) cytotoxicity assay with human embryonic kidney (HEK) cells, no cytotoxicity was detected at the concentrations that exhibited macrofilaricidal activity. (See, Table 3).

TABLE 3

| Sulfinpyrazone | | Probenecid | |
|---|---|---|---|
| Concentration | % Cytotoxicity | Concentration | % Cytotoxicity |
| 2000 µM | −4.14 | 5000 µM | −2.49 |
| 100 µM | −4.46 | 500 µM | −1.34 |
| 200 µM | −5.35 | 250 µM | −.67 |
| 40 µM | −4.03 | 100 µM | −2.69 |

Figure 5C:
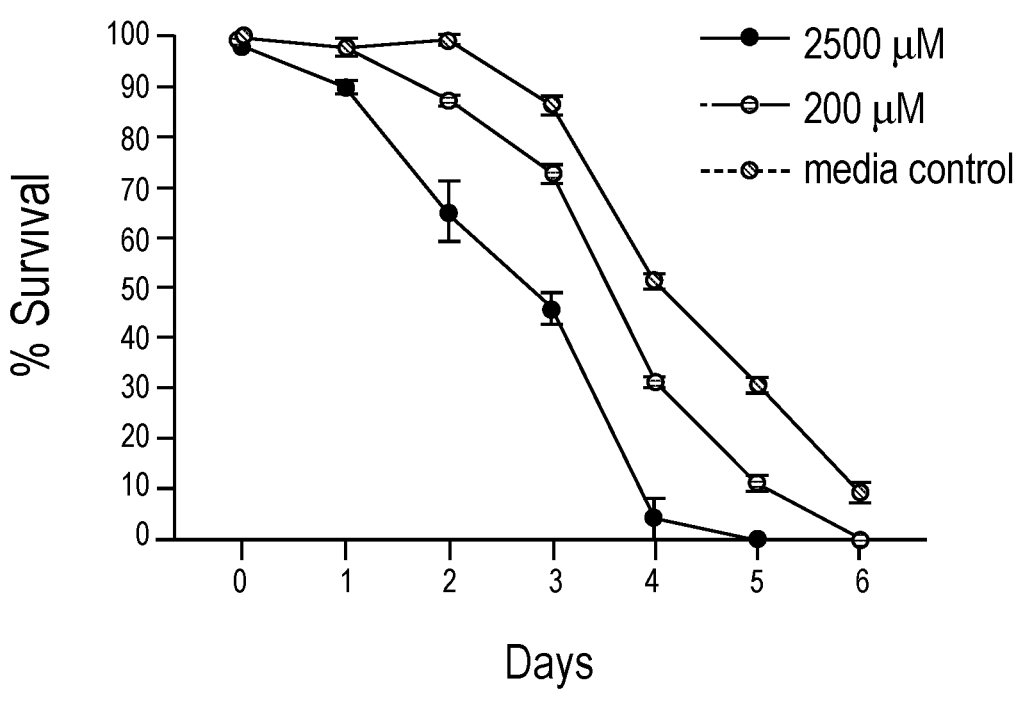
Figure 5D:
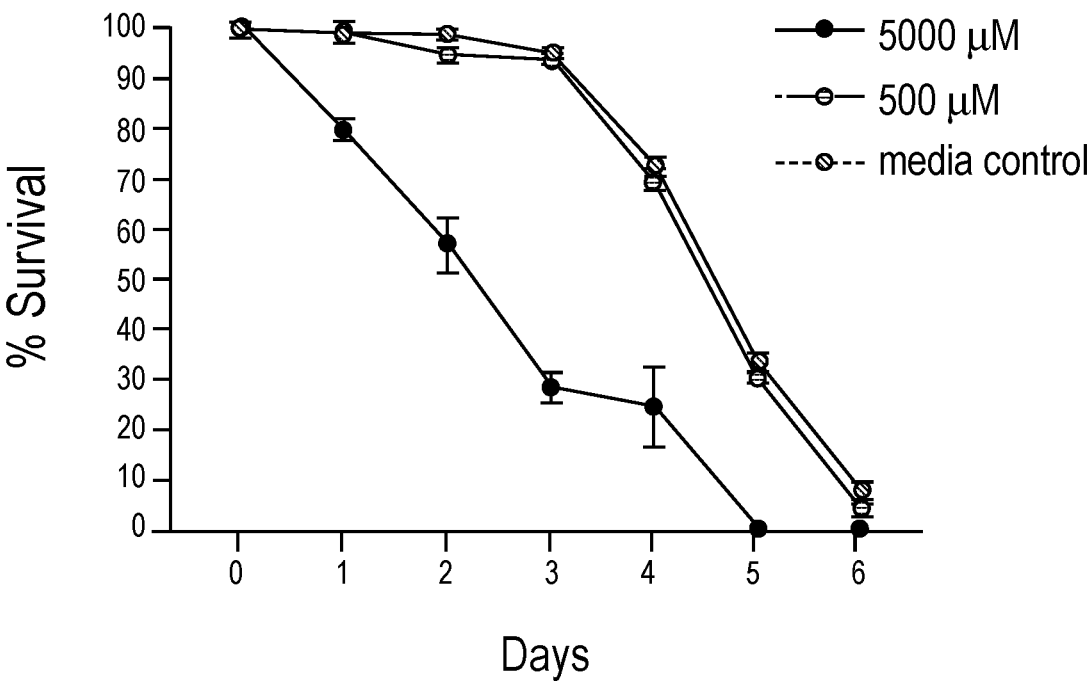

After testing the drugs on adult filariae, microfilaricidal effect was examined. Some microfilaricidal effects were observed at the highest concentrations for both drugs (FIGS. 5C-D). However, no clear microfilaricidal effect was demonstrated for probenecid at 500 µM and very little for sulfinpyrazone at 200 µM.

Both drugs, sulfinpyrazone and probenecid, exhibited macrofilaricidal activity in vitro. The lowest effective concentration for sulfinpyrazone was 200 µM. A previous study investigating sulfinpyrazone showed a maximum concentration (Cmax) in humans of 79.9 µM for a 400 mg dose. (See, Rosenkranz et al., *Eur. J. Clin. Pharmacol.*, 1983, 24(2): 231-5). These data indicate that sulfinpyrazone could serve as a new therapeutic approach against adult filariae. The data indicate similar conclusions for probenecid, which demonstrated robust macrofilaricidal activity in vitro at 500 µM. A significant reduction in motility was observed by day 7 at 250 µM probenecid suggesting that this concentration may be effective at killing adult worms if given over a longer time course. In context of physiological relevance, one pharmacokinetic study showed the peak concentration in humans given a single 2 g oral dose of probenecid to be 148.6 µg/mL (520.7 µM) with minimal adverse events. (See, Selen et al., *J. Pharm. Sci.*, 1982; 71(11):1238-42). Based on these in vitro data, this concentration would rapidly kill adult filarial worms.

Example 5: Treatment with UGT Inhibitors in Combination with an Anthelmintic Exhibits Synergistic Macrofilaricidal Activity in Adult *Brugia* Worms In Vitro Recently, a study showed that overexpression of the ugt-22 gene in *C. elegans* imparts significant resistance to albendazole, a known anthelmintic drug. (See, Fontaine et al., *Int. J. Parasit. Drugs Drug Resist.*, 8(2):312-319, 2018). This finding, along with past studies that showed that albendazole is glycosylated in nematodes indicate that UGT proteins may be involved in the metabolism of albendazole. (See, Laing et al., *Biochem. J.*, 432(3):505-514, 2010; Vokral et al., *Parasit.*, 139(10):1309-1316, 2012; and Vokral et al., *Vet. Parasitol.*, 196(3-4):373-381, 2013). The following experiment was designed to investigate whether the above-identified UGT inhibitors, sulfinpyrazone and probenecid, affects albendazole's ability to kill adult helminths. Surprisingly, unexpectedly strong synergistic responses in reduction of adult female *Brugia* motility were observed with both combinations of sulfinpyrazone/albendazole and probenecid/albendazole.

Adult female *B. malayi* incubation with sulfinpyrazone and abendazole, or probenecid and albendazole: Combinations of the above-described UGT inhibitors, sulfinpyrazone (ChemCruz, Santa Cruz Biotechnology, Inc., Dallas, TX, US) or probenecid (Invitrogen, Carlsbad, CA, US), with albendazole (Sigma-Aldrich, St. Louis, MO, US) were evaluated in vitro for macrofilaricidal activity. Sulfinpyrazone and albendazole were individually resuspended in 1×PBS (pH 7.4) while probenecid was resuspended in deionized water. When testing sulfinpyrazone, adult *B. malayi* female worms were incubated in culture media with the drug for 8 days at concentrations of 40 µM alone or in combination with 10 µM of albendazole. For the probenecid samples, adult female worms were incubated in culture media with the drug for 8 days at concentration of 100 µM alone or in combination with 10 µM of albendazole. Worms were transferred into new media with corresponding drug concentrations every other day. As a negative control, worms were incubated in culture media alone. Worm motility was scored using a previously established scale as described in Example 3 for the course of the experiment.

Figure 6A:
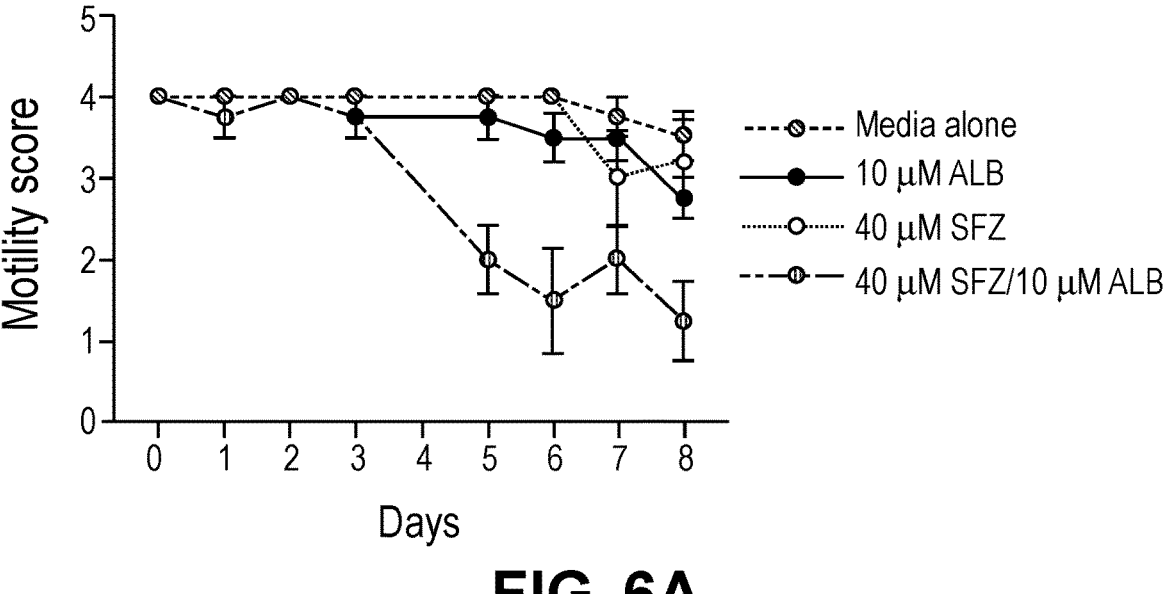
FIGS. 6A and 6B depict the effect of a combination of UGT inhibitor, sulfinpyrazone or probenecid, with an anthelmintic (albendazole) on decrease in worm motility. Female adult *B. malayi* worms were incubated in vitro with either sulfinpyrazone, albendazole, or sulfinpyrazone and albendazole together.

Results: Adult *Brugia* females were incubated with 40 µM sulfinpyrazone in combination with 10 µM albendazole in vitro for 8 days. The filaria were evaluated based on motility, producing an area under the curve (AUC) of 22.5 for incubated with sulfinpyrazone and albendazole together (FIG. 6A). This was significantly lower than the AUC produced by adult worms cultured in 10 µM of albendazole alone (AUC=29.63, p=0.0007, FIG. 6A). Limited macrofilaricidal activity was observed in worms treated with albendazole (10 µM) or sulfinpyrazone (40 µM) alone, compared to worms cultured in media alone (FIG. 6A). Thus, a combination of sulfinpyrazone with the anthelmintic albendazole produced a statistically significant greater than additive response in decreasing motility of the adult worms, indicating a surprising and unexpected synergistic effect was achieved with this combination of active agents.

Figure 6B:
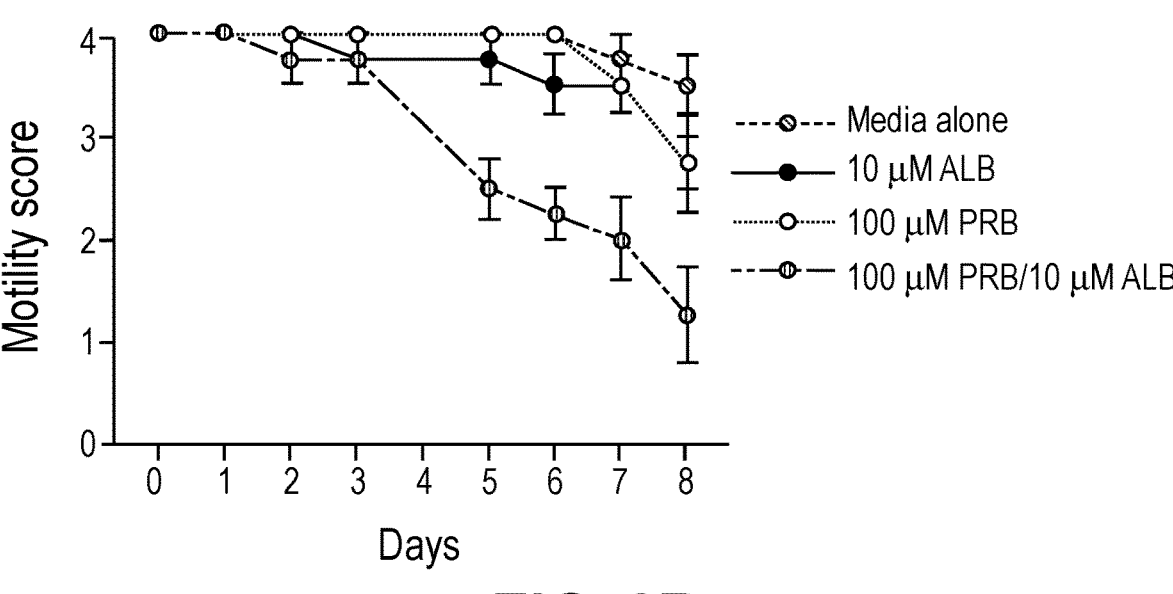

Separately, adult *Brugia* females were incubated with 100 µM probenecid in combination 10 µM albendazole in vitro for 8 days. The resultant plot from the combined incubation with probenecid and albendazole produced an AUC of 24, which was significantly lower (p=0.0022) than the AUC observed when worms were incubated in 10 µM of albendazole alone (FIG. 6B). Surprisingly, a combination of probenecid with the anthelmintic albendazole also produced a greater than additive response in decreasing motility of the adult worms. A surprising synergistic effect in decreasing adult worm motility was observed when incubating the adult worms with the two active agents, probenecid and albendazole, together.

Example 6: Serum from Filarial Patients does not Contain IgG and IgE Antibodies Specific for Bma-iUGT A major obstacle for helminth vaccine development is the potential for individuals living in endemic countries to possess pre-existing antigen-specific IgE and therefore be at risk for developing allergic reactions when vaccinated. (Diemert et al., *J. Allergy Clin. Immunol.,* 2012; 130(1):169-76 e6). In this study a luciferase immunoprecipitation system assay (LIPS) was employed to determine whether individuals infected with filariae developed Bma-iUGT-specific antibodies. A Bma-iUGT-luciferase fusion protein was incubated with serum from microfilaremic patients, filarial patients with chronic pathology, endemic normals, and tropical pulmonary eosinophilia patients. Serum from blood bank donors was used as a negative control. Bma-iUGT peptide antibodies raised in New Zealand rabbits was used as the positive control.

Generation of Ruc-antigen fusion proteins: A Bma-iUGT-*Renilla reniformis* luciferase (Ruc) fusion protein in a pREN2 vector was obtained from Genscript Biotech Corporation (Piscataway Township, New Jersey, US). The Bma-iUGT signal sequence as predicted by signalP was removed prior to synthesis. A pREN2 vector was amplified in TOP10 cells (Thermo Fisher Scientific, Carlsbad, CA, US) on agarose plates with kanamycin 50 µg/mL. Midiprep kit (Qiagen, Hilden, Germany) was used to isolate and purify the plasmid DNA per the manufacturer's guidelines. The Bma-iUGT-Ruc plasmid (30 µg) was transfected into $1 \times 10^6$ 293F cells (Thermo Fisher Scientific, Carlsbad, CA, US) per mL. Bma-iUGT-Ruc fusion proteins were prepared 72 hrs later from lysate of transfected 293F cells and stored at −80° C. for later use.

Luciferase immunoprecipitation system: Antibody titers were measured using a luciferase immunoprecipitation system (LIPS) assay. (Burbelo et al., *BMC Biotechnol.,* 2005; 5:22; Burbelo et al., *J. Clin. Microbiol.,* 2008; 46(7):2298-304; Drame et al., *MBio.,* 2016; 7(1):e02132-15). For IgG and IgE quantification, serum was diluted to 1:100 and 1:10 respectively in 50 µL of LIPS master mix (20 mM Tris pH 7.5, 150 mM NaCl, 5 mM MgCl2, 1% Triton X-100) and $1 \times 10^6$ light units (LU) of the UGT-Ruc fusion protein with PBS-T added to bring the reaction to 100 µL. The LIPS mixture was incubated in a 96-well polypropylene plate for 10 minutes at room temperature. For antigen-antibody purification, 5 µL of a 50% suspension of Ultralink protein A/G (Pierce Chemical Company, Rockford, IL, US) or Ultralink anti-human IgE beads (Thermo Fisher Scientific, Carlsbad, CA, US) in PBS was added to a 96-well high throughput screening filter plate (MilliporeSigma, Burlington, MA, US). The antigen-antibody mixture was then added to each well and incubated for 15 minutes at room temperature. A vacuum was applied to the bottom of the filter plate. The retained protein-antibody-bead complex was washed with 200 µL of LIPS master mix twice and with PBS once. The LU were measured with a Bethold LB 960 Centro microplate luminometer with 50 µL of coelenterzine solution (Promega Corp., Madison, WI, US). For these experiments, samples were run in duplicate, and the calculated LU was adjusted for the measured LU of UGT fusion protein without serum.

Figures 7A, 7B:
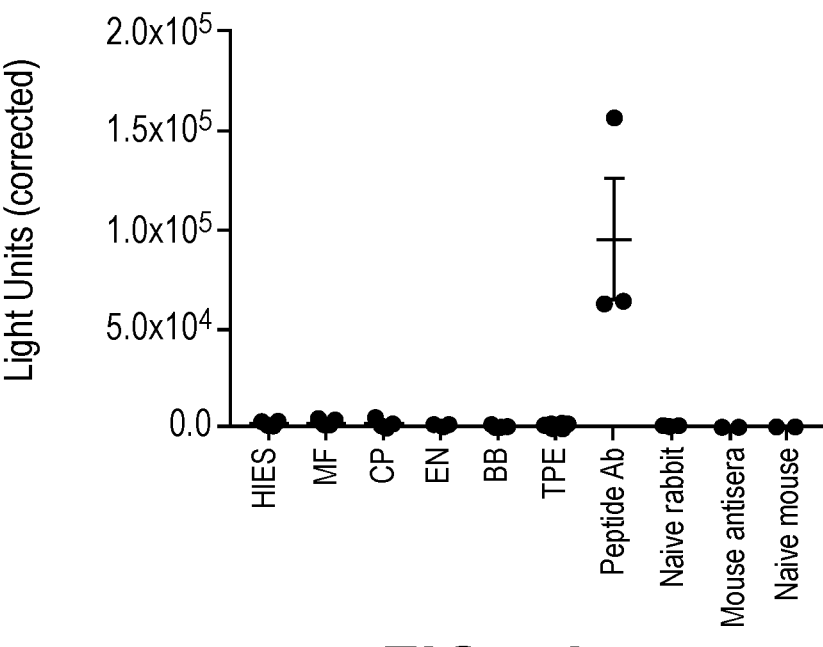
FIGS. 7A and 7B show that serum of filaria-infected individuals does not contain detectable IgG or IgE specifically recognizing UGT. Filarial patient serum was incubated with a UGT-luciferase fusion protein. No detectable IgG (FIG. 7A) and IgE (FIG. 7B) was measured using the LIPS assay. The UGT peptide rabbit polyclonal antibodies served as a positive control for the detection of IgG. HIES=hyper IgE syndrome, MF=microfilaremic, CP=chronic pathology, EN=endemic normal, BB=blood bank donors, TPE=tropical pulmonary eosinophilic, Peptide Ab=UGT peptide polyclonal antibodies.

The LIPS assay did not detect any Bma-iUGT-specific IgG (FIG. 7A) or IgE (FIG. 7B) in any of the serum samples from filaria patients. There was no detected specific IgG or IgE in serum from U.S. blood bank donors, while the Bma-iUGT peptide IgG antibodies recognized our fusion protein. These results indicate that UGT does not elicit an antibody response during natural infection.

Example 7: Bma-LAD-2 siRNA Treatment Reduces LAD-2 mRNA and Protein Expression in Adult Worms Experiments were also conducted to evaluate the effects of reducing mRNA and protein levels in *B. malayi* worms incubated with siRNA targeted to Bma-fukutin, Bma-serpin, Bma-shtk, Bma-reprolysin, Bma-peptidase, Bma-egf-like-02820, Bma-egf-like-48010, and Bma-LAD-2.

The BLOCK-iT™ RNAi Designer was employed to select the siRNA duplexes for gene silencing activity and specificity (Invitrogen, Carlsbad, CA, US). The siRNA sequence with the greatest probability of success was selected for each target, and for some targets, multiple sequences were selected to best ensure knockdown. Life Technologies (Carlsbad, CA, US) synthesized the target-specific siRNA (Bma-lad-2, Bma-fukutin, Bma-shtk, Bma-serpin) and purified the complexes by standard desalting methods. Similarly, other target-specific siRNAs (Bma-egf-like-02820, Bma-egf-like-48010, Bma-peptidase, Bma-re-prolysin) were obtained through GE Healthcare Dharmacon, Inc. (Lafayette, CO, US). The 5'-3' siRNA sequences used in this experiment are as follows:

```
Bma-LAD-2 siRNA 1
sense:
                            (SEQ ID NO: 20)
5' GCAAGUACUACCAUACUAUdTdT 3' antisense:
                            (SEQ ID NO: 21)
5' AUAAGUUGGAAUUCGUUGCdTdT 3'

Bma-LAD-2 siRNA 2
sense:
                            (SEQ ID NO: 22)
5' GCGCAUAUCGCAAGUAAAUdTdT 3' antisense:
                            (SEQ ID NO: 23)
5' AUUUACUUGCGAUAUGCGCdTdT 3'

Bma-LAD-2 siRNA 3
sense:
                            (SEQ ID NO: 24)
5' GCGAAUAGUCGAUACCUAAdTdT 3' antisense:
                            (SEQ ID NO: 25)
5' UUAGGUAUCGACUAUUCGCdTdT 3'

Bma-Fukutin siRNA 1
sense:
                            (SEQ ID NO: 26)
5' CCACCCATTTCGCAGATTT 3' antisense:
                            (SEQ ID NO: 27)
5' AAAUCUGCGAAAUGGGUGGdTdT 3'

Bma-Fukutin siRNA 2
sense:
                            (SEQ ID NO: 28)
5' GGAGCGAGAGTGAATGGAAdTdT 3' antisense:
                            (SEQ ID NO: 29)
5' UUCCAUUCACUCUCGCUCCdTdT 3'

Bma-Fukutin siRNA 3
sense:
                            (SEQ ID NO: 30)
5' GCTAACGTTGCAAATTATTdTdT 3' antisense:
                            (SEQ ID NO: 31)
5' AAUAAUUUGCAACGUUAGCdTdT 3'

Bma-ShTK siRNA 1
sense:
                            (SEQ ID NO: 32)
5' GCGCCTTCTACAGCAGTAAdTdT 3' antisense:
                            (SEQ ID NO: 33)
5' GCGCCUUCUACAGCAGUAAdTdT 3'

Bma-ShTK siRNA 2
sense:
                            (SEQ ID NO: 34)
5' GGUGGUAUGAAUAGCAUAAdTdT 3' antisense:
                            (SEQ ID NO: 35)
5' UUAUGCUAUUCAUACCACCdTdT 3'

Bma-ShTK siRNA 3
```

```
-continued
sense:
                            (SEQ ID NO: 36)
5' GCUAAAGAACUAUGCGCUAdTdT 3' antisense:
                            (SEQ ID NO: 37)
5' UAGCGCAUAGUUCUUUAGCdTdT 3'

Bma-Serpin siRNA
sense:
                            (SEQ ID NO: 38)
5' GGAUUUCGAGUGAGACAAAdTdT 3' antisense:
                            (SEQ ID NO: 39)
5' UUUGUCUCACUCGAAAUCCdTdT 3'

Bma-EGF-like-02820 siRNA
sense:
                            (SEQ ID NO: 40)
5' GUAUCGAGGGCAAGGGAAAdTdT 3' antisense:
                            (SEQ ID NO: 41)
5' UUUCCCUUGCCCUCGAUACdTdT 3'

Bma-EGF-like-48010 siRNA
sense:
                            (SEQ ID NO: 42)
5' GCAACAAAUGCAAGAAUAAdTdT 3' antisense:
                            (SEQ ID NO: 43)
5' UUAUUCUUGCAUUUGUUGCdTdT 3'

Bma-Peptidase siRNA 1
sense:
                            (SEQ ID NO: 44)
5' AGGAAAGGUUGUUAGGAUAdTdT 3' antisense:
                            (SEQ ID NO: 45)
5' UAUCCUAACAACCUUUCCUdTdT 3'

Bma-Reprolysin siRNA 3
sense:
                            (SEQ ID NO: 46)
5' GGAUAAUGUGAAAGGAAUAdTdT 3' antisense:
                            (SEQ ID NO: 47)
5' UAUUCCUUUCACAUUAUCCdTdT 3'
```

After observation of Bma-LAD-2 siRNA entry into the intestine as described in Example 1, gene and protein expression was evaluated by quantitative reverse transcription PCR (RT-qPCR) and Western blot respectively. cDNA was generated using mRNA isolated from filariae cultured in media alone, Bma-LAD-2 siRNA, and scrambled siRNA for 1 day and 6 days post-siRNA incubation. Using Taqman primers, *B. malayi* lad-2 gene expression was quantified and normalized to Bma-gapdh.

siRNA treatment of *B. malayi* female adult worms: *B. malayi* female adult worms were treated with siRNA as described above in Example 2. For each time point, 5 adult female worms were incubated for 24 hrs in an equal mixture of the siRNAs (Bma-LAD-2, Bma-Fukutin, Bma-ShTK, Bma-Serpin) or one siRNA (Bma-EGF-like-02820, Bma-EGF-like-48010, Bma-Peptidase, Bma-Reprolysin) at a total concentration of 5 µM in 850 µL of media in a 5000 MWCO Pur-A-Lyzer™ dialysis tube (Sigma-Aldrich, St. Louis, MO, US). Following the 24-hour incubation worms were extracted from the dialysis tubes and evaluated 1 day post-incubation for transcript knockdown, worm motility, MTT reduction, and microfilariae release. For Bma-lad-2, the worms 6 days post-siRNA incubation were later evaluated.

RNA extraction and analysis of RNA levels by RT-qPCR: RNA was extracted from the siRNA-treated worms as described above in Example 2. The following Taqman primer and internal probes were used:

```
Bma-gapdh:
Forward primer:
                             (SEQ ID NO: 48)
5' TTGATCTCACTTGCCGACTC 3'

Reverse primer:
                             (SEQ ID NO: 49)
5' TGGTCTTCGGTGTATTCCAA 3'

Internal probe:
                             (SEQ ID NO: 50)
5' CAGCTAATGGACCGATGAAGGGGA 3'

Bma-lad-2:
Forward primer:
                             (SEQ ID NO: 51)
5' GTGATCCACGGCTTACGATT 3'

Reverse primer:
                             (SEQ ID NO: 52)
5' CAGGCACATCAAGCACAGTT 3'

Internal probe:
                             (SEQ ID NO: 53)
5' TGCTCGTGGCTTTCATTCAGGA 3'

Bma-fukutin:
Forward primer:
                             (SEQ ID NO: 54)
5' AGGTTATTTCATGTGCCCTGC 3'

Reverse primer:
                             (SEQ ID NO: 55)
5' ATTCCATTCACTCTCGCTCCA 3'

Internal probe:
                             (SEQ ID NO: 56)
5' AGGCGGATTACGGTAATTGGCGAGT 3'

Bma-shtk:
Forward primer:
                             (SEQ ID NO: 57)
5' TGCACTGATCCAATGGCAAA 3'

Reverse primer:
                             (SEQ ID NO: 58)
5' GTTACTGCTGTAGAAGGCGC 3'

Internal probe:
                             (SEQ ID NO: 59)
5' TGCGCCAAAACATGTGGATTTTGCGG 3'

Bma-serpin:
Forward primer:
                             (SEQ ID NO: 60)
5' ACGTGCGCAGTTAGACTTTG 3'

Reverse primer:
                             (SEQ ID NO: 61)
5' GCCTCTGCGATATAAGCCAA 3'

Internal probe:
                             (SEQ ID NO: 62)
5' GCGGACGGTGAAACGAAGCAGCA 3'

Bma-egf-like-02820:
Forward primer:
                             (SEQ ID NO: 63)
5' GCTTACACGGTGGCAGAAAA 3'

Reverse primer:
                             (SEQ ID NO: 64)
5' AAGCCACCTATCTGCTCTCC 3'

Internal probe:
```

```
-continued
                             (SEQ ID NO: 65)
5' TCGAGGGCAAGGGAAAACTGGAA 3'

Bma-egf-like-48010:
Forward primer:
                             (SEQ ID NO: 66)
5' ACCTGGCTTCATGGGAGAAA 3'

Reverse primer:
                             (SEQ ID NO: 67)
5' CTTCACCACAGTCGCAAACA 3'

Internal probe:
                             (SEQ ID NO: 68)
5' TGCTGCCGGTCTTATGGGCG 3'

Bma-peptidase:
Forward primer:
                             (SEQ ID NO: 69)
5' CAGCCATTATTGGCCAGGAC 3'

Reverse primer:
                             (SEQ ID NO: 70)
5' AAATGAAGTGGTGCCGCATT 3'

Internal probe:
                             (SEQ ID NO: 71)
5' AGCCTTCCAACTTGGTTCATCCCAACA 3'

Bma-reprolysin:
Forward primer:
                             (SEQ ID NO: 72)
5' TGGAACACAGTGATCAGGCT 3'

Reverse primer:
                             (SEQ ID NO: 73)
5' AACGGCATTCCACTTATCG 3'

Internal probe:
                             (SEQ ID NO: 74)
5' CCCATTTCGTGTGCAATAGTTGCAGCA 3'
```

Generation anti-Bma-LAD-2 polyclonal antibodies: For the Western blot analysis, polyclonal anti-Bma-LAD-2 peptide antibodies were generated by GenScript (Piscataway Township, NJ, US). Rabbits were immunized with Bma-LAD-2 peptide sequences conjugated to keyhole limpet hemocyanin (KLH). The peptide sequences used are as follows: CYEKDEHLIAEGRPN (SEQ ID NO:75), DSTG-SKLAKTVKIDC (SEQ ID NO:76), and CGQIANFDPYGRKMS (SEQ ID NO:77). To facilitate binding to KLH, cysteines were added at either the N- or C-terminus of the peptides.

Western blot analysis of Bma-LAD-2: The Western blot analysis was carried out as described in Example 2, except that after the overnight blocking, the membrane was incubated with 1:7000 anti-LAD-2peptide antibodies (GenScript, Piscataway Township, NJ, US) and 1:1000 rabbit anti-β actin antibodies (Abcam, Cambridge, UK) for 1 hr.

Figures 8A, 8B:
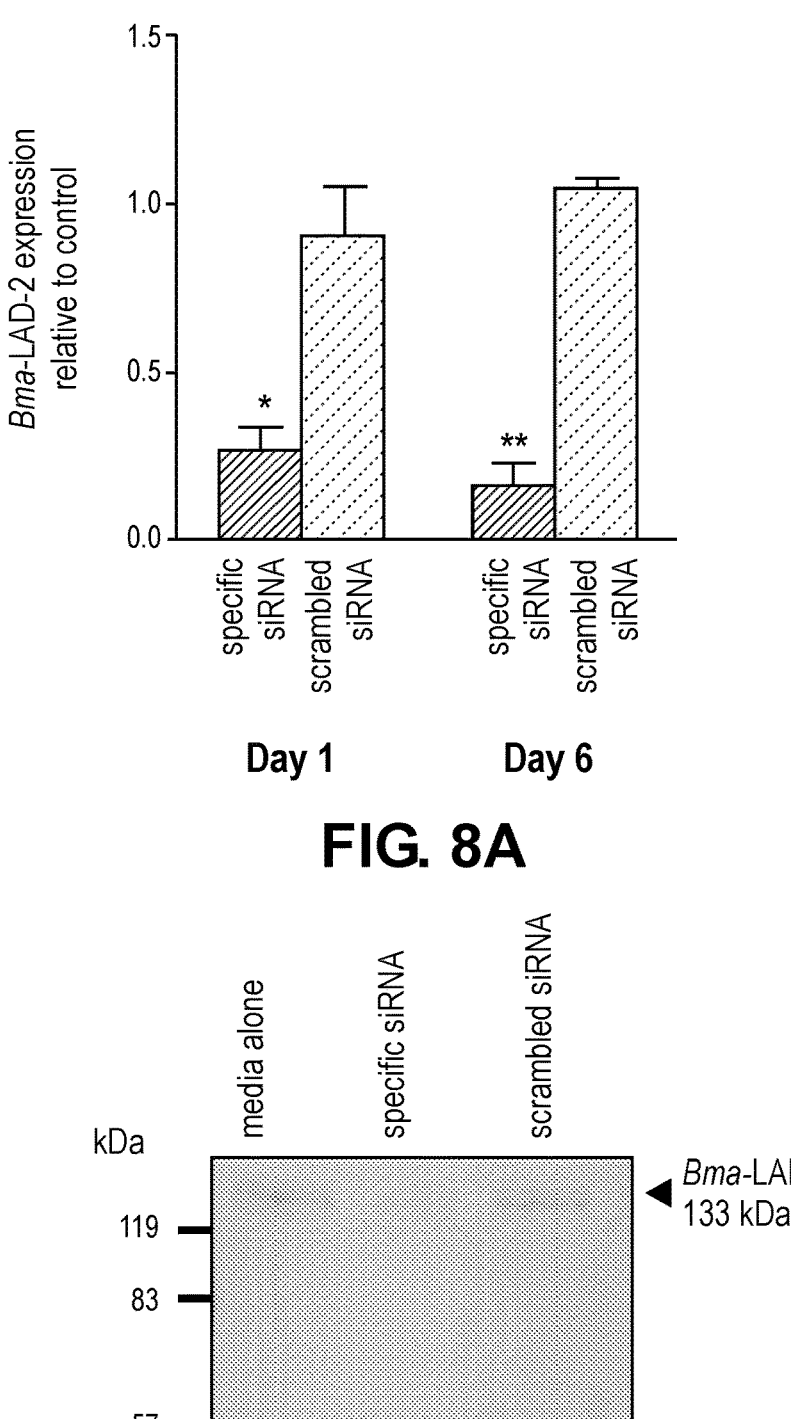
FIGS. 8A, 8B, 8C show that incubation of adult *B. malayi* with Bma-LAD-2-specific siRNA reduces target transcript and protein levels. Adult female worms were incubated with Bma-LAD-2-specific siRNA, scrambled siRNA, or media alone. Target mRNA levels in the specific siRNA and scrambled siRNA treated groups were measured by RT-qPCR relative to the media control with glyceraldehyde 3-phosphate dehydrogenase (GAPDH) as a normalization control.
Figure 8C:
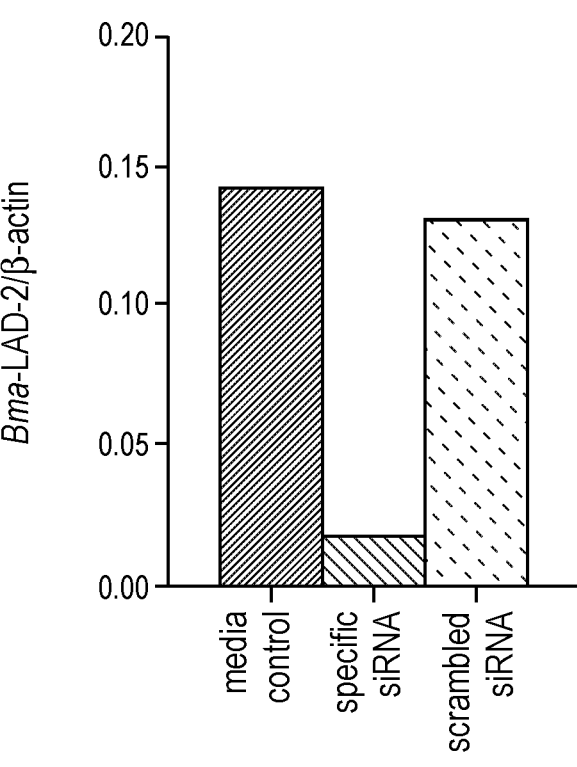

Results: Of the eight gene targets investigated in this study, only Bma-lad-2 exhibited a statistically significant response to siRNA inhibition. Particularly, a 70.42% decrease was observed in Bma-lad-2 transcript levels (FIG. 8A) in worms treated with target specific siRNA (mean=0.2662) compared to the scrambled siRNA-treated filariae (mean=0.9) relative to the media control group at 1 day post-siRNA incubation. This decrease in transcript levels grew to 87.02% by 2 days post-siRNA incubation (FIG. 8A). Bma-LAD-2 protein expression was visualized by Western blot (FIG. 8B) in worms treated with specific or scrambled siRNA for 24 hrs and then cultured in media for an additional 24 hrs. The protein was detected using polyclonal antibodies raised in New Zealand rabbits against recombinant Bma-LAD-2. A dramatic decrease in Bma- LAD-2 expression was observed in the specific siRNA-treated worms compared to the controls. There was a robust reduction in Bma-LAD-2 protein expression with the Bma-LAD-2 siRNA treated worms compared to controls normalized to β-actin (87% reduction in Bma-LAD-2/β-actin) (FIG. 8C).

Example 8: Reduced Worm Viability and Fecundity in Bma-LAD-2 siRNA-Treated Adult Filariae The effects of Bma-LAD-2 knockdown on worm motility, microfilariae release, and metabolism (MTT reductions assay) were evaluated, as described above in Example 3.

Statistical analysis: The siRNA experiments for Bma-LAD-2 were repeated twice under the same conditions. The worm motility and microfilariae release data was analyzed by one-way analysis of variance (ANOVA) using statistical package in PRISM 7.0 (GraphPad, La Jolla, CA, US). Validity of the one-way ANOVA was verified by performing individual comparisons of mean values using Tukey's multiple comparisons test. For the gene expression and MTT reduction data, a T-test was used to determine significance. The p values for each experimental and control group was designated as follows: * for p values<0.05,  for p values<0.01, and * for p values<0.001.

Figure 9A:
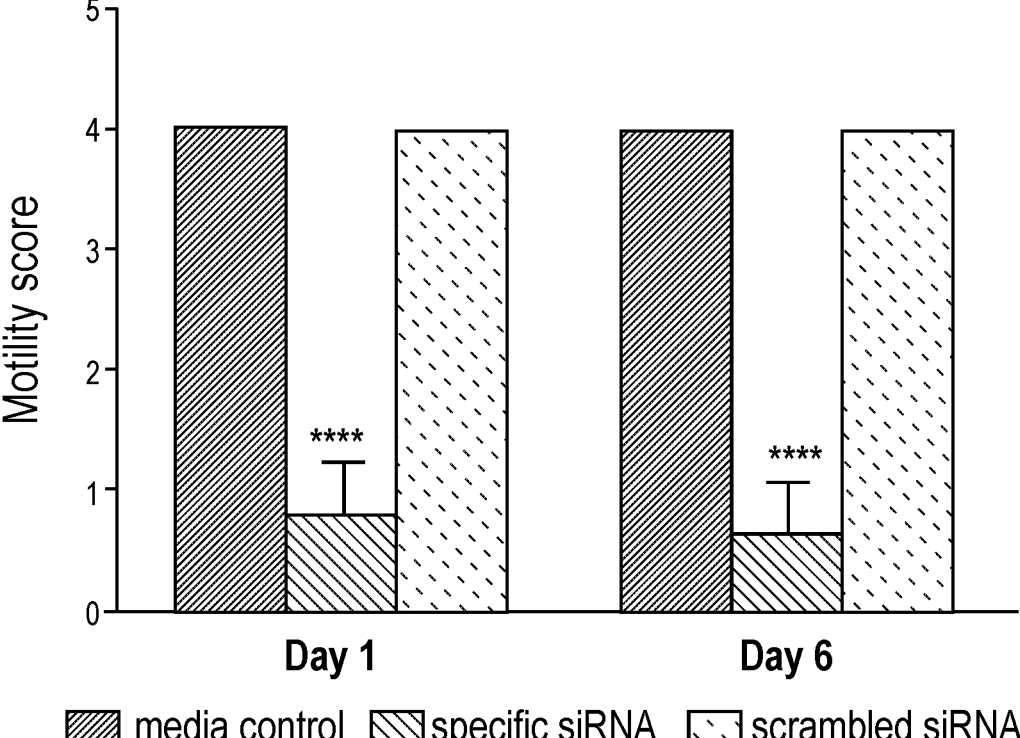
FIGS. 9A, 9B, and 9C depict the results of a Bma-LAD-2 expression knockdown experiment showing a Bma-LAD-2 expression knockdown-dependent decrease in worm motility, microfilariae release, and metabolism. Bma-LAD-2 knockdown in female *B. malayi* adult worms caused reductions in motility (FIG. 9A), microfilariae release per worm per 24 hour period (FIG. 9B), and metabolism as measured by MTT reduction relative to the media control (FIG. 9C) at 1 and 6 days post-siRNA treatment.
Figure 9B:
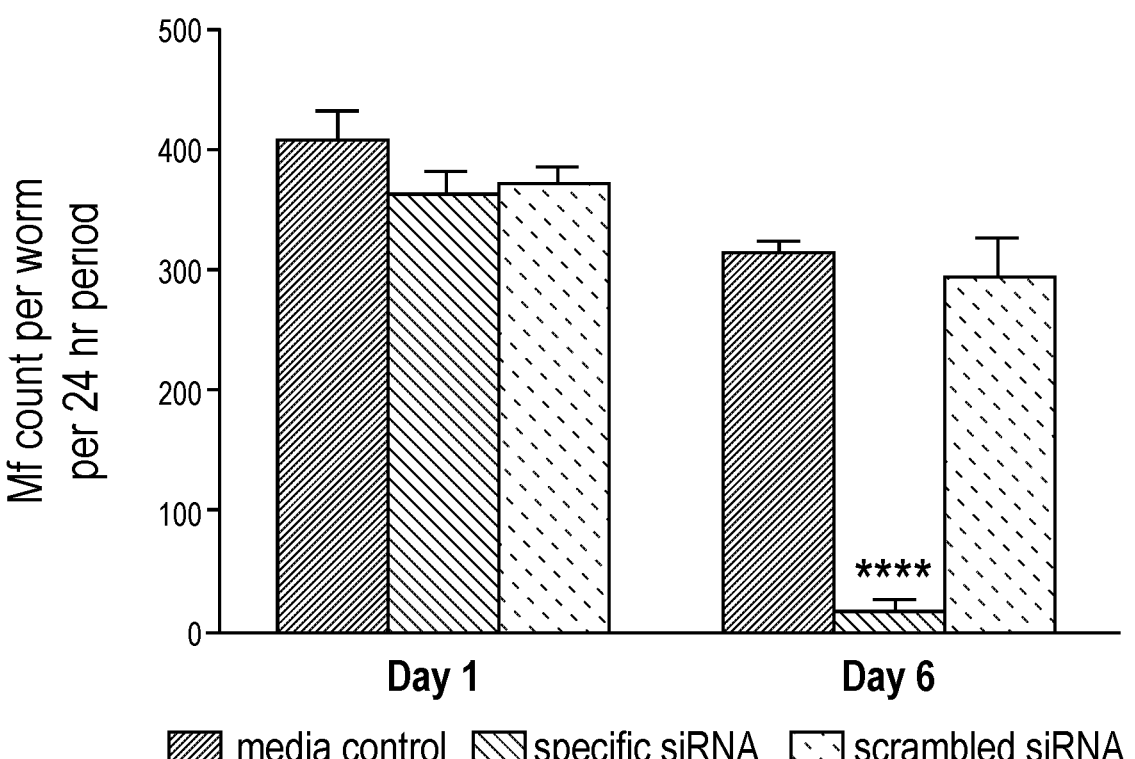
Figure 9C:
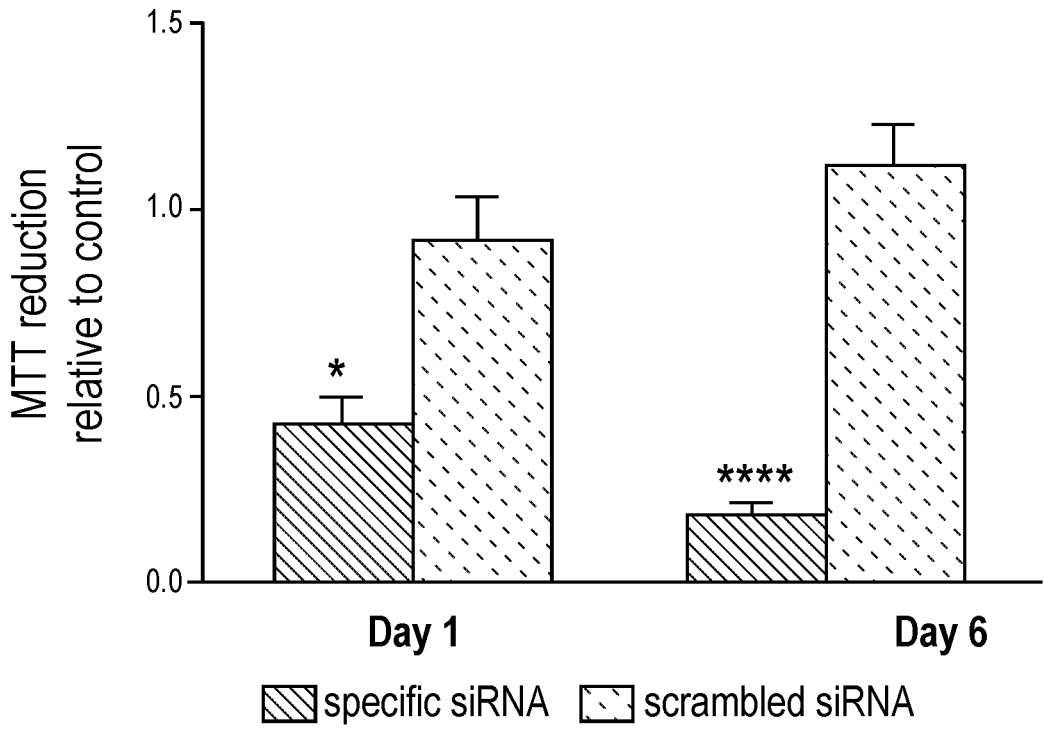

At day 1 post-siRNA incubation, worm motility (FIG. 9A) was significantly reduced (p<0.0001) in worms soaked in Bma-LAD-2 siRNA (mean=0.8) compared to the scrambled control group (mean=4). By day 6 post-incubation, an 85% reduction in motility was observed for the specific siRNA-treated group (mean=0.6) compared to the scrambled siRNA group (mean=4). Mf release was evaluated per adult worm per 24 hr period (FIG. 9B) for each group at timepoints 1 and 6 days post-siRNA incubation. The only significant difference in microfilariae release between the treatment and control groups occurred at day 6. A 93.43% reduction in microfilariae release was observed from Bma-LAD-2 siRNA soaked adult filariae. Finally, two randomly selected adult worms from each group for each timepoint were used for the MTT reduction assay (FIG. 9C). At day 1 post-siRNA treatment, there was a significant reduction (p=0.0139) in MTT reduction by B. malayi treated with target siRNA (mean=0.435) compared to worms treated with scrambled siRNA (mean=0.9303) relative to the media control group. By day 6, a 83.25% decrease in MTT reduction was observed from the Bma-LAD-2 siRNA group.

These results indicate that Bma-LAD-2 is an essential protein for B. malayi adult worm survival in vitro.

Example 9: Transmission Electron Microscopy (TEM) Reveals Ablation of Microvilli in the Intestinal Tract of Bma-LAD-2 siRNA-Treated Adult Filariae Bma-LAD-2 was predicted to be an adhesion protein located at the apical junction of the intestinal tract. Therefore, the structure of the adult filaria intestinal tract was investigated after treatment with Bma-LAD-2 siRNA.

Figure 10A:
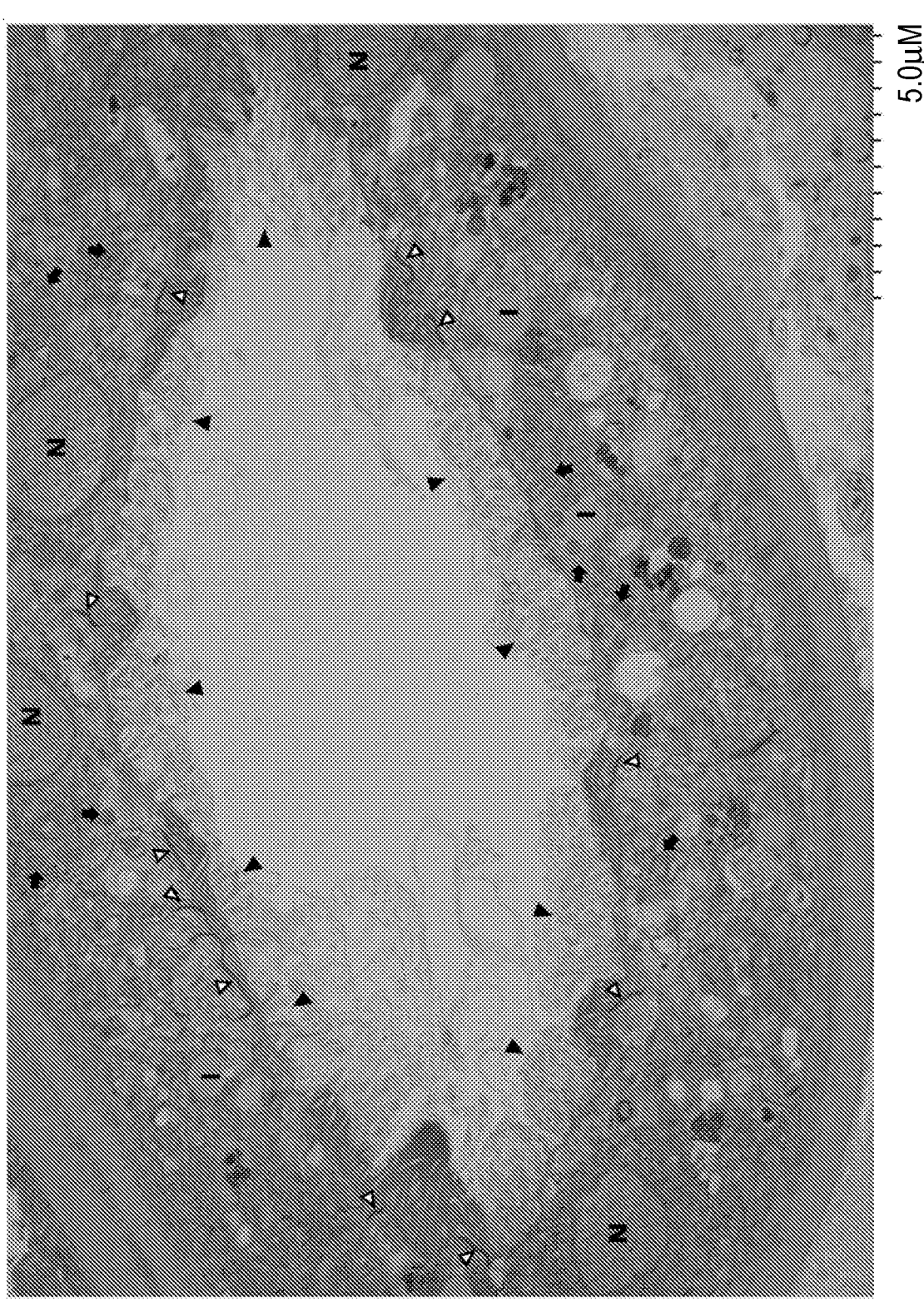
FIGS. 10A and 10B depict the effect of siRNA knockdown of Bma-LAD-2 on the intestinal tract of a *B. malayi* adult worms as captured by transmission electron microscopy (TEM) at 4,000×. Adult filaria were cultured in media alone for 72 hrs and microvilli visualized (FIG. 10A, black arrowhead), showing a lining of microvilli along the apical surface of the intestinal epithelium. Other structures visible are apical junctions (FIG. 10A, white arrowhead), nuclei (FIG. 10A, Nu), lipid droplets (FIG. 10A, L), and mitochondria (FIG. 10A, black arrow). *B. malayi* adult worms were then incubated with Bma-LAD-2 siRNA for 24 hrs and then cultured in media alone for an additional 48 hrs. Upon treatment with Bma-LAD-2 siRNA, there was a robust change in the ultrastructure of the intestine: microvilli (FIG. 10B, black arrowhead) were largely absent from the apical surface of the intestinal epithelium, some vestigial microvilli are observed to be invaginated by the surrounding epithelium, and many mitochondria (FIG. 10B, black arrow) appear to have unraveled cristae. Other structures visible are apical junctions (FIG. 10B, white arrowhead), nuclei (FIG. 10B, Nu), and lipid droplets (FIG. 10B, L).
Figure 10B:
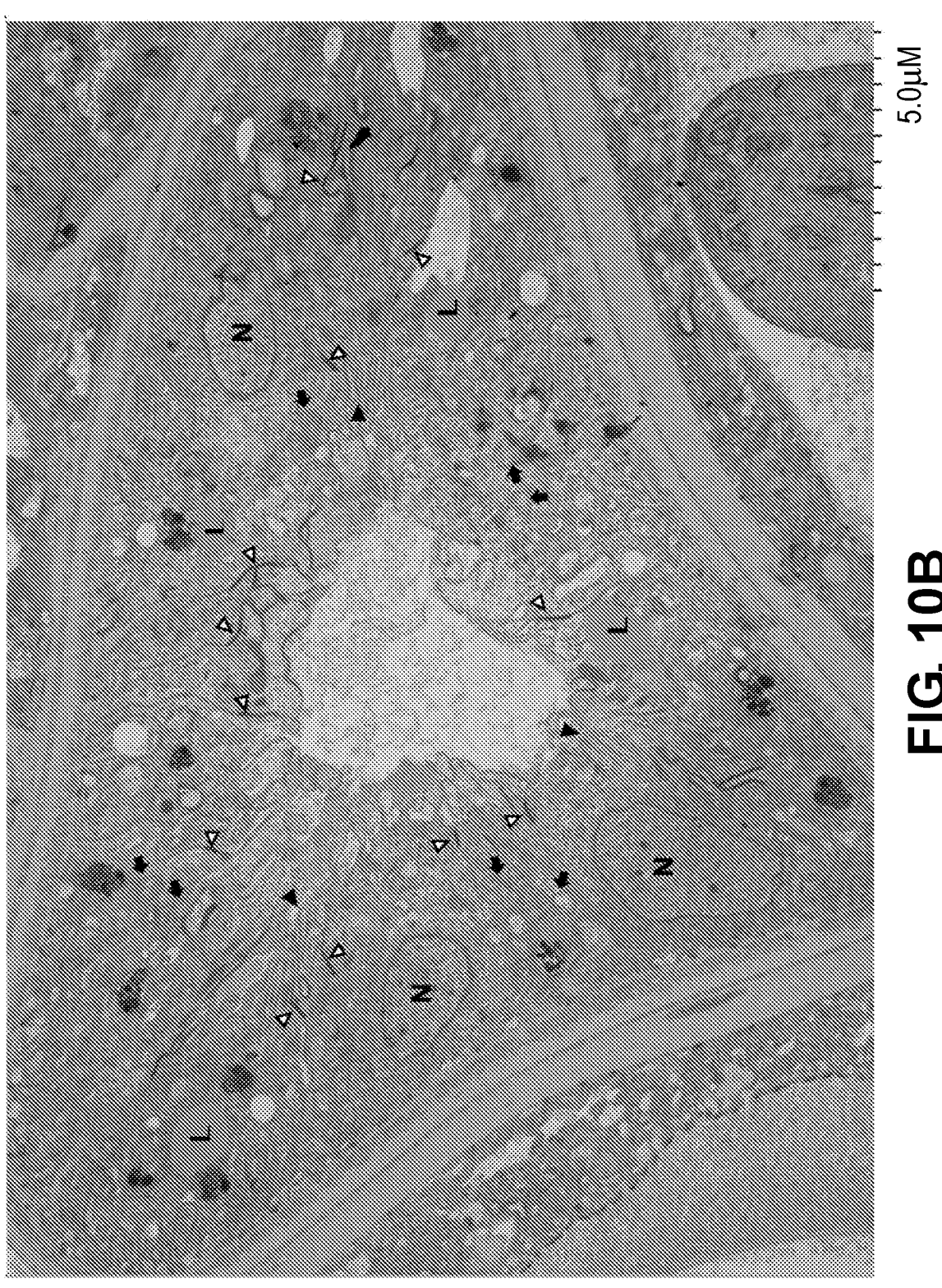

By TEM, microvilli lining the epithelium of the intestinal tract of normal B. malayi adults were visualized (FIG. 10A). Upon treatment with Bma-LAD-2 siRNA, there was a robust change in the ultrastructure of the intestine (FIG. 10B). Near complete ablation of the microvilli was observed in the intestine of the treated worms. In addition, many of the apical junctions in the intestinal tract of treated worms appeared shortened suggesting the loss of adhesion molecules. Many of the mitochondria in the treated worms also appeared to possess unraveled cristae.

In this study, a significant decrease in worm motility, metabolism, and microfilariae release was observed when Bma-LAD-2 expression was knocked down. Evidence indicates that L1CAMs play an integral role in the maintenance and formation of apical junctions in nematodes. Therefore, it is likely that the reduction in Bma-LAD-2 signaled a loss of cell-to-cell contact in the epithelial cells. Studies have shown that such a loss of L1CAM signal can arrest cell proliferation and potentially induce apoptosis. (Ben et al., Exp Ther Med., 2014; 7(4):785-90; Schafer et al., Oncogene, 2013; 32(2):180-9). This would explain the ablation of microvilli in the intestine of Bma-LAD-2 siRNA-treated worms as well as the unraveling of the mitochondrial cristae. In addition, the loss of adhesion molecules may have hindered the ability of the apical junction to prevent diffusion of the internal hemolymph into the intestinal lumen.

The observed structural change in the intestinal epithelium could only result in a decrease in worm viability and fecundity if the intestine served an essential role in adult filaria survival. This has been a point of contention with some believing the structure is somewhat expendable. Studies have shown that Brugia worms can absorb some nutrients through their cuticle, casting doubt on whether these filariae need an intestine for digestion. (Scott A L, "Lymphatic-dwelling filariae," London: Imperial College Press, 2000, p. 5-39; Lee D L, "The biology of nematodes," London: Taylor & Francis, 2002, xii, p. 635). However, a previous study of Litomoisoides sigmoiditis, a filarial worm in cotton rats, showed the presence of red blood cells in the filarial gut which implied that adult filariae actively feed. (Attout et al., Parasitology, 2005; 130(Pt 4):421-8). Another study demonstrated that heartworms are able to ingest serum. (McGonigle et al., Int J Parasitol., 2001, 31(13): 1459-66). In addition, the proteomic analysis of different filarial tissue structures performed by our lab revealed that the filarial intestine is enriched in transporters, drug metabolizing enzymes, proteases, protease inhibitors, and adhesion molecules. (Morris et al., PLoS Negl Trop Dis., 2015; 9(9):e0004054). These findings suggest that the gut is used for not only nutrient digestion and uptake but also waste metabolism and disposal; functions essential in any living organism.

Example 10: No Detectable Bma-LAD-2 Specific IgG or IgE in Serum from Filarial Patients As noted above, a major obstacle for helminth vaccine development is the potential for individuals living in endemic countries to possess pre-existing antigen-specific IgE and therefore be at risk for developing allergic reactions when vaccinated. (Diemert et al., J Allergy Clin Immunol., 2012, 130(1):169-76 e6). Thus, as discussed above in Example 5 for UGT, serum from filaria-infected individuals was examined using a LIPS assay to see if it contained IgE that recognizes Bma-LAD-2. In this system, a Bma-LAD-2-luciferase fusion protein was incubated with serum from filarial patients in a 96-well filter plate. Antibody was captured using protein A/G beads for IgG and anti-IgE beads for IgE. Applying a vacuum to the plate left only captured antigen-antibody complexes in the wells. The presence of the fusion protein was detected by adding coelenterazine substrate and then measuring the light units generated.

Ruc-antigen fusion protein: The Bma-LAD-2-*Renilla reniformis* luciferase (Ruc) construct was synthesized using a pREN2 vector by GenScript (Piscataway, NJ, US), as described in Example 5.

Luciferase immunoprecipitation system (LIPS): The LIPS assay was employed to measure antibody titers in serum from filarial patients, as described in Example 5.

Figure 11A:
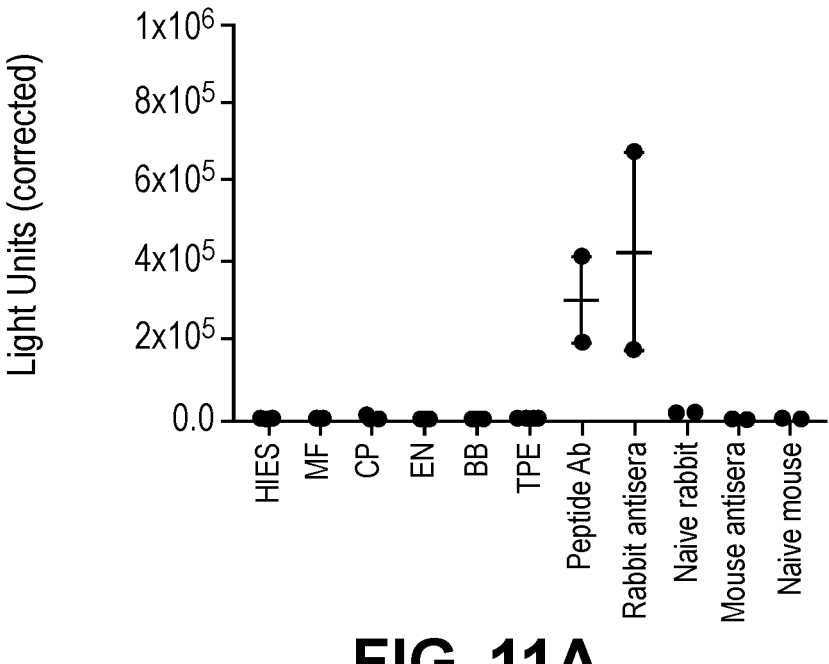
FIGS. 11A and 11B show that serum of filaria-infected individuals does not contain detectable IgG or IgE specifically recognizing Bma-LAD-2. Filarial patient serum was incubated with a Bma-LAD-2-luciferase fusion protein. No detectable IgG (FIG. 11A) and IgE (FIG. 111B) was measured using the LIPS assay. The Bma-LAD-2 peptide rabbit polyclonal antibodies served as a positive control for the detection of IgG. HIES=hyper IgE syndrome, MF=microfilaremic, CP=chronic pathology, EN=endemic normal, BB=blood bank donors, TPE=tropical pulmonary eosinophilic, Peptide Ab=UGT peptide polyclonal antibodies.
Figure 11B:
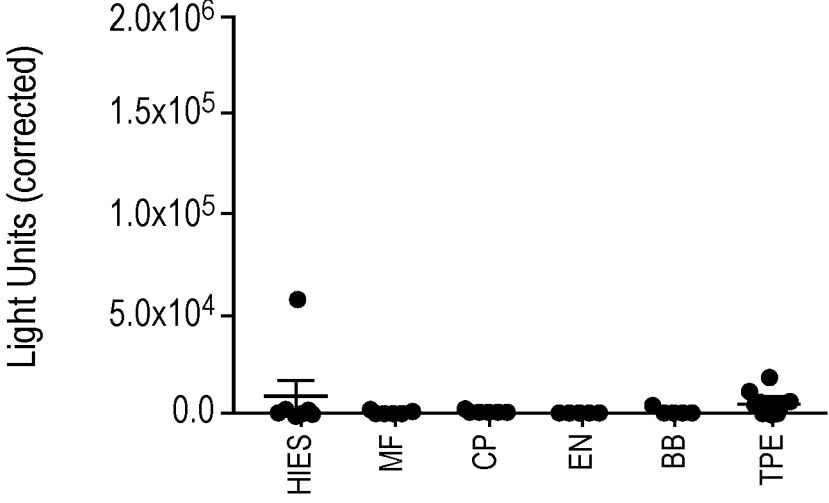

The results showed that filarial patient serum had no detectable pre-existing IgG (FIG. 11A) or IgE (FIG. 111B) against Bma-LAD-2 fusion protein (n=30). Affinity-purified polyclonal antibodies raised in rabbits immunized with recombinant Bma-LAD-2 peptides were used as a positive control, as well as the rabbit anti-sera. There was recognition by the polyclonal antibodies and anti-sera against the fusion protein. This indicated that the fusion protein exhibited the proper conformation and thus the absence of signal in filarial patient samples was due to absence of Bma-LAD-2 specific IgG or IgE. These data indicate that this antigen has a low likelihood of inducing allergic reactions if administered as a vaccine to endemic populations.

Example 11: Adult *B. malayi* Worms are Able to Ingest Antibody

Finally, it was investigated whether adult filarial worms are able to ingest immunoglobulins. Previously, McGonigal et al. demonstrated that *D. immitis* is able to readily ingest fluorescein isothiocyanate (FITC)-conjugated serum. (McGonigle et al., *Int. J. Parasitol.,* 2001; 31(13):1459-66). Polyclonal antibodies against *B. malayi* UGT were generated as described in Example 2. Ten (10) adult *B. malayi* female worms were incubated in cy3-labeled antibody for 24 hrs. Signal was detected in the intestine using fluorescent microscopy.

Labeled antibody was visualized in the intestinal tract of 1 of the 10 adult filarial worms. On repetition of this experiment, uptake of fluorescence into the intestinal tract of 2 of 10 adult filarial worms was observed (not shown). These results demonstrate the capability of adult filariae to ingest antibody. They also suggest that adult filarial worms, at least during in vitro culture conditions, ingest macromolecules into their intestinal tract only intermittently.

---

What is claimed is:

1. A method for preventing or treating a helminth disease in an animal in need thereof, which comprises: administering to the animal a composition comprising a therapeutically effective amount of an inhibitor of UDP-glucoronosyl transferase (UGT), wherein the composition effectively kills adult helminths in the animal but not microfilariae, and the inhibitor of UDP-glucoronosyl transferase (UGT) is sulfinpyrazone or p-(di-n-propylsulphamyl)-benzoic acid (probenecid).

2. The method of claim 1, wherein the helminth disease is a filarial disease.

3. The method of claim 2, wherein the filarial disease is selected from lymphatic filariasis, river blindness, loiasis, or dirofilariasis.

4. The method of claim 1, wherein the helminth disease is caused by an infection of one or more species of *Brugia, Wuchereria, Onchocerca, Loa, Haemonchus*, or *Dirofilaria*.

5. The method of claim 1, wherein the helminth disease is caused by an infection of *Brugia malayi, Brugia timori, Wuchereria bancrofti, Onchocerca volvulus, Loa loa, Haemonchus contortus, Haemonchus placei, Haemonchus similis*, or *Dirofilaria immitis*.

6. The method of claim 1, wherein the helminth disease is caused by an infection of one or more species of *Haemonchus*.

7. The method of claim 6, wherein the helminth disease is caused by an infection of *Haemonchus contortus*.

8. The method of claim 1, wherein the helminth disease is caused by an infection of one or more species of *Dirofilaria*.

9. The method of claim 8, wherein the helminth disease is caused by an infection of *Dirofilaria immitis*.

10. The method of claim 1, wherein the animal is a human, a ruminant animal or other livestock animal, or a companion animal.

11. The method of claim 10, wherein the ruminant animal or other livestock animal is a sheep, a goat, a cow, a llama, a camel, a horse, a mule, a pig, a bird, a rabbit, a deer, an elk, or a giraffe.

12. The method of claim 10, wherein the companion animal is a dog or a cat.

13. The method of claim 1, further comprising administering to the animal an anthelmintic drug in addition to the inhibitor of UGT.

14. The method of claim 13, wherein the anthelmintic drug is albendazole.

15. A method of killing adult helminths in an animal in need thereof, which comprises:

administering to the animal a composition comprising an amount of an inhibitor of UDP-glucoronosyl transferase (UGT), wherein the inhibitor of UGT is sulfinpyrazone or p-(di-n-propylsulphamyl)-benzoic acid (probenecid), wherein the amount is effective to kill adult helminths in the animal, and wherein the adult helminths are not of the species *Haemonchus contortus*.

16. The method of claim 1, wherein the inhibitor of UGT is sulfinpyrazone.

17. The method of claim 1, wherein the inhibitor of UGT is p-(di-n-propylsulphamyl)-benzoic acid (probenecid).

18. The method of claim 15, wherein the inhibitor of UGT is sulfinpyrazone.

19. The method of claim 15, wherein the inhibitor of UGT is p-(di-n-propylsulphamyl)-benzoic acid (probenecid).

* * * * *

SEQUENCE LISTING

```
<160> NUMBER OF SEQ ID NOS: 77

<210> SEQ ID NO 1
<211> LENGTH: 538
<212> TYPE: PRT
<213> ORGANISM: Brugia malayi
<220> FEATURE:
<223> OTHER INFORMATION: B. malayi UGT peptide sequence

<400> SEQUENCE: 1

Met Tyr His Ala Glu Trp Tyr Leu Ala Ser Leu Ile Ile Ile Phe His
1               5                   10                  15

Ala Ser Gln Asn Asp Ser Tyr Lys Ile Leu Val Tyr Asn Pro Arg Phe
            20                  25                  30

Gly Lys Ser His Thr Lys Phe Leu Gly Ser Ile Ala Asp Thr Leu Val
        35                  40                  45

Asn Ala Gly His Asn Val Thr Glu Phe Ala Pro Val Leu Phe Glu Phe
    50                  55                  60

Ser Asp Ser Thr Gly Ser Lys Leu Ala Lys Thr Val Lys Ile Asp Ala
65                  70                  75                  80

Asp Pro Glu Ile Ser Lys Ile Met Asn Val Glu Ile Phe Ala Gln Asp
                85                  90                  95

Ala Trp Lys Arg Asn Gln Gln Ser Ile Phe Ser Leu Ile Ser Val Met
            100                 105                 110

Lys Arg Met Ser Asp Ala Leu Leu Lys Asn Cys Glu Phe Gln Leu Lys
        115                 120                 125

Gln Glu Lys Ile Met Gln Glu Leu Lys Ser Glu Lys Phe Asp Leu Ala
    130                 135                 140

Ile Phe Glu Phe Asn Gln Cys Phe Ala Gly Ile Ile Glu Leu Leu Arg
145                 150                 155                 160

Ile Pro Ala His Ile Val Val Ser Pro Thr Ala Leu Phe Glu Tyr Ala
                165                 170                 175

Ile Glu Cys Phe Gly Ile Pro Asn Ile Pro Ser Tyr Ile Pro Ser Leu
            180                 185                 190

Leu Thr Gln Tyr Thr Asp Lys Met Thr Tyr Leu Gln Arg Leu Lys Asn
        195                 200                 205

Leu Ile Ile Thr Ile Leu Thr Thr Lys Leu Leu Asp Asn His Thr Ile
    210                 215                 220
```

```
Arg Cys Gln Ala Leu Phe Arg Arg Leu Tyr Gly Asp Gln Phe Ile Asp
225                 230             235             240

Leu Lys Glu Lys Leu Ala Gln Val Thr Tyr Val Leu Thr Asn Thr Asp
            245             250             255

Pro Leu Phe His Ile Ser Arg Pro Thr Ile His Lys Met Leu Glu Leu
            260             265             270

Gly Gly Leu Ala Leu Pro Lys Pro Gln Pro Leu Ser Lys Glu Trp Ile
            275             280             285

Ala Val Met Asn Lys Arg Lys Ala Val Val Leu Val Ser Phe Gly Thr
        290             295             300

Val Thr Leu Ser Cys Trp Met Pro Asn Glu Thr Lys Gln Ala Leu Leu
305             310             315             320

Asp Ala Phe Asp Ser Phe Pro Asn Val Thr Phe Ile Trp Lys Tyr Glu
            325             330             335

Lys Asp Glu His Leu Ile Ala Glu Gly Arg Pro Asn Val Ile Thr Ser
            340             345             350

Lys Trp Leu Pro Gln Ser Asp Leu Leu Ala His Lys Asn Leu Ile Ala
            355             360             365

Phe Leu Thr His Gly Gly Met Asn Ser Ile Thr Glu Thr Leu Asn Arg
        370             375             380

Gly Lys Pro Ile Val Val Val Pro Leu Phe Gly Asp Gln Met Gln Asn
385             390             395             400

Ala Val Leu Val Gln Arg Leu Gly Leu Gly Ile Lys Leu Ser Leu Ser
            405             410             415

Glu Leu Ala Ile Lys Glu Lys Ile Lys Asn Ala Ile Tyr Asn Ile Ile
            420             425             430

Tyr Asp Lys Ser Tyr Ala Gln Lys Val Glu Arg Leu Ser Lys Met Met
            435             440             445

Ala Lys Lys Pro Asn Gln Ala Glu Glu Gln Leu Ile Lys His Val Glu
        450             455             460

Phe Ala Ala Glu Phe Gly Gln Ile Ala Asn Phe Asp Pro Tyr Gly Arg
465             470             475             480

Lys Met Ser Phe Val Ser Tyr Tyr Met Leu Asp Ile Ile Ile Pro Phe
            485             490             495

Ile Ile Leu Ile Phe Phe Ile Ile Thr Ile Ile Cys Tyr Leu Ile Ile
            500             505             510

Arg Leu Phe Arg Lys Leu Phe His Lys Ala Val Ile Cys Asn Asn Asn
            515             520             525

Asn Ser Ile Ile Thr Lys Val Lys Lys Asn
        530             535
```

```
<210> SEQ ID NO 2
<211> LENGTH: 1650
<212> TYPE: DNA
<213> ORGANISM: Brugia malayi
<220> FEATURE:
<223> OTHER INFORMATION: B. malayi UGT mRNA sequence

<400> SEQUENCE: 2
gaaagtaatc gaagtatttg gtgctgaaat acaatgtatc atgctgagtg gtatttggct      60
tcactcatta ttatatttca tgcatcacag aatgattcat ataaaatatt ggtatataat     120
ccacgttttg gtaaaagtca caccaaattt ttgggttcaa tcgctgatac attggttaat     180
gccgggcata atgtaaccga gtttgctcct gtactttttg aattttccga ttccactggt     240
```

-continued

```
tctaaattgg ctaaaacagt aaaaatagac gctgatccgg aaatatcgaa aataatgaac    300
gtagaaattt ttgctcaaga tgcatggaaa cgaaatcagc aatccatttt ctcattgatt    360
tcggttatga aacgaatgtc ggatgctctt ctgaagaatt gtgagtttca actaaagcag    420
gaaaaaataa tgcaagaatt gaaatctgaa aagtttgact tagctatctt cgaatttaac    480
caatgctttg ccggaataat tgaattgctt cgtataccgg ctcatattgt cgttagtcct    540
actgctctat ttgaatatgc catagaatgt tttggtatac caaatattcc tagctatatt    600
ccaagtttgc ttacacagta tactgataag atgacatatt tacaacggct gaagaatctc    660
atcataacaa ttttaacgac taaattgctg gataatcata caataagatg tcaagccttg    720
tttcgacgac tttacggcga tcaatttatc gatttgaaag aaaagttagc tcaagtgaca    780
tatgttctca caaatactga tccacttttt cacatctcaa ggccaactat tcacaaaatg    840
ttggaacttg gtggtcttgc cttaccaaaa ccgcaaccgc taagtaaaga atggattgca    900
gtgatgaata aacggaaagc ggtagtgctt gtatcattcg gcaccgttac actgagttgt    960
tggatgccta acgaaactaa gcaagcactt ctagatgcat cgatagtttt tcccaatgtg   1020
acatttatct ggaagtatga aaaagatgag catttaatcg ctgagggacg tccaaacgtg   1080
attacgtcaa aatggcttcc acaatctgat ttgttagcac ataaaaattt gatagcattt   1140
ttgacgcatg gtggtatgaa tagcataacg gaaactttga atcgtggaaa acctattgtt   1200
gtggtaccgc tatttggtga tcagatgcag aatgctgtat tagttcaacg attaggtctt   1260
ggtatcaaat tatccctttc ggaacttgcg ataaagaaa aataaaaaaa tgcaatttat    1320
aatatcatct atgacaaaag ttatgcccaa aaagttgaaa gattatcaaa aatgatggca   1380
aaaaagccta atcaagctga ggaacaactc attaagcatg ttgaatttgc tgcagaattt   1440
ggtcaaatag cgaatttcga cccatacggc agaaaaatgt catttgtatc ttattatatg   1500
cttgatatta tcattccttt tataatactt atattcttta tcattacaat catttgttac   1560
cttatcatta gactattcag aaaattattc cacaaagctg ttatctgtaa taataataat   1620
agtattataa caaaggtgaa aaaaaattaa                                    1650
```

<210> SEQ ID NO 3
<211> LENGTH: 1181
<212> TYPE: PRT
<213> ORGANISM: Brugia malayi
<220> FEATURE:
<223> OTHER INFORMATION: peptide sequence of Bma-LAD -2

<400> SEQUENCE: 3

```
Met Ile Thr Leu Ser Ile Leu Trp Cys Ser Leu Phe Gln Phe Ile Ala
1               5                   10                  15

Phe Ser Arg Thr Leu Gly Pro Pro Lys Leu Asp Pro Glu Asn Gly Gly
            20                  25                  30

Glu Val Trp Phe Gln Val Asn Ser Thr Gly Ile Ala Arg Gly Lys Phe
        35                  40                  45

Ile Leu Pro Cys Tyr Ala Thr Gly Asn Pro Glu Thr Tyr Glu Trp Phe
    50                  55                  60

Lys Asp Gly Glu Lys Leu Lys Val Asp Gly Asp Arg Ile Ala Trp Glu
65                  70                  75                  80

Lys Gln Phe Gln Ser Gly Thr Ile Ile Ile Asn Asp Ala Arg Asp Gly
                85                  90                  95

Asp Gln Gly Tyr Tyr Gln Cys His Ala Ser Asn Ile Phe Gly Ile Ala
            100                 105                 110
```

```
Val Ser Asn Lys Phe His Val Gln Ile Gly Val Leu Asp His Phe Val
    115                 120                 125

Pro Arg Gly Val Arg Arg Leu Ile Val Asp Glu Gly Gln Ser Leu Ser
    130                 135                 140

Ile Arg Cys Asp Ile Pro Tyr Gly Val Pro Lys Pro Ser Val Phe Trp
145                 150                 155                 160

Leu Tyr Arg Asp Thr Gln Arg Thr Asn Met Ile Glu Thr Ile Arg Tyr
                165                 170                 175

Lys His Ile Ala Val Asp Thr Glu Gly Thr Leu His Phe Thr Ala Val
                180                 185                 190

Lys Lys His Asp Gly Arg Gln Asn Leu Ile Tyr Gln Cys Ala Val Thr
                195                 200                 205

Ser Pro Val Leu Arg Gly Glu Tyr Arg Ala Gly Asn Glu Phe Gln Leu
    210                 215                 220

Ile Val Asn Pro Ala Lys Lys Asn Asn Gly Thr Ala Ile His Lys Leu
225                 230                 235                 240

Trp Phe Ser Pro Glu Lys Val Ser Val Lys Val Gly Thr Lys Leu Lys
                245                 250                 255

Leu Met Cys Ile Phe Gly Gly Arg Pro Leu Pro Asn Ile Thr Trp Ser
                260                 265                 270

Lys Leu Asn Asp Asp Leu Pro Leu Ala Arg Leu Lys Asp Phe Lys Ser
                275                 280                 285

Gln Glu Ala Asp Tyr Gly Lys Ala Leu Ile Ile Glu Asn Val Arg Ser
    290                 295                 300

Glu Asp Ala Gly Ile Tyr Glu Cys Arg Ser Gln His Leu Phe His Gln
305                 310                 315                 320

Met His Val Thr Thr Asn Ala Ala Pro Phe Trp Ile Asp Lys Pro Pro
                325                 330                 335

Glu Asp Ile Asp Glu Pro Glu Gly Ser Ser Ala Glu Ile His Cys Thr
                340                 345                 350

Ile Ser Gly Ile Pro Thr Pro Ile Ile Gln Trp Phe Ile Asn Gly Val
                355                 360                 365

Pro Leu His Glu Leu Ala Asp Asn Asp Arg Arg Met Ile Leu Asn Ser
    370                 375                 380

Gly Gln Ile Leu Arg Ile Val Asn Leu Asp His Asp Val Asp Thr Ala
385                 390                 395                 400

Val Tyr Gln Cys Asn Ala Ser Asn Pro Phe Gly Tyr Val Phe Gly Asn
                405                 410                 415

Ala Phe Val Asn Val Arg Ala Tyr Ala Pro Tyr Phe Lys Met Pro Ser
                420                 425                 430

His Arg Ile Trp Asn Val Val Arg Lys Ser Thr Val Glu Met Ser Cys
    435                 440                 445

Asp Val Glu Ala Ala Pro Lys Ala Val Val Lys Trp Val Asp Thr Asn
    450                 455                 460

Asp His Ser Ile Ala Val Val Leu Glu Lys Ile Asn Ile Phe Pro Asn
465                 470                 475                 480

His Thr Leu Arg Ile Ser Gln Val Asn Ser Ala Asp Glu Gly Leu Tyr
                485                 490                 495

Tyr Cys Asn Val Ser Asn Lys Tyr Gly Ile Asn Arg Ala Val Asn Gln
                500                 505                 510

Leu Gln Val Phe Asn Pro Thr His Phe Ile Arg Val Pro Ser Pro Lys
    515                 520                 525

Lys Ser Ile Leu Glu Ala His Glu Ser Val Glu Tyr Val Cys Glu Ala
```

```
          530               535               540

Val Cys Asp Pro Arg Leu Thr Ile Glu Tyr Ser Trp Thr His Asn Gly
545               550               555               560

Ile Pro Ile Asn Asp Ser Val His Phe Lys Leu Leu Asn Asn Ser Leu
                  565               570               575

Leu Ile Val Asn Ala Arg Gly Phe His Ser Gly Thr Ile Asp Cys Ile
                  580               585               590

Val Leu Thr Asp Val Asp Val Lys Ile Ser Gly Ile Glu Leu Thr Val
                  595               600               605

Leu Asp Val Pro Ala Ala Pro Ile Ile Thr Gly Ile Asn Cys Asn Glu
              610               615               620

Arg Arg Ala Met Leu Arg Trp Arg Arg Pro Asp Asp His Gly Asp Gln
625               630               635               640

Ile Lys Gln Phe Leu Ile Gln Met His Thr Glu Phe Glu Glu Gly Leu
                  645               650               655

Trp Gln Thr Val Val Glu Glu Glu Asn Thr Ala Ala Asp Phe Tyr Gln
                  660               665               670

Ala Asp Ile Ala Leu Ser Pro Trp Val Asn Tyr Thr Phe Arg Ile Ile
                  675               680               685

Ala Arg Asn Ser Arg Gly Glu Ser Glu Pro Gly Phe Lys Glu Gly Ile
              690               695               700

Val Cys Ser Thr Lys Ala Tyr Tyr Pro Phe Thr Asn Pro Lys Asp Val
705               710               715               720

Arg Ala Glu Gly Ser Glu Pro Asn Asn Met Ile Ile Glu Trp Lys Pro
                  725               730               735

Met Asp Lys Tyr Asp Trp Asn Gly Pro Gly Leu Gln Tyr Ile Val Arg
                  740               745               750

Tyr Lys Phe Asn Lys Pro Gly Glu Ala Trp Thr Glu Ile Arg Ile Glu
                  755               760               765

Asp Pro Leu Ala Asn Tyr Thr Val Ile Arg Glu Gln Pro Thr Phe Arg
              770               775               780

Glu Tyr Leu Ile Gln Val Glu Ser Leu Asn Ser Phe Gly Arg Ala Val
785               790               795               800

Val Lys Pro Thr Ser Val Lys Gly Tyr Ser Gly Glu Asp Thr Pro Leu
                  805               810               815

Leu Ser Pro Ile Asp Phe Ser Val Ser Glu Phe Ile Asn Cys Thr Ala
                  820               825               830

Val Leu Leu Ile Trp Lys His Val Asp Arg Asp Ser Val Arg Gly His
                  835               840               845

Phe Lys Gly Tyr Leu Ile Asp Tyr Trp Glu Asn Glu Lys Pro Phe Ala
              850               855               860

Ile Met Asn Ala Gly Ala Glu Lys His Lys Asn Glu Thr Ile Leu Tyr
865               870               875               880

Asp Leu Lys Pro Met Thr Asn Tyr Thr Ala Arg Ile Arg Thr Ala Asn
                  885               890               895

Ser Arg Tyr Leu Ser Glu Ser Pro Ser Ile Ile Lys Phe Thr Thr Pro
                  900               905               910

Glu Gly Ile Pro Ser Lys Val His Asn Met Arg Val Arg Ala Val Gly
                  915               920               925

Ala Arg Ser Leu Tyr Val Thr Trp Glu Pro Pro Arg Gln Pro Asn Gly
              930               935               940

Tyr Val Arg Gly Tyr Phe Ile Thr Phe Glu Asn Ser Ser Thr Gly Val
945               950               955               960
```

```
Lys Glu Glu Thr Phe Val Leu Asn Arg Gln Leu Tyr Tyr Leu Asn Glu
            965                 970                 975

Glu Gly Glu Pro Asp Thr Gly Tyr Arg Val Ser Val Trp Ala Glu Thr
            980                 985                 990

Lys Gly Gly Glu Gly Pro Lys Val  Val Arg Pro Val Arg  Thr Trp Pro
        995                 1000                 1005

Leu Arg  Glu Pro Asp Val Pro  Asn Phe Thr Val Glu  Ala Ile Ser
    1010                 1015                 1020

Pro Thr  Thr Ala Arg Val Gln  Trp Leu Pro Ser Asn  Gly Ser Glu
    1025                 1030                 1035

Trp Ala  Met Pro Gly Pro Ile  Phe Leu Val Asn Tyr  Ser Ile Ala
    1040                 1045                 1050

Asn Ser  Asn Asn Trp Ile Glu  Ser Glu Gln Ile Ser  Leu Pro Arg
    1055                 1060                 1065

Thr Glu  Val Trp Leu Ser Asp  Leu Glu Glu Asp Thr  Arg Tyr Lys
    1070                 1075                 1080

Met Ile  Gly Ile Ala Lys Glu  Gly Gln Arg Gln Arg  Ala Ser Glu
    1085                 1090                 1095

Ile Ile  Thr Met Arg Ser Leu  Ser Arg Ala Thr Ile  Thr His Ile
    1100                 1105                 1110

Ser His  Glu Ser Leu Gln Ser  Ala Ala Trp Phe Ile  Ala Val Val
    1115                 1120                 1125

Ser Ala  Ile Met Phe Ala Leu  Phe Thr Ala Ser Val  Met Cys Cys
    1130                 1135                 1140

Cys Glu  Arg Gln Arg Asp Ser  Lys Tyr Ser Val Lys  Gln Lys Glu
    1145                 1150                 1155

Leu Glu  Gln Gly His His Ile  Asp Ile Glu Glu Asp  Gln Asn Phe
    1160                 1165                 1170

Met Glu  Tyr Leu Tyr Gly Phe  Lys
    1175                 1180

<210> SEQ ID NO 4
<211> LENGTH: 3744
<212> TYPE: DNA
<213> ORGANISM: Brugia malayi
<220> FEATURE:
<223> OTHER INFORMATION: mRNA sequence of Bma-LAD -2

<400> SEQUENCE: 4
gtcgctctat cctgttttta aacagttgtg tagcgacaat atcagtgacc ggcatgatta      60
cgctatctat tctttggtgt tcgctttttc aatttattgc tttcagccgt acactcggtc     120
caccaaaact agatccagaa aatggtggag aagtatggtt tcaagtgaat tcgaccggta     180
tcgcacgtgg taaatttatt cttccgtgct atgccactgg taatccagaa acatatgagt     240
ggtttaagga tggagaaaaa ctaaaagttg atggtgatag gattgcgtgg gaaaaacaat     300
tccaaagcgg taccataata atcaatgacg ctcgagatgg agatcaaggt tattatcagt     360
gtcacgcctc caatattttt gggattgctg tttccaataa atttcacgtg caaattggag     420
ttcttgatca ttttgtgccc cgaggtgtgc gtcgattgat agtagacgaa ggacaaagct     480
taagtattcg atgtgatatt ccgtatgggg tgccaaaacc atctgttttt tggctttatc     540
gcgatacaca acgaacaaat atgatcgaaa ctattcgata caaacatatt gctgtcgata     600
ccgaaggtac ccttcatttc acagcggtta aaaaacatga cgggcggcaa aatttaattt     660
accaatgcgc agtgacttct cctgtactgc gtggggaata tcgtgcaggc aacgaattcc     720
```

-continued

```
aacttattgt caatcctgct aaaaaaaaca atggaacggc tatacataag ctgtggttta     780
gtccagaaaa agtatctgtc aaagtaggaa ccaaactcaa actgatgtgc atcttcggtg     840
gaaggccact accgaacata acgtggagta aattaaatga tgatttgccg cttgctcgct     900
taaagatttt aaatcacaag aagctgacta cggtaaagct ctgatcatcg aaaatgttcg     960
ttcagaagat gcggggatat atgaatgtcg atcacagcat ctatttcatc agatgcatgt    1020
tactaccaat gcagctccat tttggataga taaaccaccg gaagacattg acgaaccgga    1080
aggaagtagc gctgaaatcc attgcacaat atcgggcatc ccaacaccca tcattcagtg    1140
gttcatcaat ggtgtacctt tacatgagtt ggcagacaat gatcgacgta tgattttaaa    1200
tagtggtcag atattacgaa tcgtaaactt ggatcatgat gttgatacag ccgtatatca    1260
gtgcaatgca tcgaatccgt ttggatacgt ttttggaaat gctttcgtga atgtgcgcgc    1320
ttatgctcca tatttcaaaa tgccaagtca ccgtatctgg aatgtggtgc gtaaatcaac    1380
cgtagagatg tcgtgcgatg ttgaagcagc accgaaagca gtggtcaaat gggtagacac    1440
taatgatcat tccattgctg ttgttctcga aaaaatcaat attttcccca atcacacatt    1500
gcgcatatcg caagtaaatt cggctgatga aggcctttac tattgcaatg tatcgaacaa    1560
gtatggtatc aatcgagctg ttaatcaact acaagttttc aatccaacac attttattcg    1620
tgtaccaagt ccaaagaagt caatattgga agcgcatgag tcagtggaat atgtgtgtga    1680
agcagtttgt gatccacggc ttacgattga atattcttgg acccataatg gaataccaat    1740
taatgattct gtccacttca agctattaaa caattctctg ttaatcgtta atgctcgtgg    1800
ctttcattca ggaaccattg attgtattgt tcttaccgat gttgacgtca agatttcagg    1860
aattgaatta actgtgcttg atgtgcctgc tgctccaata ataacaggaa taaactgcaa    1920
cgagcgaaga gcgatgttaa ggtggcgtcg accagatgac cacggtgacc aaatcaaaca    1980
gtttctcatt caaatgcata ctgaatttga agaaggattg tggcaaactg ttgtggagga    2040
agaaaatact gctgccgatt tttatcaggc tgatattgca ctttcaccgt gggtaaatta    2100
tacatttcgt ataatagctc ggaattcacg tggtgaaagt gaacccggct tcaaagaagg    2160
catagtgtgt tccacgaaag cttactatcc atttacaaat ccaaaggatg tccgagccga    2220
aggcagtgaa ccaaacaata tgattatcga atggaagcct atggataaat atgattggaa    2280
cggaccagga ttacagtaca tcgtccgtta taagtttaat aaaccagggg aagcttggac    2340
agaaatacga attgaagatc ctttagccaa ttatacagtt attcgcgaac agccaacatt    2400
cagagaatat ttgattcaag ttgaatctct gaatagtttt ggtcgcgcag ttgtgaaacc    2460
aacgagtgtt aaaggatatt caggagaaga cacccactg ttgtcgccga ttgatttcag    2520
cgtgtctgaa ttcataaatt gtactgctgt tcttcttata tggaaacacg tggatcgaga    2580
cagtgtgcgt ggtcatttca aaggttatct gattgactat tgggaaaatg agaagccatt    2640
tgctataatg aatgctggag ctgaaaaaca taagaatgag acgattcttt atgatctaaa    2700
gcctatgaca aactatacgg cacgtattag aacagcgaat agtcgatacc taagtgaatc    2760
tccatcaata atcaaatttta caactcctga aggaattcca tccaaggtac acaatatgag    2820
agtacgagca gttggagcaa gaagcttgta tgttacatgg gaaccaccgc gacaaccaaa    2880
tggatacgtc cgcggctatt tcattacttt tgaaaattcc tcgacaggcg taaaagaaga    2940
aacatttgta ctaaatcgac aactttatta tttaaatgaa gaaggtgagc cagacactgg    3000 ctataggggtt tctgtttggg cagaaacgaa aggtggtgaa ggaccaaaag ttgttcgccc    3060
```

-continued

```
agtacgaact tggccacttc gagaaccgga tgtaccaaat ttcaccgtcg aagcaatttc    3120
gcctacaacg gctcgagttc aatggttgcc ttcgaatggt tccgaatggg ctatgccagg    3180
gcctattttt cttgtcaatt attctattgc caacagcaat aattggatag aaagtgaaca    3240
aataagtttg cctcgaactg aagtatggtt aagcgatcta gaagaagaca cacgatataa    3300
aatgattggt atcgctaagg aaggtcaaag gcagcgagca tccgaaataa ttaccatgcg    3360
aagcctaagt cgagctacga ttacacacat ttctcatgaa agcttgcaaa gtgcagcctg    3420
gttcatcgca gtagtgagtg caataatgtt tgcattattc actgcatcag taatgtgttg    3480
ctgcgaacgg caacgagata gtaaatattc cgttaaacag aaagaattgg aacaaggcca    3540
tcatatcgat atcgaagagg accagaattt tatggaatac ctgtatggat tcaaatgatt    3600
aactatcata ttatcgcttg ttccatctaa taccaataaa ccatatctat attacatcat    3660
ttgcccctaa ttcatatact gcccgattga taaaattcac actcaactat gtatgtctct    3720
ttctctattt acatcactac gcgg                                           3744
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-iUGT siRNA 1 sense
<220> FEATURE:
<223> OTHER INFORMATION: 3 dTdT overhang

<400> SEQUENCE: 5
gccuaacgaa acuaagcaat t                                                 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-iUGT siRNA 1 antisense
<220> FEATURE:
<223> OTHER INFORMATION: 3 dTdT overhang

<400> SEQUENCE: 6
uugcuuaguu ucguuaggct t                                                 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-iUGT siRNA 2 sense
<220> FEATURE:
<223> OTHER INFORMATION: 3 dTdT overhang
```

-continued

<400> SEQUENCE: 7
ggcuuccaca aucugauuut t                                           21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-iUGT siRNA 2 antisense
<220> FEATURE:
<223> OTHER INFORMATION: 3 dTdT overhang

<400> SEQUENCE: 8
aaaucagauu guggaagcct t                                           21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-iUGT siRNA 3 sense
<220> FEATURE:
<223> OTHER INFORMATION: 3 dTdT overhang

<400> SEQUENCE: 9
ggugguauga auagcauaat t                                           21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-iUGT siRNA 3 antisense
<220> FEATURE:
<223> OTHER INFORMATION: 3 dTdT overhang

<400> SEQUENCE: 10
uuaugcuauu cauaccacct t                                           21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-gapdh Forward primer

<400> SEQUENCE: 11
ttgatctcac ttgccgactc                                            20

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-gapdh Reverse primer

<400> SEQUENCE: 12
tggtcttcgg tgtattccaa                                                  20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-gapdh Internal probe

<400> SEQUENCE: 13
cagctaatgg accgatgaag ggga                                             24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-iugt Forward primer

<400> SEQUENCE: 14
tatcattcgg caccgttaca                                                  20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-iugt Reverse primer

<400> SEQUENCE: 15
attcatacca ccatgcgtca                                                  20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-iugt Internal probe

<400> SEQUENCE: 16
tcgctgaggg acgtccaaac g                                                21

<210> SEQ ID NO 17
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Bma-iUGT peptide sequence

<400> SEQUENCE: 17

Cys Tyr Glu Lys Asp Glu His Leu Ile Ala Glu Gly Arg Pro Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Bma-iUGT peptide sequence

<400> SEQUENCE: 18

Asp Ser Thr Gly Ser Lys Leu Ala Lys Thr Val Lys Ile Asp Cys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Bma-iUGT peptide sequence

<400> SEQUENCE: 19

Cys Gly Gln Ile Ala Asn Phe Asp Pro Tyr Gly Arg Lys Met Ser
1               5                   10                  15

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-LAD-2 siRNA 1 sense
<220> FEATURE:
<223> OTHER INFORMATION: 3 dTdT overhang

<400> SEQUENCE: 20
gcaaguacua ccauacuaut t                                            21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-LAD-2 siRNA 1 antisense
<220> FEATURE:
```

<223> OTHER INFORMATION: 3 dTdT overhang

<400> SEQUENCE: 21
auaaguugga auucguugct t                                                          21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-LAD-2 siRNA 2 sense
<220> FEATURE:
<223> OTHER INFORMATION: 3 dTdT overhang

<400> SEQUENCE: 22
gcgcauaucg caaguaaaut t                                                          21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-LAD-2 siRNA 2 antisense
<220> FEATURE:
<223> OTHER INFORMATION: 3 dTdT overhang

<400> SEQUENCE: 23
auuuacuugc gauaugcgct t                                                          21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-LAD-2 siRNA 3 sense
<220> FEATURE:
<223> OTHER INFORMATION: 3 dTdT overhang

<400> SEQUENCE: 24
gcgaauaguc gauaccuaat t                                                          21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-LAD-2 siRNA 3 antisense
<220> FEATURE:
<223> OTHER INFORMATION: 3 dTdT overhang

<400> SEQUENCE: 25
uuagguaucg acuauucgct t                                              21

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-Fukutin siRNA 1 sense
<220> FEATURE:
<223> OTHER INFORMATION: 3 dTdT overhang

<400> SEQUENCE: 26
ccacccattt cgcagattt                                                 19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Fukutin siRNA 1 antisense
<220> FEATURE:
<223> OTHER INFORMATION: 3 dTdT overhang

<400> SEQUENCE: 27
aaaucugcga aauggguggt t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-Fukutin siRNA 2 sense
<220> FEATURE:
<223> OTHER INFORMATION: 3 dTdT overhang

<400> SEQUENCE: 28
ggagcgagag tgaatggaat t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Fukutin siRNA 2 antisense
<220> FEATURE:
<223> OTHER INFORMATION: 3 dTdT overhang

<400> SEQUENCE: 29

-continued uuccauucac ucucgcucct t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-Fukutin siRNA 3 sense
<220> FEATURE:
<223> OTHER INFORMATION: 3 dTdT overhang

<400> SEQUENCE: 30
gctaacgttg caaattattt t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Fukutin siRNA 3 antisense
<220> FEATURE:
<223> OTHER INFORMATION: 3 dTdT overhang

<400> SEQUENCE: 31
aauaauuugc aacguuagct t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-ShTK siRNA 1 sense
<220> FEATURE:
<223> OTHER INFORMATION: 3 dTdT overhang

<400> SEQUENCE: 32
gcgccttcta cagcagtaat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-ShTK siRNA 1 antisense
<220> FEATURE:
<223> OTHER INFORMATION: 3 dTdT overhang

<400> SEQUENCE: 33
gcgccuucua cagcaguaat t                                              21

<210> SEQ ID NO 34
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-ShTK siRNA 2 sense
<220> FEATURE:
<223> OTHER INFORMATION: 3 dTdT overhang

<400> SEQUENCE: 34
ggugguauga auagcauaat t                                                        21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-ShTK siRNA 2 antisense
<220> FEATURE:
<223> OTHER INFORMATION: 3 dTdT overhang

<400> SEQUENCE: 35
uuaugcuauu cauaccacct t                                                        21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-ShTK siRNA 3 sense

<400> SEQUENCE: 36
gcuaaagaac uaugcgcuat t                                                        21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-ShTK siRNA 3 antisense
<220> FEATURE:
<223> OTHER INFORMATION: 3 dTdT overhang

<400> SEQUENCE: 37
uagcgcauag uucuuuagct t                                                        21

<210> SEQ ID NO 38
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Serpin siRNA sense
<220> FEATURE:
<223> OTHER INFORMATION: 3 dTdT overhang

<400> SEQUENCE: 38
ggauuucgag ugagacaaat t                                                       21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Serpin siRNA antisense
<220> FEATURE:
<223> OTHER INFORMATION: 3 dTdT overhang

<400> SEQUENCE: 39
uuugucucac ucgaaaucct t                                                       21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-EGF-like-02820 siRNA sense
<220> FEATURE:
<223> OTHER INFORMATION: 3 dTdT overhang

<400> SEQUENCE: 40
guaucgaggg caagggaaat t                                                       21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-EGF-like-02820 siRNA antisense
<220> FEATURE:
<223> OTHER INFORMATION: 3 dTdT overhang

<400> SEQUENCE: 41
uuucccuugc ccucgauact t                                                       21

<210> SEQ ID NO 42
<211> LENGTH: 21
```

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-EGF-like-48010 siRNA sense
<220> FEATURE:
<223> OTHER INFORMATION: 3 dTdT overhang

<400> SEQUENCE: 42
gcaacaaaug caagaauaat t                                                21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-EGF-like-48010 siRNA antisense
<220> FEATURE:
<223> OTHER INFORMATION: 3 dTdT overhang

<400> SEQUENCE: 43
uuauucuugc auuuguugct t                                                21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Peptidase siRNA 1 sense
<220> FEATURE:
<223> OTHER INFORMATION: 3 dTdT overhang

<400> SEQUENCE: 44
aggaaagguu guuaggauat t                                                21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Peptidase siRNA 1 antisense
<220> FEATURE:
<223> OTHER INFORMATION: 3 dTdT overhang

<400> SEQUENCE: 45
uauccuaaca accuuuccut t                                                21

<210> SEQ ID NO 46

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Reprolysin siRNA 3 sense
<220> FEATURE:
<223> OTHER INFORMATION: 3 dTdT overhang

<400> SEQUENCE: 46
ggauaaugug aaaggaauat t                                                         21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Bma-Reprolysin siRNA 3 antisense
<220> FEATURE:
<223> OTHER INFORMATION: 3 dTdT overhang

<400> SEQUENCE: 47
uauuccuuuc acauuaucct t                                                         21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-gapdh Forward primer

<400> SEQUENCE: 48
ttgatctcac ttgccgactc                                                           20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-gapdh Reverse primer

<400> SEQUENCE: 49
tggtcttcgg tgtattccaa                                                           20

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-gapdh Internal probe
```

```
<400> SEQUENCE: 50
cagctaatgg accgatgaag ggga                                      24

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-lad-2 Forward primer

<400> SEQUENCE: 51
gtgatccacg gcttacgatt                                           20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-lad-2 Reverse primer

<400> SEQUENCE: 52
caggcacatc aagcacagtt                                           20

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-lad-2 Internal probe

<400> SEQUENCE: 53
tgctcgtggc tttcattcag ga                                        22

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-fukutin Forward primer

<400> SEQUENCE: 54
aggttatttc atgtgccctg c                                         21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-fukutin Reverse primer

<400> SEQUENCE: 55
attccattca ctctcgctcc a                                         21
```

-continued

```
<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-fukutin Internal probe

<400> SEQUENCE: 56
aggcggatta cggtaattgg cgagt                                          25

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-shtk Forward primer

<400> SEQUENCE: 57
tgcactgatc caatggcaaa                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-shtk Reverse primer

<400> SEQUENCE: 58
gttactgctg tagaaggcgc                                               20

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-shtk Internal probe

<400> SEQUENCE: 59
tgcgccaaaa catgtggatt ttgcgg                                        26

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-serpin Forward primer

<400> SEQUENCE: 60
acgtgcgcag ttagactttg                                               20

<210> SEQ ID NO 61
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-serpin Reverse primer

<400> SEQUENCE: 61
gcctctgcga tataagccaa                                              20

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-serpin Internal probe

<400> SEQUENCE: 62
gcggacggtg aaacgaagca gca                                          23

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-egf-like-02820 Forward primer

<400> SEQUENCE: 63
gcttacacgg tggcagaaaa                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-egf-like-02820 Reverse primer

<400> SEQUENCE: 64
aagccaccta tctgctctcc                                              20

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-egf-like-02820 Internal probe

<400> SEQUENCE: 65
tcgagggcaa gggaaaactg gaa                                          23

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<223> OTHER INFORMATION: Bma-egf-like-48010 Forward primer

<400> SEQUENCE: 66
acctggcttc atgggagaaa                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-egf-like-48010 Reverse primer

<400> SEQUENCE: 67
cttcaccaca gtcgcaaaca                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-egf-like-48010 Internal probe

<400> SEQUENCE: 68
tgctgccggt cttatgggcg                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-peptidase Forward primer

<400> SEQUENCE: 69
cagccattat tggccaggac                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-peptidase Reverse primer

<400> SEQUENCE: 70
aaatgaagtg gtgccgcatt                                              20

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-peptidase Internal probe

<400> SEQUENCE: 71
```
agccttccaa cttggttcat cccaaca                                                          27

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-reprolysin Forward primer

<400> SEQUENCE: 72
tggaacacag tgatcaggct                                                                  20

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-reprolysin Reverse primer

<400> SEQUENCE: 73
aacggcattc cacttatcg                                                                   19

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bma-reprolysin Internal probe

<400> SEQUENCE: 74
cccatttcgt gtgcaatagt tgcagca                                                          27

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Tyr Glu Lys Asp Glu His Leu Ile Ala Glu Gly Arg Pro Asn
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Ser Thr Gly Ser Lys Leu Ala Lys Thr Val Lys Ile Asp Cys
1               5                   10                  15

<210> SEQ ID NO 77
<211> LENGTH: 15

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Gly Gln Ile Ala Asn Phe Asp Pro Tyr Gly Arg Lys Met Ser
1               5                   10                  15
```